United States Patent
Suzuki et al.

(10) Patent No.: US 8,222,417 B2
(45) Date of Patent: Jul. 17, 2012

(54) COMPOUND HAVING 11β-HSD1 INHIBITORY ACTIVITY

(75) Inventors: Ryo Suzuki, Toshima-ku (JP); Ayako Mikami, Toshima-ku (JP); Hiroaki Tanaka, Toshima-ku (JP); Hiroshi Fukushima, Toshima-ku (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 402 days.

(21) Appl. No.: 12/666,802

(22) PCT Filed: Jun. 24, 2008

(86) PCT No.: PCT/JP2008/061452
§ 371 (c)(1),
(2), (4) Date: Dec. 26, 2009

(87) PCT Pub. No.: WO2009/001817
PCT Pub. Date: Dec. 31, 2008

(65) Prior Publication Data
US 2010/0179325 A1    Jul. 15, 2010

(30) Foreign Application Priority Data

Jun. 27, 2007   (JP) .................................. 2007-169824
Aug. 8, 2007    (JP) .................................. 2007-207294
Dec. 5, 2007    (JP) .................................. 2007-315236

(51) Int. Cl.
*C07D 215/38*   (2006.01)
*A61K 31/04*    (2006.01)

(52) U.S. Cl. .................. 546/159; 548/491; 514/312

(58) Field of Classification Search .................. 546/159; 548/491; 514/312
See application file for complete search history.

(56) References Cited

U.S. PATENT DOCUMENTS

| | | | | |
|---|---|---|---|---|
| 7,855,215 | B2 * | 12/2010 | Bold et al. ................. | 514/227.8 |
| 2005/0256159 | A1 | 11/2005 | Barton et al. | |
| 2008/0064693 | A1 | 3/2008 | Jaroskova et al. | |

FOREIGN PATENT DOCUMENTS

| | | |
|---|---|---|
| JP | 2006-506451 A | 2/2006 |
| WO | 2005/108368 A1 | 11/2005 |
| WO | 2006/024627 A2 | 3/2006 |
| WO | 2006/048750 A2 | 5/2006 |
| WO | 2006/074244 A2 | 7/2006 |
| WO | 2007/068330 A1 | 6/2007 |
| WO | 2008/024497 A2 | 2/2008 |

OTHER PUBLICATIONS

International Search Report dated Aug. 12, 2008, issued in International Application No. PCT/JP2008/061452.

\* cited by examiner

*Primary Examiner* — D M Seaman
(74) *Attorney, Agent, or Firm* — Sughrue Mion, PLLC

(57) ABSTRACT

The present invention provides compounds having excellent 11β-HSD1 inhibitory activity.
A compound represented by the following formula (I):

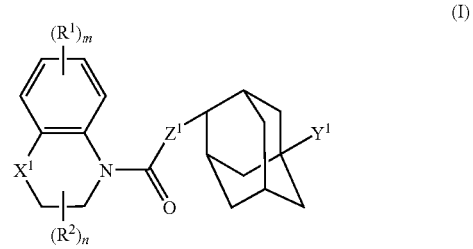

[wherein
$X^1$ represents an oxygen atom, or the formula —$(CR^{11}R^{12})_p$—, etc.,
$Y^1$ represents a hydrogen atom, a hydroxyl group, etc.,
$Z^1$ represents an oxygen atom or the formula —$(NR^{14})$—,
$R^1$ represents a hydrogen atom, a halogen atom, a cyano group, a $C_{1-4}$ alkyl group, a $C_{1-4}$ alkyl group substituted with 1 to 3 halogen atoms, a $C_{1-4}$ alkoxy group, a $C_{1-4}$ alkoxycarbonyl group, a carboxyl group, a carbamoyl group, or an amino group, and m represents an integer of 1 or 2, and
$R^2$ represents a hydrogen atom or a $C_{1-4}$ alkyl group, and n represents an integer of 1 or 2].

9 Claims, No Drawings

COMPOUND HAVING 11β-HSD1 INHIBITORY ACTIVITY

CROSS REFERENCE TO RELATED APPLICATIONS

This application is a National Stage of International Application No. PCT/JP2008/061452 filed Jun. 24, 2008, claiming priorities based on Japanese Patent Application Nos. 2007-169824, filed Jun. 27, 2007, 2007-207294 filed Aug. 8, 2007 and 2007-315236 filed Dec. 5, 2007, the contents of all of which are incorporated herein by reference in their entirety.

TECHNICAL FIELD

The present invention relates to compounds which are useful as 11β-hydroxysteroid dehydrogenase type 1 (11β-HSD1) inhibitors.

BACKGROUND ART

11β-HSD1 is an enzyme catalyzing the conversion of cortisone (inactive glucocorticoid) into cortisol (glucocorticoid), and is expressed primarily in the liver, visceral fat, etc. 11β-HSD1 functions locally and appears to serve as a factor amplifying intracellular cortisol levels in each organ. 11β-HSD1 is responsible for gluconeogenesis in the liver and is also related to accumulation of visceral fat. When the activity of this enzyme is inhibited, it is expected to provide a hypoglycemic effect in the liver due to inhibited gluconeogenesis and an inhibitory effect against fat accumulation in visceral fat. Thus, 11β-HSD1 inhibitors can be expected to be effective against obesity, impaired glucose tolerance, insulin resistance, hyperglycemia, hyperlipidemia, hypertension and metabolic syndrome (see Patent Document 1).

In addition, inhibition of 11β-HSD1 can suppress an increase in local glucocorticoid levels, and diseases whose conditions are ameliorated thereby include mental diseases (e.g., neurodegenerative disease, cognitive impairment, dementia, depression), osteoporosis, insufficient intraocular pressure-induced conditions including glaucoma (see Patent Document 1), vascular diseases and diabetic complications such as arteriosclerosis, cardiovascular disease, cerebral infarction, peripheral vascular disease, hypertension, diabetic nephropathy, and diabetic neuropathy (see Patent Document 2), Cushing's syndrome (see Patent Document 3), muscle wasting (see Patent Document 4), as well as diseases that will be more likely mediated by cellular immunity than by humoral immunity, such as tuberculosis, Hansen's disease, and psoriasis (see Patent Document 5).

As inhibitors of 11β-HSD1, various compounds have been reported previously, including thiazole derivatives, triazole derivatives, pyrrolidinone derivatives, and so on (see Patent Documents 6 to 19). In addition, there is a report of 2-adamantylurea derivatives (see Patent Document 20). However, there is no knowledge about derivatives relevant to the compounds of the present invention, i.e., tetrahydroquinoline derivatives, indoline derivatives, tetrahydrobenzoazepine derivatives, dihydrobenzoxazine derivatives, tetrahydroquinoxaline derivatives or dihydrobenzothiazine derivatives, each having a substituted adamantylaminocarbonyl group or a substituted adamantyloxycarbonyl group in their side chain. Moreover, these known 11β-HSD1 inhibitors cannot exert sufficient activity, and there is a demand for the development of compounds that have a therapeutic effect based on the inhibitory effect against 11β-HSD1 and that are satisfactory for use as pharmaceutical preparations.

Patent Document 1: International Publication No. WO06/055752
Patent Document 2: International Publication No. WO06/068992
Patent Document 3: International Publication No. WO06/066109
Patent Document 4: International Publication No. WO06/040329
Patent Document 5: International Publication No. WO05/110980
Patent Document 6: International Publication No. WO01/090090
Patent Document 7: International Publication No. WO01/090091
Patent Document 8: International Publication No. WO01/090092
Patent Document 9: International Publication No. WO01/090093
Patent Document 10: International Publication No. WO01/090094
Patent Document 11: International Publication No. WO03/065983
Patent Document 12: International Publication No. WO03/104207
Patent Document 13: International Publication No. WO05/108360
Patent Document 14: International Publication No. WO05/108368
Patent Document 15: International Publication No. WO06/024627
Patent Document 16: International Publication No. WO06/024628
Patent Document 17: International Publication No. WO06/048750
Patent Document 18: International Publication No. WO06/074244
Patent Document 19: International Publication No. WO06/104280
Patent Document 20: International Publication No. WO07/068,330

DISCLOSURE OF THE INVENTION

Problems to be Solved by the Invention

The object of the present invention is to provide compounds having excellent 11β-HSD1 inhibitory activity.

Means for Solving the Problems

As a result of extensive and intensive efforts made to achieve the above object, the inventors of the present invention have found that compounds represented by the following formula (I), (II), (III), (IV), (V) or (VI) have excellent 11β-HSD1 inhibitory activity. This finding led to the completion of the present invention.

Namely, the present invention provides a compound represented by the following formula (I):

[Formula 1]

(I)

[wherein
$X^1$ represents an oxygen atom, or the formula $—(CR^{11}R^{12})_p—$ (wherein $R^{11}$ and $R^{12}$, which may be the same or different, each represent a hydrogen atom or a $C_{1-4}$ alkyl group, and p represents an integer of 0 to 2), a sulfur atom, the formula $—S(O)—$, the formula $—S(O)_2—$, or the formula $—N(R^{13})—$ (wherein $R^{13}$ represents a hydrogen atom, a $C_{1-4}$ alkyl group, a $C_{1-4}$ alkylcarbonyl group or a $C_{1-4}$ alkoxycarbonyl group), $Y^1$ represents a hydrogen atom, a hydroxyl group, a halogen atom, a $C_{1-4}$ alkoxy group, a $C_{1-4}$ alkoxycarbonyl group, a carboxyl group, a carbamoyl group, a $C_{1-4}$ alkylsulfonyl group, a $C_{1-4}$ alkylsulfonyl-$C_{1-4}$ alkoxy group, or a carbamoylmethoxy group, $Z^1$ represents an oxygen atom or the formula $—(NR^{14})—$ (wherein $R^{14}$ represents a hydrogen atom or a $C_{1-4}$ alkyl group), $R^1$ represents a hydrogen atom, a halogen atom, a cyano group, a $C_{1-4}$ alkyl group, a $C_{1-4}$ alkyl group substituted with 1 to 3 halogen atoms, a $C_{1-4}$ alkoxy group, a $C_{1-4}$ alkoxycarbonyl group, a carboxyl group, a carbamoyl group, or an amino group, and m represents an integer of 1 or 2, and $R^2$ represents a hydrogen atom or a $C_{1-4}$ alkyl group, and n represents an integer of 1 or 2].

In another embodiment, the present invention provides a compound represented by the following formula (II):

[Formula 2]

(II)

[wherein
$X^1$ represents an oxygen atom, or the formula $—(CR^{11}R^{12})_p—$ (wherein $R^{11}$ and $R^{12}$, which may be the same or different, each represent a hydrogen atom or a $C_{1-4}$ alkyl group, and p represents an integer of 0 to 2), a sulfur atom, the formula $—S(O)—$, the formula $—S(O)_2—$, or the formula $—N(R^{13})—$ (wherein $R^{13}$ represents a hydrogen atom, a $C_{1-4}$ alkyl group, a $C_{1-4}$ alkylcarbonyl group or a $C_{1-4}$ alkoxycarbonyl group), $Y^1$ represents a hydroxyl group, a halogen atom, a $C_{1-4}$ alkoxy group, a $C_{1-4}$ alkoxycarbonyl group, a carboxyl group, a carbamoyl group, a $C_{1-4}$ alkylsulfonyl group, a $C_{1-4}$ alkylsulfonyl-$C_{1-4}$ alkoxy group, or a carbamoylmethoxy group, $Z^1$ represents an oxygen atom or the formula $—(NR^{14})—$ (wherein $R^{14}$ represents a hydrogen atom or a $C_{1-4}$ alkyl group), $R^1$ represents a hydrogen atom, a halogen atom, a cyano group, a $C_{1-4}$ alkyl group, a $C_{1-4}$ alkyl group substituted with 1 to 3 halogen atoms, a $C_{1-4}$ alkoxy group, a $C_{1-4}$ alkoxycarbonyl group, a carboxyl group, a carbamoyl group, or an amino group, and m represents an integer of 1 or 2, and $R^2$ represents a hydrogen atom or a $C_{1-4}$ alkyl group, and n represents an integer of 1 or 2].

In yet another embodiment, the present invention provides a compound represented by the following formula (III):

[Formula 3]

(III)

[wherein
$X^2$ represents an oxygen atom or the formula $—(CR^{21}R^{22})_r—$ (wherein $R^{21}$ and $R^{22}$, which may be the same or different, each represent a hydrogen atom or a $C_{1-4}$ alkyl group, and r represents an integer of 0 to 2), $Y^2$ represents a hydrogen atom, a hydroxyl group, a halogen atom, a $C_{1-4}$ alkoxy group, a $C_{1-4}$ alkoxycarbonyl group, a carboxyl group, or a carbamoyl group, $Z^2$ represents an oxygen atom or the formula $—(NR^{23})—$ (wherein $R^{23}$ represents a hydrogen atom or a $C_{1-4}$ alkyl group), $R^3$ represents a hydrogen atom, a halogen atom, a cyano group, a $C_{1-4}$ alkyl group, or a $C_{1-4}$ alkoxy group, and m' represents an integer of 1 or 2, and $R^4$ represents a hydrogen atom or a $C_{1-4}$ alkyl group, and n' represents an integer of 1 or 2].

In yet another embodiment, the present invention provides a compound represented by the following formula (IV):

[Formula 4]

(IV)

[wherein
$X^2$ represents an oxygen atom or the formula $—(CR^{21}R^{22})_r—$ (wherein $R^{21}$ and $R^{22}$, which may be the same or different, each represent a hydrogen atom or a $C_{1-4}$ alkyl group, and r represents an integer of 0 to 2), $Y^2$ represents a hydroxyl group, a halogen atom, a $C_{1-4}$ alkoxy group, a $C_{1-4}$ alkoxycarbonyl group, a carboxyl group, or a carbamoyl group, $Z^2$ represents an oxygen atom or the formula —(NR$^{23}$)— (wherein R$^{23}$ represents a hydrogen atom or a $C_{1-4}$ alkyl group), $R^3$ represents a hydrogen atom, a halogen atom, a cyano group, a $C_{1-4}$ alkyl group, or a $C_{1-4}$ alkoxy group, and m' represents an integer of 1 or 2, and $R^4$ represents a hydrogen atom or a $C_{1-4}$ alkyl group, and n' represents an integer of 1 or 2].

In yet another embodiment, the present invention provides a compound represented by the following formula (V):

[Formula 5]

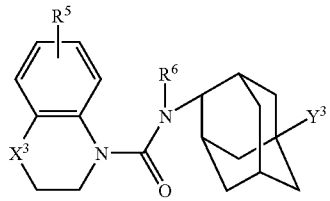

(V)

[wherein $X^3$ represents —(CH$_2$)$_s$— (wherein s represents an integer of 0 or 1), $Y^3$ represents a hydrogen atom or a hydroxyl group, $R^5$ represents a hydrogen atom, a halogen atom, a $C_{1-4}$ alkyl group or a $C_{1-4}$ alkoxy group, and $R^6$ represents a hydrogen atom or a $C_{1-4}$ alkyl group].

In yet another embodiment, the present invention provides the above compound of formula (V) in which $Y^3$ is a hydroxyl group.

In yet another embodiment, the present invention provides a compound represented by the following formula (VI):

[Formula 6]

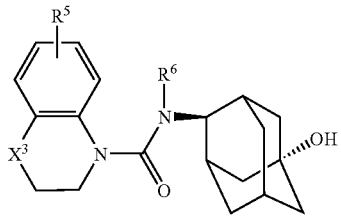

(VI)

[wherein $X^3$ represents —(CH$_2$)$_s$— (wherein s represents an integer of 0 or 1), $R^5$ represents a hydrogen atom, a halogen atom, a $C_{1-4}$ alkyl group or a $C_{1-4}$ alkoxy group, and $R^6$ represents a hydrogen atom or a $C_{1-4}$ alkyl group].

ADVANTAGES OF THE INVENTION

The present invention enables the provision of compounds having excellent 11β-HSD1 inhibitory activity.

BEST MODE FOR CARRYING OUT THE INVENTION

The compounds of the present invention will be further described in more detail below.

The term "halogen atom" is intended to include a fluorine atom, a chlorine atom, a bromine atom or an iodine atom.

The term "$C_{1-4}$ alkyl group" refers to a linear or branched alkyl group containing 1 to 4 carbon atoms. Examples include a methyl group, an ethyl group, a propyl group, an isopropyl group, a n-butyl group, and a t-butyl group.

The term "$C_{1-4}$ alkoxy group" refers to a linear or branched alkoxy group containing 1 to 4 carbon atoms. Examples include a methoxy group, an ethoxy group, a propoxy group, an isopropoxy group, a n-butoxy group, and a t-butoxy group.

The term "$C_{1-4}$ alkylcarbonyl group" refers to a carbonyl group attached to a linear or branched alkyl group containing 1 to 4 carbon atoms. Examples include an acetyl group, a propionyl group, a butyryl group, and an isobutyryl group.

The term "$C_{1-4}$ alkoxycarbonyl group" refers to a carbonyl group attached to a linear or branched alkoxy group containing 1 to 4 carbon atoms. Examples include a methoxycarbonyl group, an ethoxycarbonyl group, a propoxycarbonyl group, an isopropoxycarbonyl group, a n-butoxycarbonyl group, and a t-butoxycarbonyl group.

The term "$C_{1-4}$ alkylsulfonyl group" refers to a linear or branched alkylsulfonyl group containing 1 to 4 carbon atoms. Examples include a methylsulfonyl group, an ethylsulfonyl group, a propylsulfonyl group, an isopropylsulfonyl group, a n-butylsulfonyl group, and a t-butylsulfonyl group.

The term "$C_{1-4}$ alkylsulfonyl-$C_{1-4}$ alkoxy group" refers to a linear or branched alkoxy group containing 1 to 4 carbon atoms which is substituted with a linear or branched alkylsulfonyl group containing 1 to 4 carbon atoms. Examples include a methylsulfonylmethoxy group, a methylsulfonylethoxy group, an ethylsulfonylmethoxy group, an ethylsulfonylethoxy group, a propylsulfonylmethoxy group, a propylsulfonylethoxy group, an isopropylsulfonylmethoxy group, an isopropylsulfonylethoxy group, a n-butylsulfonylmethoxy group, a n-butylsulfonylethoxy group, a t-butylsulfonylmethoxy group, a t-butylsulfonylethoxy group, a methylsulfonylpropoxy group, a methylsulfonylbutoxy group, an ethylsulfonylpropoxy group, an ethylsulfonylbutoxy group, a propylsulfonylpropoxy group, a propylsulfonylbutoxy group, an isopropylsulfonylpropoxy group, an isopropylsulfonylbutoxy group, a n-butylsulfonylpropoxy group, a n-butylsulfonylbutoxy group, a t-butylsulfonylpropoxy group, and a t-butylsulfonylbutoxy group.

The phrase "$C_{1-4}$ alkyl group substituted with 1 to 3 halogen atoms" refers to a linear or branched alkyl group containing 1 to 4 carbon atoms which is substituted with 1 to 3 halogen atoms. Examples include a fluoromethyl group, a difluoromethyl group, a trifluoromethyl group, a 2-fluoroethyl group, a 2,2-difluoroethyl group, a 2,2,2-trifluoroethyl group, a 2-chloroethyl group, a 3,3,3-trifluoropropyl group, a 3-chloropropyl group, a 4,4,4-trifluorobutyl group, and a 4-chlorobutyl group.

The compounds of the present invention are tetrahydroquinoline derivatives, indoline derivatives, tetrahydrobenzoazepine derivatives, dihydrobenzoxazine derivatives, tetrahydroquinoxaline derivatives or dihydrobenzothiazine derivatives, which may be in the form of pharmaceutically acceptable salts or hydrates thereof. The compounds of the present invention or pharmaceutically acceptable salts thereof or hydrates thereof are hereinafter collectively referred to as "the compounds of the present invention."

The term "pharmaceutically acceptable salt" is intended to include, for example, acid addition salts such as mineral acid salts (e.g., hydrochloride salt, hydrobromide salt, hydroiodide salt, phosphate salt, sulfate salt, nitrate salt), sulfonic acid salts (e.g., methanesulfonate salt, ethanesulfonate salt, benzenesulfonate salt, p-toluenesulfonate salt), and organic acid salts (e.g., oxalate salt, tartrate salt, citrate salt, maleate salt, succinate salt, acetate salt, benzoate salt, mandelate salt, ascorbate salt, lactate salt, gluconate salt, malate salt); amino acid salts (e.g., glycine salt, lysine salt, arginine salt, ornithine salt, glutamate salt, aspartate salt); inorganic salts (e.g., lithium salt, sodium salt, potassium salt, calcium salt, magnesium salt); as well as salts with organic bases (e.g., ammonium salt, triethylamine salt, diisopropylamine salt, cyclohexylamine salt).

It should be noted that the compounds of the present invention also encompass so-called prodrugs, i.e., compounds that are metabolized in vivo into the compounds of the present invention.

The term "hydrate" is intended to mean a pharmaceutically acceptable hydrate or solvate of any compound of the present invention or a salt thereof. When exposed to air or recrystallized, the compounds of the present invention or salts thereof may absorb moisture or solvent to thereby have adsorbed water or adsorbed solvent, or alternatively, to form hydrates or solvates. Such hydrates or solvates also fall within the scope of the present invention.

The compounds of the present invention may have an asymmetric center. In this case, there are various optical isomers or configurations. Thus, the compounds of the present invention can exist in the form of separate optically active (+) and (−) isomers or a racemic or (±) mixture. In the case of compounds having two or more asymmetric centers, there are also diastereomers based on the chirality of each asymmetric center. The compounds of the present invention encompass a mixture containing all of these forms at any ratio. For example, diastereomers can be separated by techniques well known to those skilled in the art, such as fractional crystallization or the like, while optically active isomers can be obtained by organic chemistry procedures well known for this purpose. Moreover, the compounds of the present invention may have isomers such as cis- and trans-isomers. The compounds of the present invention encompass these isomers and a mixture containing these isomers at any ratio.

The compounds of the present invention have an inhibitory effect against 11β-HSD1 activity and can be used effectively against 11β-HSD1-related diseases, such as diabetes, metabolic syndrome, obesity, hypertension, arteriosclerosis, hyperlipidemia, etc. Namely, the compounds of the present invention can be used as 11β-HSD1 inhibitors for use in therapeutic or prophylactic agents for diabetes, metabolic syndrome, obesity, hypertension, arteriosclerosis, hyperlipidemia, dementia, diabetic complications, glaucoma and increased intraocular pressure-induced diseases, neurodegenerative diseases and cognitive impairment, osteoporosis, Cushing's syndrome, muscle wasting, tuberculosis, Hansen's disease, psoriasis, etc. The compounds of the present invention may be administered either alone or in combination with pharmaceutically or pharmacologically acceptable carriers or diluents. In a case where the compounds of the present invention are used as 11β-HSD1 inhibitors or the like, the compounds of the present invention may be directly administered orally or parenterally. Alternatively, the compounds of the present invention may be administered orally or parenterally in the form of preparations containing the same as an active ingredient. Parenteral administration includes intravenous administration by injection.

The compounds of the present invention may be given, for example, at 1 mg to 1000 mg, preferably 10 mg to 200 mg per administration, for example, in one to three divided doses per day. This dosage may be adjusted as appropriate depending on the age, body weight and symptoms of a patient.

To evaluate the compounds of the present invention for their ability to inhibit 11β-HSD1 activity, the evaluation may be accomplished according to any known procedure, for example, the method described in the Example section or the like.

How to prepare the compounds of the present invention will be explained in more detail below, but is not limited to the particular cases illustrated below. Moreover, any solvent may be used for each reaction as long as it is inert to the reaction, and is not limited by the following description.

[Scheme 1]

[Formula 7]

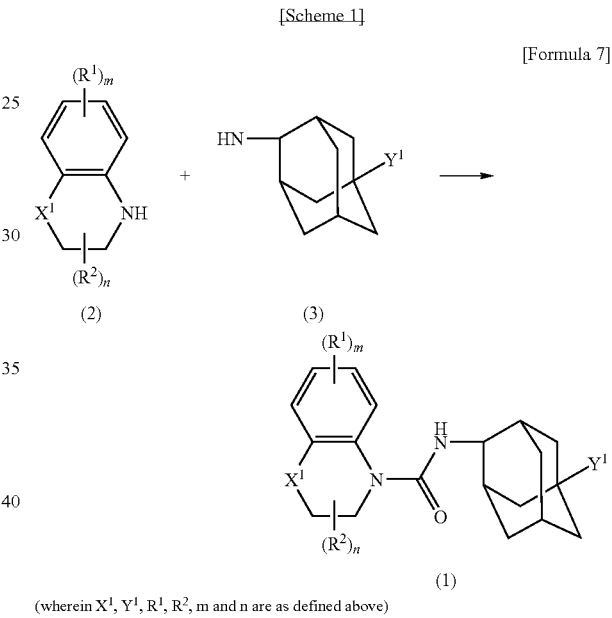

(wherein $X^1$, $Y^1$, $R^1$, $R^2$, m and n are as defined above)

Scheme 1 shows a process for synthesizing a urea derivative (1) using a cyclic amine derivative (2) and an adamantylamine derivative (3).

By way of example, in the first step, a cyclic amine derivative (2) and N,N'-carbonyldiimidazole may be used to derive an N-carbonylimidazole derivative, which is an active intermediate. In the second step, this intermediate may then be reacted with an adamantylamine derivative (3) to synthesize a urea derivative (1). The reaction in the first step may be accomplished by using an appropriate base, including an amine (e.g., triethylamine, diisopropylethylamine). Examples of a solvent available for use in this reaction include those inert to the reaction, such as dichloromethane, chloroform, 1,2-dichloroethane, N,N-dimethylformamide, tetrahydrofuran, dioxane, toluene, and ethyl acetate. The reaction using such a solvent may be performed at −50° C. to 80° C. The reaction in the second step may be accomplished by directly adding the adamantylamine derivative (3) to the reaction mixture from the first step. Alternatively, the reaction mixture from the first step may be worked up to isolate the active intermediate, i.e., the N-carbonylimidazole derivative before being subjected to the reaction in the second step. The reaction in the second step may also be accomplished by using an appropriate base, including an amine (e.g., triethylamine, diisopropylethylamine). Examples of a solvent available for use in this reaction include those inert to the reaction, such as dichloromethane, chloroform, 1,2-dichloroethane, N,N-dimethylformamide, tetrahydrofuran, dioxane, toluene, and ethyl acetate. The reaction using such a solvent may be performed at 0° C. to 150° C. Alternatively, the sequence of reactions may be altered, i.e., an adamantylamine derivative (3) may be derived into an N-carbonylimidazole derivative in the first step, which may then be reacted with a cyclic amine derivative (2) in the second step to synthesize a urea derivative (1).

Furthermore, in this process, N,N'-carbonyldiimidazole may be replaced by triphosgene, trichloromethyl chloroformate, phosgene gas, phenyl chloroformate, substituted phenyl chloroformate or N,N'-disuccinimidyl carbonate.

[Scheme 2]

[Formula 8]

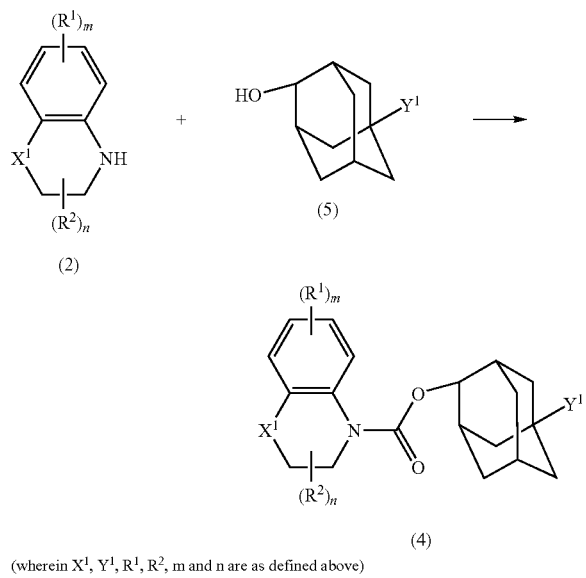

(wherein $X^1$, $Y^1$, $R^1$, $R^2$, m and n are as defined above)

Scheme 2 shows a process for synthesizing a carbamate derivative (4) using a cyclic amine derivative (2) and an adamantyl alcohol derivative (5).

By way of example, in the first step, an adamantyl alcohol derivative (5) and triphosgene may be used to derive an O-carbonyl chloride derivative, which is an active intermediate. In the second step, this intermediate may then be reacted with a cyclic amine derivative (2) to synthesize a carbamate derivative (4). The reaction in the first step may be accomplished in the presence of a base, including an amine (e.g., triethylamine, diisopropylethylamine). Examples of a solvent available for use in this reaction include chloroform, tetrahydrofuran, dioxane, and toluene. The reaction using such a solvent may be performed at −50° C. to 80° C. The reaction in the second step may be accomplished by directly adding the cyclic amine derivative (2) to the reaction mixture from the first step. Alternatively, the reaction mixture from the first step may be worked up to isolate the active intermediate, i.e., the O-carbonyl chloride derivative before being subjected to the reaction in the second step. The reaction in the second step may also be accomplished in the presence of a base, including an amine (e.g., triethylamine, diisopropylethylamine) or an inorganic base (e.g., sodium hydride, potassium hydride, n-butyllithium, sodium hydroxide, potassium hydroxide, potassium carbonate, sodium bicarbonate). Examples of a solvent available for use in this reaction include chloroform, diethyl ether, tetrahydrofuran, dioxane, toluene, acetonitrile, N,N-dimethylformamide, and water. The reaction using such a solvent may be performed at −50° C. to 150° C. Alternatively, the sequence of reactions may be altered, i.e., a cyclic amine derivative (2) may be derived into an N-carbonyl chloride derivative in the first step, and the N-carbonyl chloride derivative may then be reacted with an adamantyl alcohol derivative (5) in the second step to synthesize a carbamate derivative (4).

Furthermore, in this process, triphosgene may be replaced by N,N'-carbonyldiimidazole, trichloromethyl chloroformate, phosgene gas, phenyl chloroformate, substituted phenyl chloroformate or N,N'-disuccinimidyl carbonate.

The present invention will be further described in more detail by way of the following reference examples, examples and test example.

In the following reference examples and examples, "NH silica gel column chromatography" is intended to mean separation/purification by column chromatography using NH2-type silica gel (Chromatorex NH2-type, Fuji Silysia Chemical Ltd., Japan).

REFERENCE EXAMPLE 1

Synthesis of E-4-aminoadamantan-1-ol hydrochloride

To a solution of 5-hydroxy-2-adamantanone (10.2 g) in 8M ammonia (in methanol, 50 ml), 10% palladium on activated carbon (1.00 g) was added and stirred under a hydrogen atmosphere at room temperature for 15 hours. After the reaction mixture was filtered, the solvent was distilled off under reduced pressure and the resulting residue was purified by NH silica gel column chromatography (eluting solvent: chloroform alone→chloroform:methanol=9:1) to give 4-aminoadamantan-1-ol (10.2 g, E-form:Z-form=4:1). 4-Aminoadamantan-1-ol thus obtained (10.2 g) was dissolved by heating in tetrahydrofuran (50 ml), and 4M hydrochloric acid (in 1,4-dioxane, 20 ml) was added thereto, followed by stirring at room temperature for 16 hours. The precipitated solid was collected by filtration to give 4-aminoadamantan-1-ol hydrochloride (12.1 g, E-form:Z-form=4:1). The resulting E/Z mixture (9.15 g) was dissolved by heating in ethanol (450 ml) and water (35.5 ml), and stirred at room temperature for 2 days. The precipitated solid was collected by filtration to give the titled compound, i.e., E-4-aminoadamantan-1-ol hydrochloride (3.59 g) as a colorless powder.

1H NMR (300 MHz, DMSO-D6) δ 1.31-1.43 (m, 2 H), 1.56-1.72 (m, 6 H), 1.85-2.17 (m, 5 H), 3.17-3.25 (m, 1 H), 4.55 (s, 1 H), 8.21 (brs, 3 H).

REFERENCE EXAMPLE 2

Synthesis of E-4-aminoadamantan-1-ol

E-4-Aminoadamantan-1-ol hydrochloride obtained in Reference Example 1 (3.60 g) was dissolved in water (20 ml) and adjusted to pH 12 by addition of 2.5M aqueous sodium hydroxide (12 ml) under ice cooling. After extraction six times with chloroform, the combined organic layers were dried over anhydrous magnesium sulfate and then filtered to remove the desiccant, followed by distilling off the solvent under reduced pressure. The resulting residue was converted into a powder form by addition of n-hexane, and then collected by filtration to give the titled compound, i.e., E-4-aminoadamantan-1-ol (2.94 g) as a colorless powder.

1H NMR (300 MHz, DMSO-D6) δ 1.09-1.26 (m, 2 H), 1.47-1.77 (m, 9 H), 1.86-2.00 (m, 3 H), 2.78-2.85 (m, 1 H).

REFERENCE EXAMPLE 3

Synthesis of 5-fluoro-2,3-dihydro-1H-quinolin-4-one and 7-fluoro-2,3-dihydro-1H-quinolin-4-one To 3-fluoroaniline (5.0 g), water (50 ml) and acrylic acid (3.6 g) were added and heated under reflux for 3 hours. After cooling to room temperature, the reaction mixture was stirred for 3 days and further heated under reflux for 7 hours. After cooling at room temperature, the solvent was distilled off under reduced pressure. To the resulting residue, 8M aqueous sodium hydroxide and chloroform were added to separate the aqueous layer. The separated aqueous layer was adjusted to pH 3 with 12M aqueous hydrochloric acid under ice cooling, and then extracted with chloroform. The extracted organic layer was dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=4:1) to give 3-[N-(3-fluorophenyl)]aminopropionic acid (4.2 g) as a light-yellow powder. The compound thus obtained (3.8 g) was added to polyphosphoric acid (35g) heated at 130° C., followed by stirring for 1.5 hours. The reaction mixture was neutralized by addition of water and 8M aqueous sodium hydroxide under ice cooling, and then extracted with chloroform. The extracted organic layer was dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=9:1 to 4:1 to 2:1) to give the titled compound of low polarity, i.e., 7-fluoro-2,3-dihydro-1H-quinolin-4-one (810 mg) as a yellow powder. On the other hand, a yellow oil obtained as a compound of high polarity was crystallized from a mixture of n-hexane and diethyl ether to give the other titled compound, i.e., 5-fluoro-2,3-dihydro-1H-quinolin-4-one (110 mg) as a yellow powder.

7-Fluoro-2,3-dihydro-1H-quinolin-4-one

1H NMR (300 MHz, CHLOROFORM-D) δ 2.69 (t, J=7.0 Hz, 2 H), 3.59 (td, J=7.0 Hz, 2.2 Hz, 2 H), 4.51 (brs, 1 H), 6.33 (dd, J=10.4, 2.3 Hz, 1 H), 6.44 (td like, J=8.6, 2.3 Hz, 1 H), 7.86 (dd, J=8.9, 6.5 Hz, 1 H).

5-Fluoro-2,3-dihydro-1H-quinolin-4-one

1H NMR (300 MHz, CHLOROFORM-D) δ 2.70 (t, J=6.9 Hz, 2 H), 3.51-3.65 (m, 2 H), 4.56 (brs, 1 H), 6.31-6.48 (m, 2 H), 7.10-7.30 (m, 1 H).

REFERENCE EXAMPLE 4

Synthesis of 5-fluoro-1,2,3,4-tetrahydroquinoline

To a solution of 5-fluoro-2,3-dihydro-1H-quinolin-4-one obtained in Reference Example 3 (64 mg) in trifluoroacetic acid (5 ml), triethylsilane (0.37 ml) was added and stirred at room temperature for 16 hours. After distilling off the solvent under reduced pressure, the residue was diluted with water, adjusted to pH 11 by addition of 1M aqueous sodium hydroxide, and extracted with diethyl ether. The organic layer was washed with brine, dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=3:1). The resulting residue was diluted with chloroform, added to 1M aqueous hydrochloric acid (15 ml) and partitioned. The aqueous layer was adjusted to pH 11 by addition of 2.5M aqueous sodium hydroxide, and extracted with ethyl acetate. The organic layer was washed with brine, dried over anhydrous magnesium sulfate and then filtered to remove the desiccant, followed by distilling off the solvent under reduced pressure to give the titled compound, i.e., 5-fluoro-1,2,3,4-tetrahydroquinoline (39 mg) as a light-yellow oil.

1H NMR (300 MHz, CHLOROFORM-D) δ 1.87-1.99 (m, 2 H), 2.72 (t, J=6.6 Hz, 2 H), 3.22-3.32 (m, 2 H), 3.95 (brs, 1 H), 6.24 (d, J=8.1 Hz, 1 H), 6.28-6.38 (m, 1 H), 6.84-6.93 (m, 1 H).

REFERENCE EXAMPLE 5

Synthesis of 6-fluoro-1,2,3,4-tetrahydroquinoline

To a solution of 6-aminoquinoline (1.0 g) in 42% tetrafluoroboric acid (5 ml), sodium nitrite (527 mg) was added under ice cooling and stirred at the same temperature for 1 hour. After addition of diethyl ether:ethyl acetate=1:1 (10 ml), the reaction mixture was decanted and the precipitate was dried. To the dried product, toluene (20 ml) was added and heated under reflux for 2 hours. The reaction mixture was decanted, and the resulting residue was dissolved in 1M aqueous hydrochloric acid and alkalized with saturated aqueous sodium carbonate. Insoluble materials were filtered off and the filtrate was extracted with ethyl acetate. The organic layer was dried over anhydrous sodium sulfate and then filtered to remove the desiccant, followed by distilling off the solvent under reduced pressure. The resulting residue was purified by silica gel column chromatography (eluting solvent: n-hexane:diethyl ether=4:1 to 1:1) to give 6-fluoroquinoline (273 mg) as an orange-colored oil. To a solution of 6-fluoroquinoline thus obtained (273 mg) in methanol (50 ml), 10% palladium on activated carbon (50 mg) was added and stirred overnight under a hydrogen atmosphere (60 psi) at room temperature. After the reaction mixture was filtered, the solvent was distilled off under reduced pressure and the resulting residue was purified by silica gel column chromatography (eluting solvent: n-hexane:ethyl acetate=10:1 to 4:1) to give the titled compound, i.e., 6-fluoro-1,2,3,4-tetrahydroquinoline (172 mg) as a light-brown oil.

1H NMR (300 MHz, CHLOROFORM-D) δ 1.86-1.97 (m, 2 H), 2.74 (t, J=6.5 Hz, 2 H), 3.23-3.30 (m, 2 H), 3.69 (brs, 1 H), 6.35-6.45 (m, 1 H), 6.62-6.72 (m, 2 H).

REFERENCE EXAMPLE 6

Synthesis of 7-fluoro-1,2,3,4-tetrahydroquinoline

To a solution of 7-fluoro-2,3-dihydro-1H-quinolin-4-one obtained in Reference Example 3 (810 mg) in trifluoroacetic acid (10 ml), triethylsilane (3.9 ml) was added and stirred at room temperature for 3 days. The reaction mixture was adjusted to pH 10 to 12 by addition of 8M aqueous sodium hydroxide under ice cooling, and then extracted with chloroform. To the extracted organic layer, water and 12M aqueous hydrochloric acid were added to separate the aqueous layer. The separated aqueous layer was adjusted to pH 10 to 12 by addition of 8M aqueous sodium hydroxide, and then extracted with chloroform. The extracted organic layer was washed with brine, dried over anhydrous magnesium sulfate and then filtered to remove the desiccant, followed by distilling off the solvent under reduced pressure to give the titled compound, i.e., 7-fluoro-1,2,3,4-tetrahydroquinoline (530 mg) as a light-yellow powder.

1H NMR (300 MHz, CHLOROFORM-D) δ 1.86-1.97 (m, 2 H), 2.70 (t, J=6.4 Hz, 2 H), 3.20-3.38 (m, 2 H), 3.89 (brs, 1 H), 6.15 (dd, J=10.8, 2.6 Hz, 1 H), 6.27 (td like, J=8.5, 2.6 Hz, 1 H), 6.84 (dd, J=7.8, 7.0 Hz, 1 H).

REFERENCE EXAMPLE 7

Synthesis of 8-fluoro-1,2,3,4-tetrahydroquinoline

To a solution of 2-fluoroaniline (2.0 g) in acetonitrile (20 ml), acrylic acid (1.4 ml) was added and heated under reflux for 21 hours. After the reaction mixture was concentrated, the residue was diluted with 10% aqueous sodium hydroxide and washed with chloroform. The aqueous layer was adjusted to pH 3.3 by addition of 12M aqueous hydrochloric acid, and the precipitated crystal was collected by filtration and dried to give N-(2-fluorophenyl)-β-alanine (1.35 g) as a light-yellow solid. N-(2-Fluorophenyl)-(3-alanine thus obtained (1.30 g) was added to polyphosphoric acid (20g) heated at 130° C., followed by stirring for 2.5 hours. After addition of ice-cold water, the reaction mixture was adjusted to pH 5 with 8M aqueous sodium hydroxide. The precipitated crystal was collected by filtration to give 8-fluoro-2,3-dihydroquinolin-4(1H)-one (770 mg) as a yellow solid. To a solution of 8-fluoro-2,3-dihydroquinolin-4(1H)-one thus obtained (700 mg) in trifluoroacetic acid (20 ml), triethylsilane (4.1 ml) was added and stirred at room temperature for 2 hours. Triethylsilane (2.1 ml) was further added and stirred overnight at room temperature. After the reaction mixture was concentrated, the residue was diluted with 1M aqueous sodium hydroxide and extracted with diethyl ether. To the organic layer, 6M aqueous hydrochloric acid was added and stirred to separate the aqueous layer. The aqueous layer was alkalized with 8M aqueous sodium hydroxide and extracted with chloroform. The organic layer was washed with brine and then dried over anhydrous sodium sulfate. After the desiccant was filtered off, the solvent was distilled off under reduced pressure and the resulting residue was purified by silica gel column chromatography (eluting solvent: n-hexane:ethyl acetate=20:1) to give the titled compound, i.e., 8-fluoro-1,2,3,4-tetrahydroquinoline (427 mg) as a light-yellow oil.

1H NMR (300 MHz, CHLOROFORM-D) δ 1.90-2.01 (m, 2 H), 2.78 (t, J=6.5 Hz, 2 H), 3.27-3.41 (m, 2 H), 3.99 (brs, 1 H), 6.43-6.57 (m, 1 H), 6.66-6.84 (m, 2 H).

REFERENCE EXAMPLE 8

Synthesis of 7-methoxy-1,2,3,4-tetrahydroquinoline

To a solution of 7-hydroxy-3,4-dihydro-quinolin-2(1H)-one (1.50 g) in N,N-dimethylformamide (10 ml), potassium carbonate (1.85 g) and methyl iodide (0.63 ml) were added and stirred overnight at room temperature. Insoluble materials were filtered off and the filtrate was concentrated. The resulting residue was diluted with ethyl acetate and then washed sequentially with water, saturated aqueous sodium thiosulfate:brine (1:1) and brine, followed by distilling off the solvent under reduced pressure. The resulting residue was diluted with n-hexane, and the crystal was collected by filtration to give 7-methoxy-3,4-dihydroquinolin-2(1H)-one (1.38 g) as a colorless crystal. To a solution of 7-methoxy-3,4-dihydroquinolin-2(1H)-one thus obtained (1.38 g) in tetrahydrofuran (30 ml), lithium aluminum hydride (592 mg) was added under ice cooling, heated under reflux for 4.5 hours, and then stirred overnight at room temperature. The reaction mixture was diluted with 28% aqueous ammonia under ice cooling and filtered to remove insoluble materials. The filtrate was evaporated under reduced pressure to remove the solvent. The resulting residue was purified by silica gel column chromatography (eluting solvent: n-hexane:ethyl acetate=20:1 to 9:1) to give the titled compound, i.e., 7-methoxy-1,2,3,4-tetrahydroquinoline (1.18 g) as a yellow oil.

1H NMR (300 MHz, CHLOROFORM-D) δ 1.85-1.97 (m, 2 H), 2.69 (t, J=6.4 Hz, 2 H), 3.19-3.32 (m, 2 H), 3.73 (s, 3 H), 3.82 (brs, 1 H), 6.04 (d, J=2.5 Hz, 1 H), 6.20 (dd, J=8.2, 2.5 Hz, 1 H), 6.84 (dt, J=8.2, 0.9 Hz, 1 H).

REFERENCE EXAMPLE 9

Synthesis of 7-methyl-1,2,3,4-tetrahydroquinoline

To a solution of 7-methylquinoline (2.00 g) in methanol (40 ml), 10% palladium on activated carbon (200 mg) was added and stirred overnight under a hydrogen atmosphere (60 psi) at room temperature. After the reaction mixture was filtered through celite, the solvent was distilled off under reduced pressure and the resulting residue was purified by silica gel column chromatography (eluting solvent: n-hexane: ethyl acetate=20:1 to 10:1) to give the titled compound, i.e., 7-methyl-1,2,3,4-tetrahydroquinoline (2.05 g) as a yellow oil.

1H NMR (300 MHz, CHLOROFORM-D) δ 1.86-1.98 (m, 2 H), 2.21 (s, 3 H), 2.72 (t, J=6.5 Hz, 2 H), 3.23-3.32 (m, 2 H), 3.75 (brs, 1 H), 6.30 (s, 1 H), 6.43 (d, J=7.5 Hz, 1 H), 6.83 (d, J=7.5 Hz, 1 H).

REFERENCE EXAMPLE 10

Synthesis of 6-cyano-1,2,3,4-tetrahydroquinoline

To a solution of 1,2,3,4-tetrahydroquinoline (100 mg) in N,N-dimethylformamide (1 ml), a solution of N-bromosuccinimide (134 mg) in N,N-dimethylformamide (1 ml) was added dropwise under ice cooling and stirred at the same temperature for 1 hour. The reaction mixture was diluted with water and extracted with ethyl acetate. The extracted organic layer was washed sequentially with water and brine, dried over anhydrous magnesium sulfate and then filtered to remove the desiccant, followed by distilling off the solvent under reduced pressure to give 6-bromo-1,2,3,4-tetrahydroquinoline (137 mg) as a yellow oil.

To a solution of 6-bromo-1,2,3,4-tetrahydroquinoline thus obtained (100 mg) in N,N-dimethylformamide (2 ml), copper (I) cyanide (51 mg) was added and stirred at 160° C. for 7.5 hours under microwave irradiation using a microwave system (Biotage Initiator Sixty™). The reaction mixture was diluted with 28% aqueous ammonia and extracted with chloroform. The extracted organic layer was washed with brine, dried over anhydrous magnesium sulfate and then filtered to remove the desiccant, followed by distilling off the solvent under reduced pressure. The resulting residue was purified by preparative TLC (developing solvent: n-hexane:ethyl acetate=1:1) to give the titled compound, i.e., 6-cyano-1,2,3,4-tetrahydroquinoline (50 mg) as a light-yellow oil.

1H NMR (300 MHz, CHLOROFORM-D) δ 1.84-1.96 (m, 2 H), 2.72 (t, J=6.3 Hz, 2 H), 3.35 (t, J=5.6 Hz, 2 H), 4.48 (brs, 1 H), 6.39 (d, J=8.1 Hz, 1 H), 7.12-7.22 (m, 2 H).

REFERENCE EXAMPLE 11

Synthesis of methyl 4-aminoadamantane-1-carboxylate

To 60% fuming sulfuric acid (135 ml) stirred under heating at 80° C., a solution of 4-oxoadamantan-1-ol (15.69 g) in formic acid (250 ml) was added dropwise over 2 hours. After completion of the dropwise addition, the reaction mixture was stirred at 80° C. for 3 hours, to which formic acid (100 ml) was then added at room temperature and stirred overnight at room temperature. After addition of additional formic acid (50 ml), the reaction mixture was stirred at 80° C. for 12 hours and then stirred overnight at room temperature. The reaction mixture was poured into ice-cold water, filtered to remove insoluble materials and then extracted three times with toluene. After the combined organic layers were extracted with 4M aqueous sodium hydroxide, the aqueous layer was washed three times with chloroform. The aqueous layer was adjusted to pH 1 to 2 by addition of 12M aqueous hydrochloric acid and then extracted with chloroform. The organic layer was washed with brine and then dried over anhydrous sodium sulfate. After the desiccant was filtered off, the solvent was distilled off under reduced pressure to give 4-oxoadamantane-1-carboxylic acid (9.84 g) as a colorless powder. To a solution of 4-oxoadamantane-1-carboxylic acid thus obtained (1.50 g) in 8M ammonia/methanol (30 ml), 10% palladium on activated carbon (150 mg) was added and stirred overnight under a hydrogen atmosphere at room temperature. After addition of water (10 ml), the reaction mixture was filtered through celite and washed with methanol, and the filtrate was concentrated under reduced pressure. To the resulting crystal, acetonitrile (30 ml) was added and stirred at room temperature for 3 hours. The crystal was collected by filtration to give 4-aminoadamantane-1-carboxylic acid (1.28 g) as a colorless powder. To a solution of 4-aminoadamantane-1-carboxylic acid thus obtained (1.28 g) in methanol (13 ml), acetyl chloride (2.34 ml) was added under ice cooling and stirred at room temperature for 20 minutes and then at 45° C. for 8 hours. The reaction mixture was stirred overnight at room temperature and then further stirred at 45° C. for 4 hours. After the reaction mixture was cooled to room temperature and then concentrated, the resulting crystal was dissolved in chloroform and filtered through celite. The filtrate was concentrated under reduced pressure, and the residue was converted into a powder form by addition of acetonitrile (10 ml). The crystal was collected by filtration and washed sequentially with acetonitrile and n-hexane to give the titled compound, i.e., methyl 4-aminoadamantane-1-carboxylate (1.22 g) as a colorless powder.

1H NMR (300 MHz, CHLOROFORM-D) δ 1.58-2.40 (m, 15 H), 3.49 (brs, 1 H), 3.67 (s, 3 H).

REFERENCE EXAMPLE 12

Synthesis of 2,3,4,5-tetrahydro-1H-1-benzoazepine

To a solution of α-tetralone (5.21 g) in methanol (25 ml), hydroxyamine hydrochloride (5.28 g) and pyridine (25 ml) were added and heated under reflux for 2 hours. The reaction mixture was concentrated and crystallized from ethanol to give a first crystal. After a second crystal was further obtained from the filtrate, this filtrate was concentrated, dissolved in chloroform, washed sequentially with 1M aqueous hydrochloric acid and brine, and then dried over anhydrous sodium sulfate. The crystals obtained earlier were combined and dissolved in chloroform, washed sequentially with 1M aqueous hydrochloric acid and brine, and then dried over anhydrous sodium sulfate. The chloroform solution obtained from the filtrate and the chloroform solution obtained from the crystals were combined and concentrated. The resulting residue was converted into a powder form by addition of n-hexane. The crystal was collected by filtration to give 3,4-dihydronaphthalen-1(2H)-one oxime (5.08 g) as a light-brown powder. To polyphosphoric acid (74.1 g), 3,4-dihydronaphthalen-1(2H)-one oxime thus obtained (5.08 g) was added and stirred at 120° C. for 1 hour. After the reaction mixture was cooled to room temperature, ice-cold water was added under ice cooling and stirred. The precipitated crystal was collected by filtration, and the resulting crystal was dissolved in chloroform and dried over anhydrous sodium sulfate. After the desiccant was filtered off, the solvent was distilled off under reduced pressure to give 1,3,4,5-tetrahydro-2H-1-benzoazepin-2-one (4.47 g) as a brown powder. 1,3,4,5-Tetrahydro-2H-1-benzoazepin-2-one thus obtained (4.47 g) was dissolved in tetrahydrofuran (100 ml), to which lithium aluminum hydride (2.12 g) was then added and heated under reflux for 4 hours. The reaction mixture was cooled to room temperature, diluted with 28% aqueous ammonia under ice cooling, and then filtered to remove insoluble materials. The filtrate was evaporated under reduced pressure to remove the solvent. The resulting residue was purified by silica gel column chromatography (eluting solvent: n-hexane:ethyl acetate=20:1 to 9:1) to give the titled compound, i.e., 2,3,4,5-tetrahydro-1H-1-benzoazepine (2.92 g) as a light-yellow oil.

1H NMR (300 MHz, CHLOROFORM-D) δ 1.57-1.70 (m, 2 H), 1.74-1.86 (m, 2 H), 2.70-2.82 (m, 2 H), 2.99-3.09 (m, 2 H), 3.77 (brs, 1 H), 6.73 (d, J=7.6 Hz, 1 H), 6.82 (td, J=7.3, 1.5 Hz, 1 H), 7.03 (td, J=7.6, 1.5 Hz, 1 H), 7.10 (d, J=7.3 Hz, 1 H).

REFERENCE EXAMPLE 13

Synthesis of 4,4-dimethyl-1,2,3,4-tetrahydroquinoline

To a solution of aniline (4.43 g) in chloroform (20 ml), a solution of 3,3-dimethylacryloyl chloride (2.65 ml) in chloroform (10 ml) was added dropwise and heated under reflux for 1.5 hours. After insoluble materials were filtered off and washed with chloroform, the filtrate was washed sequentially with 1M aqueous hydrochloric acid and saturated aqueous sodium bicarbonate. The filtrate was dried over anhydrous magnesium sulfate and then filtered to remove the desiccant, followed by distilling off the solvent under reduced pressure. The resulting residue was converted into a powder form by addition of n-hexane, and then collected by filtration to give 3-methyl-N-phenylbut-2-eneamide (4.11 g) as a colorless powder. 3-Methyl-N-phenylbut-2-eneamide thus obtained (2.06 g) was melted at 130° C., to which aluminum chloride powder (1.88 g) was then added and stirred at 130° C. for 0.5 hours. After the reaction temperature was reduced to 85° C., aluminum chloride powder (0.27 g) was added and stirred at 85° C. for 1 hour. After cooling at room temperature, the reaction mixture was poured into ice-cold water and extracted with diethyl ether, and the organic layer was washed with brine. The aqueous layer was extracted with chloroform, and the resulting organic layer was combined with the organic layer obtained earlier, dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=9:1 to 1:1), and the solvent was distilled off under reduced pressure. The residue was converted into a powder form by addition of n-hexane, and then collected by filtration to give 4,4-dimethyl-3,4-dihydroquinolin-2(1H)-one (1.01 g) as a colorless powder. A suspension of lithium aluminum hydride (0.43 g) in tetrahydrofuran (5 ml) was heated under reflux, to which a solution of 4,4-dimethyl-3,4-dihydroquinolin-2(1H)-one thus obtained (1.01 g) in tetrahydrofuran (10 ml) was then added dropwise and heated under reflux for 3.5 hours. The reaction mixture was allowed to stand overnight at room temperature, diluted with 28% aqueous ammonia under ice cooling, and then filtered to remove insoluble materials. The filtrate was concentrated under reduced pressure and the resulting residue was purified by silica gel column chromatography (eluting solvent: n-hexane:ethyl acetate=19:1 to 4:1) to give the titled compound, i.e., 4,4-dimethyl-1,2,3,4-tetrahydroquinoline (0.84 g) as a light-yellow oil.

1H NMR (300 MHz, CHLOROFORM-D) δ 1.30 (s, 6 H), 1.71-1.78 (m, 2 H), 3.27-3.34 (m, 2 H), 3.86 (brs, 1 H), 6.43-6.50 (m, 1 H), 6.60-6.67 (m, 1 H), 6.91-6.98 (m, 1 H), 7.15-7.22 (m, 1 H).

REFERENCE EXAMPLE 14

Synthesis of 3,4-dihydro-2H-1,4-benzoxazine

To a solution of 2-aminophenol (8.01 g) in N,N-dimethylformamide (70 ml), potassium carbonate (51.0 g) and 1,2-dibromoethane (9.5 ml) were added and stirred at 130° C. for 7.5 hours and then at room temperature for 3 days. After addition of additional 1,2-dibromoethane (9.5 ml), the reaction mixture was stirred at 130° C. for 6 hours. The reaction mixture was diluted with ice-cold water and extracted with ethyl acetate, and the organic layer was dried over anhydrous sodium sulfate. After the desiccant was filtered off, the solvent was distilled off under reduced pressure and the resulting residue was purified by silica gel column chromatography (eluting solvent: n-hexane:ethyl acetate=20:1 to 5:1) to give the titled compound, i.e., 3,4-dihydro-2H-1,4-benzoxazine (3.77 g) as a brown oil.

1H NMR (300 MHz, CHLOROFORM-D) δ 3.40-3.45 (m, 2 H), 3.72 (brs, 1 H), 4.23-4.28 (m, 2 H), 6.57-6.81 (m, 4 H).

REFERENCE EXAMPLE 15

Synthesis of 6-methyl-3,4-dihydro-2H-1,4-benzoxazine hydrochloride

To a solution of 2-amino-4-methylphenol (5.0 g) in N,N-dimethylformamide (100 ml), potassium carbonate (28g) and 1,2-dibromoethane (10.5 ml) were added and stirred at 130° C. for 6 hours. After the reaction mixture was filtered through celite to remove solids, the filtrate was diluted with water under ice cooling and extracted with ethyl acetate. The extracted organic layer was washed with water and brine, dried over anhydrous magnesium sulfate and then filtered to remove the desiccant, followed by distilling off the solvent under reduced pressure. The resulting residue was purified by silica gel column chromatography (eluting solvent: n-hexane: ethyl acetate=4:1). The resulting brown oil was dissolved in ethyl acetate, to which 4M hydrochloric acid (in ethyl acetate) was then added and stirred at room temperature for 1 hour. The precipitated solid was collected by filtration and dried by heating under reduced pressure to give the titled compound, i.e., 6-methyl-3,4-dihydro-2H-1,4-benzoxazine hydrochloride (2.6 g) as a dark-brown powder.

1H NMR (200 MHz, DMSO-D6) δ 2.21 (s, 3 H), 3.38-3.49 (m, 2 H), 4.20-4.34 (m, 2 H), 6.69-6.93 (m, 3 H).

REFERENCE EXAMPLE 16

Synthesis of 4-hydroxyadamantane-1-acetate

To a solution of 4-oxoadamantan-1-ol (2.0 g) in chloroform (20 ml), acetic anhydride (1.3 ml) and 4-dimethylaminopyridine (1.6 g) were added and stirred at 50° C. for 2 hours. After distilling off the solvent under reduced pressure, the residue was diluted with water and extracted with ethyl acetate. The extracted organic layer was washed with brine and dried over anhydrous magnesium sulfate. After the desiccant was filtered off, the solvent was distilled off under reduced pressure to give 4-oxoadamantane-1-acetate (2.3 g) as a colorless powder.

To a solution of 4-oxoadamantane-1-acetate thus obtained (2.3 g) in ethanol (20 ml), sodium borohydride (0.63 g) was added under ice cooling and stirred at the same temperature for 1 hour. The reaction mixture was concentrated, diluted with ethyl acetate, washed sequentially with saturated aqueous ammonium chloride and brine, and then dried over anhydrous magnesium sulfate. The desiccant was filtered off and the solvent was distilled off under reduced pressure to give the titled compound, i.e., 4-hydroxyadamantane-1-acetate (2.3 g) as a colorless powder.

1H NMR (300 MHz, CHLOROFORM-D) δ 1.22-1.50 (m, 1 H), 1.53-1.83 (m, 3 H), 1.89-2.22 (m, 12 H), 2.30-2.40 (m, 1 H), 3.75 (s, 0.4 H), 3.94 (s, 0.6 H).

REFERENCE EXAMPLE 17

Synthesis of 4-hydroxyadamantane-1-benzoate

To a solution of 4-oxoadamantan-1-ol (5.0 g) in pyridine (20 ml), benzoyl chloride (4.2 ml) was added under ice cooling. The reaction mixture was then warmed to room temperature and stirred for 3 days. The reaction mixture was diluted with 1.2 M aqueous hydrochloric acid and extracted with chloroform. The extracted organic layer was washed with brine, dried over anhydrous magnesium sulfate and then filtered to remove the desiccant, followed by distilling off the solvent under reduced pressure to give 4-oxoadamantane-1-benzoate (8.3 g) as a yellow powder.

To a solution of the product thus obtained (8.1 g) in ethanol (100 ml), sodium borohydride (1.7 g) was added under ice cooling and stirred at the same temperature for 1.5 hours. The reaction mixture was concentrated, diluted with ethyl acetate, washed sequentially with saturated aqueous ammonium chloride and brine, dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=1:1) to give the titled compound, i.e., 4-hydroxyadamantane-1-benzoate (6.7 g) as a colorless powder.

1H NMR (300 MHz, CHLOROFORM-D) δ 1.44-1.72 (m, 2 H), 1.77-1.90 (m, 1 H), 2.01-2.37 (m, 10 H), 2.42-2.60 (m, 1 H), 3.80 (t, J=3.1 Hz, 0.4 H), 4.01 (t, J=3.1 Hz, 0.6 H), 7.33-7.47 (m, 2 H), 7.47-7.59 (m, 1 H), 7.94-8.04 (m, 2 H).

REFERENCE EXAMPLE 18

Synthesis of
6-fluoro-3,4-dihydro-2H-1,4-benzoxazine

To a solution of 6-fluoro-2H-1,4-benzoxazin-3(4H)-one (1.5 g) in tetrahydrofuran (30 ml), lithium aluminum hydride (683 mg) was added under ice cooling and heated under reflux for 3.5 hours. The reaction mixture was cooled to room temperature, diluted with 28% aqueous ammonia under ice cooling, and then filtered to remove insoluble materials. The filtrate was evaporated under reduced pressure to remove the solvent. The resulting residue was purified by silica gel column chromatography (eluting solvent: n-hexane:ethyl acetate=20:1 to 5:1) to give the titled compound, i.e., 6-fluoro-3,4-dihydro-2H-1,4-benzoxazine (1.35 g) as a red oil.

1H NMR (300 MHz, CHLOROFORM-D) δ 3.38-3.44 (m, 2 H), 3.83 (brs, 1 H), 4.18-4.23 (m, 2 H), 6.26-6.36 (m, 2 H), 6.64-6.72 (m, 1 H).

REFERENCE EXAMPLE 19

Synthesis of
7-fluoro-3,4-dihydro-2H-1,4-benzoxazine

To a solution of 5-fluoro-2-nitrophenol (9.50 g) in methanol (10 ml), 5% palladium on activated carbon (1.90 g) was added and stirred overnight under a hydrogen atmosphere at room temperature. The catalyst was filtered off and the solvent was distilled off under reduced pressure. The resulting residue was converted into a powder form by addition of chloroform, and then collected by filtration to give 2-amino-5-fluorophenol (6.81 g) as a brown powder. To a solution of 2-amino-5-fluorophenol thus obtained (3.00 g) in N,N-dimethylformamide (20 ml), potassium carbonate (16.31 g) and 1,2-dibromoethane (3.05 ml) were added and stirred at 125° C. for 10 hours. The reaction mixture was allowed to stand overnight at room temperature, to which additional 1,2-dibromoethane (1.52 ml) was then added and stirred at 125° C. for 7 hours. After cooling at room temperature, the reaction mixture was diluted with water under ice cooling and extracted with ethyl acetate. The organic layer was washed sequentially with water and brine, dried over anhydrous sodium sulfate and then filtered to remove the desiccant, followed by distilling off the solvent under reduced pressure. The resulting residue was purified by NH silica gel column chromatography (eluting solvent: n-hexane:ethyl acetate=9:1 to 7:3) to give the titled compound, i.e., 7-fluoro-3,4-dihydro-2H-1,4-benzoxazine (1.15 g) as a red-brown oil.

1H NMR (300 MHz, CHLOROFORM-D) δ 3.35-3.42 (m, 2 H), 3.60 (brs, 1 H), 4.22-4.26 (m, 2 H), 6.44-6.56 (m, 3 H).

REFERENCE EXAMPLE 20

Synthesis of
7-methyl-3,4-dihydro-2H-1,4-benzoxazine

To a solution of 2-amino-5-methylphenol (5.0 g) in N,N-dimethylformamide (50 ml), potassium carbonate (28.3 g) and 1,2-dibromoethane (10.6 ml) were added and stirred at 130° C. for 11 hours. After insoluble materials were filtered off, the filtrate was diluted with ethyl acetate and washed sequentially with water and brine. The organic layer was dried over anhydrous sodium sulfate and then filtered to remove the desiccant, followed by distilling off the solvent under reduced pressure. The resulting residue was purified by silica gel column chromatography (eluting solvent: n-hexane:ethyl acetate=20:1 to 9:1) to give the titled compound, i.e., 7-methyl-3,4-dihydro-2H-1,4-benzoxazine (980 mg) as a brown oil.

1H NMR (300 MHz, CHLOROFORM-D) δ 2.21 (s, 3 H), 3.36-3.43 (m, 2 H), 3.59 (brs, 1 H), 4.20-4.27 (m, 2 H), 6.48-6.63 (m, 3 H).

REFERENCE EXAMPLE 21

Synthesis of
5-methyl-3,4-dihydro-2H-1,4-benzoxazine

To a solution of 2-amino-m-cresol (5.0 g) in N,N-dimethylformamide (50 ml), potassium carbonate (28.3 g) and 1,2-dibromoethane (5.3 ml) were added and stirred at 130° C. for 4 hours and then stirred overnight at room temperature. To the reaction mixture, 1,2-dibromoethane (5.3 ml) was added and stirred at 130° C. for 6 hours. After addition of additional 1,2-dibromoethane (3.5 ml), the reaction mixture was stirred at 130° C. for 5 hours and then stirred overnight at room temperature. After insoluble materials were filtered off, the filtrate was diluted with ethyl acetate and washed sequentially with water and brine. The organic layer was dried over anhydrous sodium sulfate and then filtered to remove the desiccant, followed by distilling off the solvent under reduced pressure. The resulting residue was purified by silica gel column chromatography (eluting solvent: n-hexane:ethyl acetate=20:1 to 10:1) to give the titled compound, i.e., 5-methyl-3,4-dihydro-2H-1,4-benzoxazine (2.69 g) as a brown oil.

1H NMR (300 MHz, CHLOROFORM-D) δ 2.12 (s, 3 H), 3.42-3.63 (m, 3 H), 4.19-4.29 (m, 2 H), 6.54-6.73 (m, 3 H).

REFERENCE EXAMPLE 22

Synthesis of methyl
3,4-dihydro-2H-1,4-benzoxazine-6-carboxylate

To a solution of 4-hydroxy-3-nitrobenzoic acid (10.0 g) in methanol (100 ml), concentrated sulfuric acid (1 ml) was added and stirred at 80° C. for 19.5 hours. After the reaction mixture was concentrated, saturated aqueous sodium bicarbonate and ethyl acetate were added to the resulting residue. This mixture was stirred and the aqueous layer was then separated. The separated aqueous layer was diluted with 1M aqueous hydrochloric acid and extracted with ethyl acetate. The organic layer was washed sequentially with water and brine, and then dried over anhydrous sodium sulfate. After the desiccant was filtered off, the solvent was distilled off under reduced pressure to give methyl 4-hydroxy-3-nitrobenzoate (10.9 g) as a yellow solid. To a solution of methyl 4-hydroxy-3-nitrobenzoate thus obtained (10.9 g) in tetrahydrofuran:methanol (1:1, 100 ml), 10% palladium on activated carbon (550 mg) was added and stirred overnight under a hydrogen atmosphere at room temperature. After the reaction mixture was filtered through celite, the solvent was distilled off under reduced pressure to give methyl 3-amino-4-hydroxybenzoate (9.1 g) as a light-brown solid. To a solution of methyl 3-amino-4-hydroxybenzoate thus obtained (9.1 g) in N,N-dimethylformamide (80 ml), potassium carbonate (37.3 g) and 1,2-dibromoethane (14 ml) were added and stirred at 130° C. for 2 hours and then stirred overnight at room temperature. After insoluble materials were filtered off, the filtrate was diluted with ethyl acetate and washed with water. The organic layer was extracted with 6M aqueous hydrochloric acid, and the resulting aqueous layer was diluted with 8M aqueous sodium hydroxide and extracted with ethyl acetate.

The organic layer was dried over anhydrous sodium sulfate and then filtered to remove the desiccant, followed by distilling off the solvent under reduced pressure. The resulting residue was purified by silica gel column chromatography (eluting solvent: n-hexane:ethyl acetate=10:1 to 5:1) to give the titled compound, i.e., methyl 3,4-dihydro-2H-1,4-benzoxazine-6-carboxylate (7.10 g) as a pink solid.

1H NMR (300 MHz, CHLOROFORM-D) δ 3.39-3.47 (m, 2 H), 3.82-3.89 (m, 4 H), 4.26-4.34 (m, 2 H), 6.78 (d, J=8.4 Hz, 1 H), 7.29 (d, J=2.0 Hz, 1 H), 7.37 (dd, J=8.4, 2.0 Hz, 1 H).

REFERENCE EXAMPLE 23

Synthesis of 6-nitro-3,4-dihydro-2H-1,4-benzoxazine hydrochloride

To a solution of 2-amino-4-nitrophenol (2.0 g) in N,N-dimethylformamide (50 ml), potassium carbonate (9.0 g) and 1,2-dibromoethane (3.4 ml) were added and stirred at 130° C. for 10 hours. The reaction mixture was diluted with water and extracted with ethyl acetate. The extracted organic layer was washed with brine, dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=4:1). The resulting orange-colored powder was dissolved in ethyl acetate, diluted with 4M hydrochloric acid (in ethyl acetate) and stirred at room temperature for 1 hour. The precipitated solid was collected by filtration and dried by heating under reduced pressure to give the titled compound, i.e., 6-nitro-3,4-dihydro-2H-1,4-benzoxazine hydrochloride (1.0 g) as a light-brown powder.

1H NMR (300 MHz, DMSO-D6) δ 3.30-3.37 (m, 2 H), 4.20-4.27 (m, 2 H), 6.83 (d, J=8.7 Hz, 1 H), 7.40 (dd, J=8.7, 2.8 Hz, 1 H), 7.46 (d, J=2.8 Hz, 1 H).

REFERENCE EXAMPLE 24

Synthesis of 6-(trifluoromethyl)-3,4-dihydro-2H-1,4-benzoxazine

To a solution of 4-hydroxy-3-nitrobenzotrifluoride (1.00 g) in tetrahydrofuran (20 ml), 10% palladium on activated carbon (100 mg) was added and stirred overnight under a hydrogen atmosphere at room temperature. After the reaction mixture was filtered through celite, the solvent was distilled off under reduced pressure to give 2-amino-4-(trifluoromethyl)phenol (780 mg) as a gray powder.

To a solution of 2-amino-4-(trifluoromethyl)phenol thus obtained (780 mg) in ethyl acetate (8 ml), water (8 ml) and sodium bicarbonate (739 mg) were added under ice cooling, followed by dropwise addition of chloroacetyl chloride (0.42 ml). After stirring at room temperature for 3 days, the reaction mixture was diluted with water and extracted with ethyl acetate. The organic layer was washed with brine and then dried over anhydrous sodium sulfate. After the desiccant was filtered off, the solvent was distilled off under reduced pressure. The resulting residue was converted into a powder form by addition of chloroform and n-hexane, and then collected by filtration to give 2-chloro-N-[2-hydroxyphenyl-5-(trifluoromethyl)phenyl]acetamide (1.00 g) as a light-brown powder.

To a solution of 2-chloro-N-[2-hydroxyphenyl-5-(trifluoromethyl)phenyl]acetamide thus obtained (1.00 g) in N,N-dimethylformamide (15 ml), potassium carbonate (708 mg) was added and stirred at room temperature for 2 hours. After insoluble materials were filtered off, the filtrate was diluted with ethyl acetate and the organic layer was washed twice with water. The resulting organic layer was washed with brine and then dried over anhydrous sodium sulfate. After the desiccant was filtered off, the solvent was distilled off under reduced pressure to give 6-(trifluoromethyl)-2H-1,4-benzoxazin-3(4H)-one (860 mg) as a colorless powder.

To a solution of 6-(trifluoromethyl)-2H-1,4-benzoxazin-3(4H)-one thus obtained (860 mg) in tetrahydrofuran (5 ml), borane-tetrahydrofuran complex (1.03M in tetrahydrofuran, 7.7 ml) was added and heated under reflux for 3.5 hours. After the reaction mixture was diluted with methanol and heated under reflux for 1 hour, 1M aqueous hydrochloric acid was added and heated under reflux for an additional 30 minutes. The reaction mixture was cooled to room temperature, followed by distilling off the solvent under reduced pressure. The resulting residue was diluted with saturated aqueous sodium bicarbonate and extracted with ethyl acetate. The organic layer was washed sequentially with water and brine, dried over anhydrous sodium sulfate and then filtered to remove the desiccant, followed by distilling off the solvent under reduced pressure. The resulting residue was purified by silica gel column chromatography (eluting solvent: n-hexane:ethyl acetate=20:1 to 10:1) to give the titled compound, i.e., 6-(trifluoromethyl)-3,4-dihydro-2H-1,4-benzoxazine (730 mg) as a colorless powder.

1H NMR (300 MHz, CHLOROFORM-D) δ 3.41-3.48 (m, 2 H), 3.90 (brs, 1 H), 4.25-4.31 (m, 2 H), 6.79-6.85 (m, 2 H), 6.87-6.93 (m, 1 H).

REFERENCE EXAMPLE 25

Synthesis of 3,4-dihydro-2H-1,4-benzothiazine

To a solution of 2-aminothiophenol (5.01 g) in ethyl acetate (20 ml), 1,2-dibromoethane (4.14 ml) was added and stirred while heating at 60° C. under a nitrogen atmosphere. To the reaction mixture, triethylamine (9.72 ml) was added dropwise over 30 minutes and stirred at 60° C. for 10 hours. The reaction mixture was allowed to stand overnight at room temperature and then filtered to remove insoluble materials. The filtrate was washed sequentially with water and brine, dried over anhydrous sodium sulfate and then filtered to remove the desiccant, followed by distilling off the solvent under reduced pressure. The resulting residue was purified by silica gel column chromatography (eluting solvent: n-hexane:ethyl acetate=9:1 to 3:1) to give the titled compound, i.e., 3,4-dihydro-2H-1,4-benzothiazine (3.69 g) as a red-brown oil.

1H NMR (300 MHz, CHLOROFORM-D) δ 3.03-3.08 (m, 2 H), 3.60-3.65 (m, 2 H), 6.46 (dd, J=8.1, 1.3 Hz, 1 H), 6.61 (ddd, J=7.7, 7.1, 1.3 Hz, 1 H), 6.88 (ddd, J=8.1, 7.1, 1.6 Hz, 1 H), 6.98 (dd, J=7.7, 1.6 Hz, 1 H).

REFERENCE EXAMPLE 26

Synthesis of 1,2,3,4-tetrahydroquinoxaline

Under a nitrogen atmosphere, to a solution of lithium borohydride (741 mg) in tetrahydrofuran (50 ml), methyl iodide (1.93 ml) was added dropwise under ice cooling and stirred at room temperature for 10 minutes. To this mixture, a solution of quinoxaline (1.32 g) in tetrahydrofuran (100 ml) was added dropwise over 15 minutes and then stirred at room temperature for 5 minutes. To the reaction mixture, methanol (10 ml) was added and stirred for 5 minutes, followed by addition of additional methanol (40 ml) and stirring at room temperature for 30 minutes. After the reaction mixture was concentrated, the resulting residue was dissolved again in methanol and evaporated under reduced pressure to remove the solvent. The resulting residue was diluted with 4M aqueous sodium hydroxide (100 ml) and extracted four times with chloroform. The combined organic layers were dried over anhydrous sodium sulfate and then filtered to remove the desiccant, followed by distilling off the solvent under reduced pressure. The resulting residue was converted into a powder form by addition of n-hexane, and then collected by filtration to give the titled compound, i.e., 1,2,3,4-tetrahydroquinoxaline (1.17 g) as a light-brown crystal.

1H NMR (300 MHz, CHLOROFORM-D) δ 3.42 (s, 4 H), 6.45-6.53 (m, 2 H), 6.55-6.62 (m, 2 H).

REFERENCE EXAMPLE 27

Synthesis of 1-acetyl-1,2,3,4-tetrahydroquinoxaline

To a solution of 1,2,3,4-tetrahydroquinoxaline obtained in Reference Example 26 (360 mg) in ethanol (10 ml), acetic anhydride (254 μl) was added dropwise under ice cooling and stirred at room temperature for 10 minutes. The reaction mixture was diluted with 1M aqueous sodium hydroxide (10 ml) and extracted with chloroform. The organic layer was washed with brine and dried over anhydrous sodium sulfate. The desiccant was filtered off and the solvent was distilled off under reduced pressure to give the titled compound, i.e., 1-acetyl-1,2,3,4-tetrahydroquinoxaline (494 mg) as a brown oil.

1H NMR (300 MHz, CHLOROFORM-D) δ 2.27 (s, 3 H), 3.40-3.50 (m, 2 H), 3.80-3.90 (m, 2 H), 4.06 (brs, 1 H), 6.55-6.71 (m, 2 H), 6.91-7.06 (m, 2 H).

REFERENCE EXAMPLE 28

Synthesis of tert-butyl 3,4-dihydroquinoxaline-1(2H)-carboxylate

To a solution of 1,2,3,4-tetrahydroquinoxaline obtained in Reference Example 26 (1.15 g) in tetrahydrofuran (80 ml), 1M sodium hydroxide (8 ml) was added and di-tert-butyl dicarbonate (1.87 g) was then added under ice cooling. The reaction mixture was stirred overnight at room temperature and filtered to remove insoluble materials, followed by distilling off the solvent under reduced pressure. The resulting residue was purified by silica gel column chromatography (eluting solvent: n-hexane:ethyl acetate=9:1 to 5:1) to give the titled compound, i.e., tert-butyl 3,4-dihydroquinoxaline-1(2H)-carboxylate (2.69 g) as a yellow oil.

1H NMR (300 MHz, CHLOROFORM-D) δ 1.52 (s, 9 H), 3.36-3.50 (m, 2 H), 3.70-3.81 (m, 2 H), 3.95 (brs, 1 H), 6.56 (dd, J=7.8, 1.4 Hz, 1 H), 6.65 (dd, J=7.8, 1.5 Hz, 1 H), 6.82-6.94 (m, 1 H), 7.49 (d, J=7.9 Hz, 1 H).

REFERENCE EXAMPLE 29

Synthesis of 1-methyl-1,2,3,4-tetrahydroquinoxaline

To a solution of tert-butyl 3,4-dihydroquinoxaline-1(2H)-carboxylate obtained in Reference Example 28 (1.06 g) in tetrahydrofuran (20 ml), sodium hydride (60% suspension in oil, 181 mg) was added and stirred for 5 minutes, followed by addition of methyl iodide (281 μl). After stirring at room temperature for 1 hour, sodium hydride (60% suspension in oil, 181 mg) was further added and stirred for 30 minutes, followed by addition of methyl iodide (281 μl). After stirring overnight at room temperature, the reaction mixture was diluted with water and extracted with ethyl acetate. The organic layer was washed sequentially with water and brine, and then dried over anhydrous sodium sulfate. After the desiccant was filtered off, the solvent was distilled off under reduced pressure and the resulting residue was purified by silica gel column chromatography (eluting solvent: n-hexane: ethyl acetate=10:1 to 5:1) to give tert-butyl 4-methyl-3,4-dihydroquinoxaline-1(2H)-carboxylate (331 mg) as a brown powder. To a solution of tert-butyl 4-methyl-3,4-dihydroquinoxaline-1(2H)-carboxylate thus obtained (331 mg) in ethyl acetate (2 ml), 4N hydrochloric acid (in ethyl acetate, 1.1 ml) was added and stirred overnight at room temperature. The reaction mixture was diluted with 8M aqueous sodium hydroxide and then extracted with ethyl acetate. The organic layer was washed with brine and then dried over anhydrous sodium sulfate. After the desiccant was filtered off, the solvent was distilled off under reduced pressure to give the titled compound, i.e., 1-methyl-1,2,3,4-tetrahydroquinoxaline (179 mg) as a brown oil.

1H NMR (300 MHz, CHLOROFORM-D) δ 2.86 (s, 3 H), 3.23-3.31 (m, 2 H), 3.44-3.52 (m, 2 H), 3.68 (brs, 1 H), 6.43-6.51 (m, 1 H), 6.53-6.62 (m, 2 H), 6.63-6.72 (m, 1 H).

REFERENCE EXAMPLE 30

Synthesis of E-4-aminoadamantane-1-carboxamide

To a solution of methyl 4-aminoadamantane-1-carboxylate obtained in Reference Example 11 (1.87 g) in tetrahydrofuran (20 ml), water (10 ml), benzyl chloroformate (1.53 g) and sodium carbonate (1.13 g) were added and stirred at room temperature for 5 hours. Benzyl chloroformate (0.76 g) was further added and stirred at room temperature for 2 hours. After insoluble materials were filtered off, the solvent was concentrated and the residue was extracted with chloroform. The organic layer was dried over anhydrous sodium sulfate and then filtered to remove the desiccant, followed by distilling off the solvent under reduced pressure. The resulting residue was purified by silica gel column chromatography (eluting solvent: chloroform:methanol=200:1 to 100:1) to give methyl 4-{[2-(benzyloxy)-2-oxoethyl]amino}-adamantane-1-carboxylate (3.30 g) as a colorless powder.

To a suspension of methyl 4-{[2-(benzyloxy)-2-oxoethyl] amino}-adamantane-1-carboxylate thus obtained (3.30 g) in tetrahydrofuran (20 ml), methanol (10 ml) and 8M aqueous sodium hydroxide (10 ml) were added and stirred at room temperature for 3 hours. After the reaction mixture was concentrated, the resulting residue was diluted with 1M aqueous sodium hydroxide and washed with diethyl ether. The resulting aqueous layer was diluted with 12M aqueous hydrochloric acid and extracted with chloroform. The organic layer was washed with brine and then dried over anhydrous sodium sulfate. After the desiccant was filtered off, the solvent was distilled off under reduced pressure to give 4-{[2-(benzyloxy)-2-oxoethyl]amino}-adamantane-1-carboxylic acid (2.95 g) as a light-brown viscous substance.

To a solution of 4-{[2-(benzyloxy)-2-oxoethyl]amino}-adamantane-1-carboxylic acid thus obtained (2.95 g) in chloroform (80 ml), N,N-diisopropylethylamine (4.7 ml), 1-hydroxybenzotriazole monohydrate (2.05 g) and 1-ethyl-3-(3-dimethylaminopropyl)carbodiimide hydrochloride (2.57 g) were added and stirred at room temperature for 1 hour. To the reaction mixture, ammonia (8M in methanol, 3.4 ml) was added and stirred overnight at room temperature. After insoluble materials were filtered off, the organic layer was washed sequentially with water, 1M aqueous hydrochloric acid, saturated aqueous sodium bicarbonate and brine. After the organic layer was concentrated, the precipitated crystal was collected by filtration and washed with ethyl acetate to give benzyl Z—N-(5-carbamoyladamantan-2-yl)glycinate (820 mg). The filtrate was concentrated, and the resulting residue was purified by silica gel column chromatography (eluting solvent: n-hexane:ethyl acetate=1:1 to 1:3) to give benzyl E-N-(5-carbamoyladamantan-2-yl)glycinate (1.17 g) as a colorless powder.

To a solution of E-benzyl N-(5-carbamoyladamantan-2-yl) glycinate thus obtained (1.17 g) in methanol (40 ml), 10% palladium on activated carbon (100 mg) was added and stirred overnight under a hydrogen atmosphere at room temperature. After the reaction mixture was filtered through celite, the solvent was distilled off under reduced pressure to give the titled compound, i.e., E-4-aminoadamantane-1-carboxamide (700 mg) as a colorless powder.

The product was confirmed to be E-form by X-ray crystal structure analysis on the crystal obtained separately by recrystallization from methanol.

1H NMR (300 MHz, DMSO-D6) δ 1.38-1.50 (m, 2 H), 1.68-2.03 (m, 12 H), 6.75 (brs, 1 H), 7.00 (brs, 1 H).

REFERENCE EXAMPLE 31

S-{E-4-[(Benzyloxy)carbonylamino]adamantan-1-yl}ethanethioate

To a suspension of E-4-aminoadamantan-1-ol hydrochloride obtained in Reference Example 1 (5.0 g) in tetrahydrofuran (100 ml), sodium carbonate (13 g) was added and stirred for 30 minutes. To this mixture, benzyloxycarbonyl chloride (4.2 ml) was added at room temperature and stirred for 15 hours. The reaction mixture was diluted with water and extracted with ethyl acetate. The extracted organic layer was washed with brine, dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=1:1) to give benzyl (E-5-hydroxyadamantan-2-yl)carbamate (4.1 g) as a colorless oil.

To a solution of benzyl (E-5-hydroxyadamantan-2-yl)carbamate thus obtained (4.1 g) in chloroform (50 ml), triethylamine (4.7 ml) and methanesulfonyl chloride (1.8 ml) were added at room temperature and stirred for 2 hours. The reaction mixture was diluted with ethyl acetate, washed with water and brine, dried over anhydrous magnesium sulfate and then filtered to remove the desiccant, followed by distilling off the solvent under reduced pressure. To the resulting residue, thioacetic acid (20 ml) was added and stirred at 100° C. for 9 hours. The reaction mixture was neutralized with saturated aqueous sodium bicarbonate under ice cooling and extracted with ethyl acetate. The extracted organic layer was washed with brine, dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=9:1) to give the titled compound, i.e., S-{E-4-[(benzyloxy)carbonylamino]adamantan-1-yl}ethanethioate (2.2 g) as a light-brown oil.

1H NMR (300 MHz, CHLOROFORM-D) δ 1.50-1.82 (m, 4 H), 1.94-2.32 (m, 12 H), 3.80-3.94 (m, 1 H), 4.93-5.20 (m, 3 H), 7.29-7.41 (m, 5 H).

REFERENCE EXAMPLE 32

Synthesis of E-5-methylsulfonyladamantane-2-amine

To a solution of S-{E-4-[(benzyloxy)carbonylamino]adamantan-1-yl}ethanethioate obtained in Reference Example 31 (2.2 g) in methanol (40 ml), methyl iodide (0.57 ml) and sodium methoxide (1.3 g) were added at room temperature and stirred for 24 hours. The reaction mixture was diluted with water and extracted with ethyl acetate. The extracted organic layer was washed with brine, dried over anhydrous magnesium sulfate and then filtered to remove the desiccant, followed by distilling off the solvent under reduced pressure.

To a solution of the resulting residue in chloroform (50 ml), m-chloroperbenzoic acid (3.1 g) was added at room temperature and stirred for 3 days. The reaction mixture was diluted with chloroform, washed sequentially with saturated aqueous sodium bicarbonate and saturated aqueous disodium sulfite, dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=1:1) to give benzyl [E-5-(methylsulfonyl)adamantan-2-yl]carbamate (1.5 g) as a colorless powder. To a solution of the resulting colorless powder (1.5 g) in methanol (20 ml), palladium on carbon (0.2 g) was added and stirred at room temperature for 24 hours while purging with hydrogen. The reaction mixture was filtered through celite, and the solvent was distilled off under reduced pressure to give the titled compound, i.e., E-5-methylsulfonyladamantane-2-amine (0.63 g) as a colorless powder.

1H NMR (300 MHz, CHLOROFORM-D) δ 1.42-1.62 (m, 4 H), 1.92-2.26 (m, 11 H), 2.76 (s, 3 H), 3.01-3.09 (m, 1 H).

REFERENCE EXAMPLE 33

Synthesis of E-5-[2-(methylsulfonyl)ethoxy]adamantane-2-amine hydrochloride

To a suspension of E-4-aminoadamantan-1-ol obtained in Reference Example 2 (812 mg) in tetrahydrofuran (10 ml), di-tert-butyl dicarbonate (1.11 g) was added and stirred overnight at room temperature. After distilling off the solvent under reduced pressure, the resulting residue was converted into a powder form by addition of n-hexane, and then collected by filtration to give tert-butyl (E-5-hydroxyadamantan-2-yl)carbamate (1.19 g) as a colorless powder. To a solution of tert-butyl (E-5-hydroxyadamantan-2-yl)carbamate thus obtained (300 mg) in tetrahydrofuran (5 ml), sodium hydride (54 mg) and methyl vinyl sulfone (0.15 ml) were added and stirred at room temperature for 7.5 hours. The reaction mixture was diluted with water and extracted with ethyl acetate. The organic layer was washed sequentially with water and brine, and then dried over anhydrous sodium sulfate. The desiccant was filtered off and the solvent was distilled off under reduced pressure. The resulting residue was dissolved in ethyl acetate (10 ml), to which 4N hydrochloric acid (in ethyl acetate, 10 ml) was then added and stirred overnight at room temperature. The precipitate was collected by filtration and washed with ethyl acetate to give the titled compound, i.e., E-5-[2-(methylsulfonyl)ethoxy]adamantane-2-amine hydrochloride (314 mg) as a colorless powder.

1H NMR (300 MHz, DMSO-D$_6$) δ1.38-1.48 (m, 2 H), 1.70-1.98 (m, 8 H), 2.05-2.20 (m, 3 H), 2.98 (s, 3 H), 3.24-3.42 (m, 3 H), 3.73 (t, J=5.6 Hz, 2 H), 8.04-8.21 (m, 2 H).

REFERENCE EXAMPLE 34

Synthesis of 5-benzyloxyadamantan-2-ol

To a solution of 4-oxoadamantan-1-ol (5.0 g) in N,N-dimethylformamide (50 ml), sodium hydride (60%, 1.4 g) and benzyl bromide (3.9 ml) were added under ice cooling. The reaction mixture was then warmed to room temperature and stirred for 1 hour. The reaction mixture was diluted with saturated aqueous ammonium chloride under ice cooling and extracted with ethyl acetate. The extracted organic layer was washed with brine, dried over anhydrous magnesium sulfate and then filtered to remove the desiccant, followed by distilling off the solvent under reduced pressure to give 5-benzyloxyadamantan-2-one (8g) as a colorless oil.

To a solution of the compound thus obtained (7.7 g) in ethanol (100 ml), sodium borohydride (1.7 g) was added under ice cooling and stirred at the same temperature for 15 minutes. The reaction mixture was concentrated, diluted with saturated aqueous ammonium chloride and then extracted with ethyl acetate. The extracted organic layer was washed with brine, dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=4:1) to give the titled compound, i.e., 5-benzyloxyadamantan-2-ol (4.5 g) as a colorless powder.

1H NMR (300 MHz, CHLOROFORM-D) δ 1.36-1.48 (m, 1 H), 1.52-1.96 (m, 8 H), 1.99-2.28 (m, 5 H), 3.76 (m, 0.4 H), 3.92 (m, 0.6 H), 4.46-4.58 (m, 2 H), 7.18-7.38 (m, 5 H).

EXAMPLE A-1

Synthesis of N-[E-1-hydroxyadamantan-4-yl]-3,4-dihydroquinoline-1(2H)-carboxamide (Compound A-1)

To a solution of E-4-aminoadamantan-1-ol obtained in Reference Example 2 (300 mg) in a mixture of chloroform (5 ml) and N,N-dimethylformamide (5 ml), N,N'-carbonyldiimidazole (400 mg) was added and stirred at room temperature for 1 hour. To the reaction mixture, a solution of triethylamine (0.31 ml) and 1,2,3,4-tetrahydroquinoline (440 mg) in chloroform (5 ml) was then added and the resulting mixture was heated to reflux and stirred for 6 hours. After cooling at room temperature, the reaction mixture was washed sequentially with 1.2M hydrochloric acid and brine. The organic layer was dried over anhydrous magnesium sulfate and then filtered to remove the desiccant, followed by distilling off the solvent under reduced pressure. The resulting residue was purified by silica gel column chromatography (eluting solvent: chloroform:methanol=49:1) to give the titled compound (295 mg) as a colorless solid.

1H NMR (300 MHz, CHLOROFORM-D) δ 1.36-1.63 (m, 4 H), 1.68-1.81 (m, 4 H), 1.84-1.99 (m, 4 H), 2.03-2.23 (m, 3 H), 2.77 (t, J=6.7 Hz, 2 H), 3.72-3.80 (m, 2 H), 3.92-4.00 (m, 1 H), 5.41 (d, J=8.2 Hz, 1 H), 6.99-7.12 (m, 1 H), 7.19 (m, 2 H), 7.29-7.37 (m, 1 H).

EXAMPLE A-2

Synthesis of 6-chloro-N-[E-1-hydroxyadamantan-4-yl]-3,4-dihydroquinoline-1(2H)-carboxamide (Compound A-2)

To a solution of E-4-aminoadamantan-1-ol obtained in Reference Example 2 (225 mg) in a mixture of chloroform (5 ml) and N,N-dimethylformamide (3 ml), N,N'-carbonyldiimidazole (241 mg) was added and stirred at room temperature for 1 hour. To the reaction mixture, a solution of triethylamine (0.23 ml) and 6-chloro-1,2,3,4-tetrahydroquinoline (260 mg) in chloroform (3 ml) was then added and the resulting mixture was heated to reflux and stirred for 8 hours. After cooling at room temperature, the reaction mixture was diluted with ethyl acetate and washed sequentially with 1.2M hydrochloric acid and brine. The organic layer was dried over anhydrous magnesium sulfate and then filtered to remove the desiccant, followed by distilling off the solvent under reduced pressure. The resulting residue was purified by silica gel column chromatography (eluting solvent: chloroform:methanol=19:1) to give the titled compound (170 mg) as a light-yellow powder.

1H NMR (300 MHz, CHLOROFORM-D) δ 1.36-1.63 (m, 4 H), 1.67-1.81 (m, 4 H), 1.83-2.00 (m, 4 H), 2.04-2.23 (m, 3 H), 2.74 (t, J=6.7 Hz, 2 H), 3.68-3.78 (m, 2 H), 3.88-4.07 (m, 1 H), 5.26 (d, J=6.37 Hz, 1 H), 7.10-7.21 (m, 2 H), 7.24-7.35 (m, 1 H).

EXAMPLE A-3

Synthesis of 6-methyl-N-[E-1-hydroxyadamantan-4-yl]-3,4-dihydroquinoline-1(2H)-carboxamide (Compound A-3)

E-4-Aminoadamantan-1-ol (0.12 g) was suspended in chloroform (3.0 ml) and N,N-dimethylformamide (2.0 ml), to which N,N'-carbonyldiimidazole (0.12 g) was then added at room temperature and stirred for 1 hour. Further, 6-methyl-1,2,3,4-tetrahydroquinoline (0.12 ml) and triethylamine (0.12 ml) were added and heated under reflux for 8 hours. The reaction mixture was added dropwise to 1M aqueous hydrochloric acid (30 ml), extracted with ethyl acetate, and then washed with water, saturated aqueous sodium bicarbonate and brine. After drying over anhydrous magnesium sulfate, the desiccant was filtered off and the solvent was distilled off under reduced pressure. The resulting residue was purified by silica gel column chromatography (eluting solvent: n-hexane:ethyl acetate=1:1→ethyl acetate alone) to give the titled compound (0.16 g) as a colorless powder.

1H NMR (300 MHz, CHLOROFORM-D) δ 1.40-1.59 (m, 5 H), 1.69-1.78 (m, 4 H), 1.84-1.95 (m, 4 H), 2.06-2.16 (m, 3 H), 2.31 (s, 3 H), 2.72 (t, J=6.7 Hz, 2 H), 3.70-3.78 (m, 2 H), 3.92-3.98 (m, 1 H), 5.37-5.43 (m, 1 H), 6.98-7.03 (m, 2 H), 7.18-7.23 (m, 1 H).

EXAMPLE A-4

Synthesis of 6-methoxy-N—[E-1-hydroxyadamantan-4-yl]-3,4-dihydroquinoline-1(2H)-carboxamide (Compound A-4)

E-4-Aminoadamantan-1-ol (0.12 g) was suspended in chloroform (3.0 ml) and N,N-dimethylformamide (2.0 ml), to which N,N'-carbonyldiimidazole (0.12 g) was then added at room temperature and stirred for 1 hour. Further, 6-methoxy-1,2,3,4-tetrahydroquinoline (0.12 ml) and triethylamine (0.12 ml) were added and heated under reflux for 8 hours. The reaction mixture was added dropwise to 1M aqueous hydrochloric acid (30 ml), extracted with ethyl acetate, and then washed with water, saturated aqueous sodium bicarbonate and brine. After drying over anhydrous magnesium sulfate, the desiccant was filtered off and the solvent was distilled off under reduced pressure. The resulting residue was purified by silica gel column chromatography (eluting solvent: n-hexane:

ethyl acetate=1:1→ethyl acetate alone) to give the titled compound (0.16 g) as a colorless powder.

1H NMR (300 MHz, CHLOROFORM-D) δ 1.38-1.57 (m, 5 H), 1.67-1.78 (m, 4 H), 1.84-1.96 (m, 4 H), 2.05-2.15 (m, 3 H), 2.74 (t, J=6.8 Hz, 2 H), 3.69-3.77 (m, 2 H), 3.81 (s, 3 H), 3.90-3.98 (m, 1 H), 5.27-5.36 (m, 1 H), 6.71-6.79 (m, 2 H), 7.22 (d, J=8.70 Hz, 1 H).

EXAMPLE A-5

Synthesis of N-adamantan-2-yl-3,4-dihydroquinoline-1(2H)-carboxamide (Compound A-5)

To a suspension of 2-adamantaneamine hydrochloride (0.15 g) in chloroform (5.0 ml), triethylamine (0.28 ml) was added at room temperature and stirred for 5 minutes, followed by addition of N,N'-carbonyldiimidazole (0.14 g). After stirring for 1 hour, 1,2,3,4-tetrahydroquinoline (0.11 ml) was further added and heated under reflux for 7 hours. The reaction mixture was added dropwise to 1M aqueous hydrochloric acid (30 ml), extracted with ethyl acetate, and then washed with water, saturated aqueous sodium bicarbonate and brine. After drying over anhydrous magnesium sulfate, the desiccant was filtered off and the solvent was distilled off under reduced pressure. The resulting residue was purified by silica gel column chromatography (eluting solvent: n-hexane:ethyl acetate=9:1 to 3:1) to give the titled compound (0.19 g) as a colorless powder.

1H NMR (300 MHz, CHLOROFORM-D) δ 1.59-1.99 (m, 16 H), 2.76 (t, J=6.7 Hz, 2 H), 3.73-3.80 (m, 2 H), 3.96-4.03 (m, 1 H), 5.49-5.58 (m, 1 H), 7.01-7.08 (m, 1 H), 7.14-7.23 (m, 2 H), 7.33-7.38 (m, 1 H).

EXAMPLE A-6

Synthesis of N—[E-1-hydroxyadamantan-4-yl]-2,3-dihydro-1H-indole-1-carboxamide (Compound A-6)

To a solution of E-4-aminoadamantan-1-ol obtained in Reference Example 2 (100 mg) in a mixture of chloroform (5 ml) and N,N-dimethylformamide (2 ml), N-methylmorpholine (0.12 ml) and N,N'-carbonyldiimidazole (180 mg) were added and stirred at room temperature for 1 hour. To the reaction mixture, a solution of indoline (176 mg) in chloroform (2 ml) was then added and stirred at 60° C. for 2 hours. After cooling at room temperature, the reaction mixture was washed sequentially with 1.2M hydrochloric acid and brine. The organic layer was dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=1:1) to give the titled compound (30 mg) as a colorless solid.

1H NMR (300 MHz, CHLOROFORM-D) δ 1.45-1.62 (m, 4 H), 1.65-1.84 (m, 4 H), 1.87-2.01 (m, 2 H), 2.08-2.30 (m, 3 H), 3.19 (t, J=8.6 Hz, 2 H), 3.96 (t, J=8.6 Hz, 2 H), 4.01-4.12 (m, 1 H), 4.72-4.87 (m, 1 H), 6.84-6.95 (m, 1 H), 7.09-7.22 (m, 2 H), 7.74-7.91 (m, 1 H).

EXAMPLE A-7

Synthesis of N-[E-1-hydroxyadamantan-4-Y[1]-N-methyl-3,4-dihydroquinoline-1(2H)-carboxamide (Compound A-7)

To a solution of 1,2,3,4-tetrahydroquinoline (1.02 g) in tetrahydrofuran (40 ml), N,N'-carbonyldiimidazole was added and heated under reflux for 16 hours. The reaction mixture was concentrated, diluted with chloroform, washed sequentially with water and brine, dried over anhydrous sodium sulfate and then filtered to remove the desiccant, followed by distilling off the solvent under reduced pressure. The resulting residue was purified by silica gel column chromatography (eluting solvent: n-hexane:ethyl acetate=10:1 to 5:1) to give 1-(1H-imidazol-1-ylcarbonyl)-1,2,3,4-tetrahydroquinoline (510 mg) as a yellow oil. To a solution of 1-(1H-imidazol-1-ylcarbonyl)-1,2,3,4-tetrahydroquinoline thus obtained (510 mg) in acetonitrile (5 ml), methyl iodide (0.56 ml) was added and stirred overnight at room temperature. Methyl iodide (0.28 ml) was further added and stirred for 2 hours at room temperature and then at 50° C. for 30 minutes. After the reaction mixture was concentrated, the resulting residue was diluted with diethyl ether and the crystal was collected by filtration and dried to give 1-(3,4-dihydroquinolin-1(2H)-ylcarbonyl)-3-methyl-1H-imidazol-3-ium iodide (750 mg) as a light-yellow powder. To a solution of 1-(3,4-dihydroquinolin-1(2H)-ylcarbonyl)-3-methyl-1H-imidazol-3-ium iodide thus obtained (144 mg) in chloroform (5 ml), triethylamine (54 µl) and E-4-(methylamino)adamantan-1-ol (71 mg) were added and stirred overnight at room temperature, followed by stirring at 60° C. for 8 hours and then at 70° C. for 9 hours. The reaction mixture was diluted with 1M aqueous hydrochloric acid, extracted with chloroform, and then washed with brine. The organic layer was dried over anhydrous sodium sulfate and then filtered to remove the desiccant, followed by distilling off the solvent under reduced pressure. The resulting residue was purified by silica gel column chromatography (eluting solvent: n-hexane:ethyl acetate=1:1→chloroform:methanol=50:1) and then crystallized from hexane/diethyl ether to give the titled compound (20 mg) as a colorless powder.

1H NMR (300 MHz, CHLOROFORM-D) δ 1.44-1.54 (m, 3 H), 1.71-1.91 (m, 8 H), 1.92-2.02 (m, 2 H), 2.12-2.25 (m, 1 H), 2.51-2.62 (m, 2 H), 2.71-2.84 (m, 5 H), 3.63-3.70 (m, 2 H), 3.77 (brs, 1 H), 6.89-6.97 (m, 1 H), 7.03-7.17 (m, 2 H), 7.22-7.31 (m, 1 H).

EXAMPLE 1

Synthesis of 5-fluoro-N-(E-1-hydroxyadamantan-4-yl)-3,4-dihydroquinoline-1(2H)-carboxamide (Compound 1)

To a solution of E-4-aminoadamantan-1-ol hydrochloride obtained in Reference Example 1 (79 mg) in N,N-dimethylformamide (3 ml), triethylamine (0.13 ml) and N,N'-carbonyldiimidazole (69 mg) were added and stirred at room temperature for 1 hour. To the reaction mixture, a solution of 5-fluoro-1,2,3,4-tetrahydroquinoline obtained in Reference Example 4 (39 mg) in N,N-dimethylformamide (2 ml) was then added and heated to 120° C., followed by stirring for 8 hours. To the reaction mixture, N,N-dimethylaminopyridine (3 mg) was added and stirred at 120° C. for an additional 3 hours. After cooling at room temperature, the reaction mixture was poured into 1M aqueous hydrochloric acid and extracted with ethyl acetate. The extracted organic layer was washed sequentially with water, saturated aqueous sodium bicarbonate and brine. After drying over anhydrous magnesium sulfate, the desiccant was filtered off and the solvent was distilled off under reduced pressure. The resulting residue was purified by silica gel column chromatography (eluting solvent: chloroform:methanol=97:3 to 19:1) to give the titled compound (Compound 1, 17 mg) as a colorless powder.

1H NMR (300 MHz, CHLOROFORM-D) δ 1.25-1.55 (m, 5 H), 1.71-1.79 (m, 4 H), 1.85-1.97 (m, 4 H), 2.08-2.18 (m, 3 H), 2.75-2.82 (m, 2 H), 3.74-3.80 (m, 2 H), 3.93-4.00 (m, 1 H), 5.41-5.48 (m, 1 H), 6.77-6.84 (m, 1 H), 7.10-7.21 (m, 2 H).

EXAMPLE 2

Synthesis of 6-fluoro-N-(E-1-hydroxyadamantan-4-yl)-3,4-dihydroquinoline-1(2H)-carboxamide (Compound 2)

To a solution of N,N'-carbonyldiimidazole (185 mg) and triethylamine (159 μl) in chloroform (5 ml), E-4-aminoadamantan-1-ol obtained in Reference Example 2 (127 mg) and N,N-dimethylformamide (2 ml) were added and stirred at room temperature for 1 hour. To the reaction mixture, 6-fluoro-1,2,3,4-tetrahydroquinoline obtained in Reference Example 5 (172 mg) was added and heated under reflux for 5.5 hours, followed by stirring overnight at room temperature. The reaction mixture was then heated under reflux for an additional 8.5 hours. After cooling at room temperature, the reaction mixture was diluted with 1M aqueous hydrochloric acid and extracted with chloroform. After distilling off the solvent under reduced pressure, the residue was diluted with ethyl acetate and washed sequentially with water and brine. The organic layer was dried over anhydrous sodium sulfate and then filtered to remove the desiccant, followed by distilling off the solvent under reduced pressure. The resulting residue was converted into a powder form by addition of chloroform and diethyl ether, and the crystal was collected by filtration to give the titled compound (Compound 2, 140 mg) as a light-brown powder.

1H NMR (300 MHz, CHLOROFORM-D) δ 1.35-1.57 (m, 5 H), 1.67-1.80 (m, 4 H), 1.83-1.99 (m, 4 H), 2.05-2.17 (m, 3 H), 2.75 (t, J=6.7 Hz, 2 H), 3.69-3.77 (m, 2 H), 3.91-3.99 (m, 1 H), 5.24 (d, J=7.0 Hz, 1 H), 6.86-6.95 (m, 2 H), 7.25-7.32 (m, 1 H).

EXAMPLE 3

Synthesis of 7-fluoro-N-(E-1-hydroxyadamantan-4-yl)-3,4-dihydroquinoline-1(2H)-carboxamide (Compound 3)

To a solution of E-4-aminoadamantan-1-ol obtained in Reference Example 2 (391 mg) in a mixture of chloroform (5 ml) and N,N-dimethylformamide (5 ml), N,N'-carbonyldiimidazole (417 mg) was added and stirred at room temperature for 1 hour. To the reaction mixture, a solution of triethylamine (0.36 ml) and 7-fluoro-1,2,3,4-tetrahydroquinoline obtained in Reference Example 6 (530 mg) in chloroform (5 ml) was then added and heated under reflux for 3 hours, followed by stirring overnight at room temperature. The reaction mixture was then heated under reflux for an additional 5 hours. After cooling at room temperature, the reaction mixture was diluted with ethyl acetate and washed sequentially with 1.2M aqueous hydrochloric acid and brine. The organic layer was dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=1:1→chloroform:methanol=9:1) to give the titled compound (Compound 3, 250 mg) as a colorless powder.

1H NMR (300 MHz, CHLOROFORM-D) δ 1.41 (s, 1 H), 1.45-1.66 (m, 4 H), 1.70-1.81 (m, 4 H), 1.84-1.98 (m, 4 H), 2.08-2.21 (m, 3 H), 2.73 (t, J=6.7 Hz, 2 H), 3.72 (t, J=6.2 Hz, 2 H), 3.91-4.04 (m, 1 H), 5.35 (d, J=6.7 Hz, 1 H), 6.76 (td, J=8.3, 2.6 Hz, 1 H), 7.04-7.19 (m, 2 H).

EXAMPLE 4

Synthesis of 8-fluoro-N-(E-1-hydroxyadamantan-4-yl)-3,4-dihydroquinoline-1(2H)-carboxamide (Compound 4)

To a solution of N,N'-carbonyldiimidazole (219 mg) and triethylamine (188 μl) in chloroform (5 ml), E-4-aminoadamantan-1-ol obtained in Reference Example 2 (150 mg) and N,N-dimethylformamide (2 ml) were added and stirred at room temperature for 1 hour. To the reaction mixture, 8-fluoro-1,2,3,4-tetrahydroquinoline obtained in Reference Example 7 (204 mg) was added and heated under reflux for 5.5 hours, followed by stirring overnight at room temperature. The reaction mixture was then heated under reflux for an additional 6.5 hours. After addition of 4-dimethylaminopyridine (31 mg), the reaction mixture was heated under reflux for 3 hours and then stirred overnight at room temperature. The reaction mixture was diluted with 1M aqueous hydrochloric acid and extracted with chloroform. After distilling off the solvent under reduced pressure, the residue was diluted with ethyl acetate and washed sequentially with 1M aqueous hydrochloric acid, water:brine (1:1) and brine. The organic layer was dried over anhydrous sodium sulfate and then filtered to remove the desiccant, followed by distilling off the solvent under reduced pressure. The resulting residue was converted into a powder form by addition of diethyl ether and n-hexane, and the resulting crystal was collected by filtration and washed with diethyl ether to give the titled compound (Compound 4, 42 mg) as a colorless powder.

1H NMR (300 MHz, CHLOROFORM-D) δ 1.32-1.54 (m, 5 H), 1.67-1.79 (m, 4 H), 1.83-2.01 (m, 4 H), 2.03-2.18 (m, 3 H), 2.79 (t, J=6.8 Hz, 2 H), 3.73 (t, J=6.4 Hz, 2 H), 3.91-3.99 (m, 1 H), 4.95 (d, J=7.0 Hz, 1 H), 6.95-7.04 (m, 2 H), 7.06-7.14 (m, 1 H).

EXAMPLE 5

Synthesis of N-(E-1-hydroxyadamantan-4-yl)-7-methoxy-3,4-dihydroquinoline-1(2H)-carboxamide (Compound 5)

To a solution of N,N'-carbonyldiimidazole (219 mg) and triethylamine (188 μl) in chloroform (5 ml), E-4-aminoadamantan-1-ol obtained in Reference Example 2 (150 mg) and N,N-dimethylformamide (2 ml) were added and stirred at room temperature for 1 hour. To the reaction mixture, 7-methoxy-1,2,3,4-tetrahydroquinoline obtained in Reference Example 8 (220 mg) was added and heated under reflux for 7 hours, followed by stirring overnight at room temperature. The reaction mixture was then heated under reflux for an additional 6 hours. After cooling at room temperature, the reaction mixture was diluted with chloroform and washed with 1M aqueous hydrochloric acid. The organic layer was concentrated under reduced pressure, and the residue was diluted with ethyl acetate and washed sequentially with 1M aqueous hydrochloric acid, water and brine. The organic layer was dried over anhydrous sodium sulfate and then filtered to remove the desiccant, followed by distilling off the solvent under reduced pressure. The resulting residue was converted into a powder form by addition of diethyl ether and n-hexane, and the resulting crystal was collected by filtration to give the titled compound (Compound 5, 205 mg) as a colorless powder.

1H NMR (200 MHz, CHLOROFORM-D) δ 1.33-1.97 (m, 13 H), 2.05-2.21 (m, 3 H), 2.70 (t, J=6.8 Hz, 2 H), 3.69-3.80 (m, 5 H), 3.92-4.02 (m, 1 H), 5.50 (d, J=7.5 Hz, 1 H), 6.64 (dd, J=8.5, 2.5 Hz, 1 H), 6.91 (d, J=2.5 Hz, 1 H), 7.07 (d, J=8.5 Hz, 1 H).

EXAMPLE 6

Synthesis of N-(E-1-hydroxyadamantan-4-yl)-7-methyl-3,4-dihydroquinoline-1(2H)-carboxamide (Compound 6)

To a solution of N,N'-carbonyldiimidazole (219 mg) and triethylamine (188 μl) in chloroform (5 ml), E-4-aminoadamantan-1-ol obtained in Reference Example 2 (150 mg) and N,N-dimethylformamide (2 ml) were added and stirred at room temperature for 1 hour. To the reaction mixture, 7-methyl-1,2,3,4-tetrahydroquinoline obtained in Reference Example 9 (199 mg) was added and heated under reflux for 7 hours, followed by stirring overnight at room temperature. 7-Methyl-1,2,3,4-tetrahydroquinoline (66 mg) was further added and heated under reflux for 5.5 hours. After cooling at room temperature, the reaction mixture was diluted with chloroform and washed with 1M aqueous hydrochloric acid. The organic layer was concentrated under reduced pressure, and the residue was diluted with ethyl acetate and washed sequentially with 1M aqueous hydrochloric acid, water and brine. The organic layer was dried over anhydrous sodium sulfate and then filtered to remove the desiccant, followed by distilling off the solvent under reduced pressure. The resulting residue was converted into a powder form by addition of diethyl ether and n-hexane, and the resulting crystal was collected by filtration to give the titled compound (Compound 6, 223 mg) as a colorless powder.

1H NMR (300 MHz, CHLOROFORM-D) δ 1.35-1.56 (m, 5 H), 1.69-1.80 (m, 4 H) 1.84-1.95 (m, 4 H) 2.06-2.19 (m, 3 H), 2.31 (s, 3 H), 2.72 (t, J=6.8 Hz, 2 H), 3.73 (t, J=6.4 Hz, 2 H), 3.93-4.01 (m, 1 H), 5.47 (d, J=7.2 Hz, 1 H), 6.88 (dd, J=7.7 Hz, 1 H), 7.06 (d, J=7.7 Hz, 1 H), 7.17 (s, 1 H).

EXAMPLE 7

Synthesis of 6-cyano-N-(E-1-hydroxyadamantan-4-yl)-3,4-dihydroquinoline-1(2H)-carboxamide (Compound 7)

To a solution of E-4-aminoadamantan-1-ol obtained in Reference Example 2 (270 mg) in a mixture of chloroform (5 ml) and N,N-dimethylformamide (5 ml), N,N'-carbonyldiimidazole (290 mg) was added and stirred at room temperature for 1 hour. To the reaction mixture, a solution of triethylamine (0.25 ml) and 6-cyano-1,2,3,4-tetrahydroquinoline obtained in Reference Example 10 (390 mg) in chloroform (5 ml) was then added and heated under reflux for 3 hours. After cooling to room temperature, the reaction mixture was stirred overnight and then heated under reflux for 10 hours. After cooling at room temperature, the reaction mixture was diluted with ethyl acetate and washed sequentially with 1.2M aqueous hydrochloric acid and brine. The organic layer was dried over anhydrous magnesium sulfate and then filtered to remove the desiccant, followed by distilling off the solvent under reduced pressure. The resulting residue was purified by silica gel column chromatography (eluting solvent: n-hexane: ethyl acetate=1:1→chloroform:methanol=9:1) to give the titled compound (Compound 7, 45 mg) as a brown powder.

1H NMR (300 MHz, CHLOROFORM-D) δ 1.38-1.68 (m, 5 H), 1.72-1.82 (m, 4 H), 1.85-2.04 (m, 4 H), 2.09-2.22 (m, 3 H), 2.78 (t, J=6.5 Hz, 2 H), 3.21 (s, 3 H), 3.77 (t, J=6.1 Hz, 2 H), 3.95-4.04 (m, 1 H), 5.42 (d, J=7.0 Hz, 1 H), 7.42-7.49 (m, 2 H), 7.51-7.57 (m, 1 H).

EXAMPLE 8

Synthesis of N-(E-1-methoxyadamantan-4-yl)-3,4-dihydroquinoline-1(2H)-carboxamide (Compound 8)

To a solution of N-(E-1-hydroxyadamantan-4-yl)-3,4-dihydroquinoline-1(2H)-carboxamide obtained in Example A-1 (200 mg) in acetonitrile (20 ml), silver(I) oxide (710 mg) and methyl iodide (0.38 ml) were added and stirred overnight at room temperature. The reaction mixture was then heated under reflux for 9 hours, stirred overnight at room temperature, and heated under reflux for an additional 7 hours. After cooling at room temperature, the reaction mixture was filtered through celite, and the solvent was distilled off under reduced pressure. The resulting residue was purified by silica gel column chromatography (eluting solvent: n-hexane:ethyl acetate=1:1) to give the titled compound (Compound 8, 57 mg) as a light-brown powder.

1H NMR (300 MHz, CHLOROFORM-D) δ 1.42-1.64 (m, 4 H), 1.70-1.82 (m, 4 H), 1.85-2.04 (m, 4 H), 2.09-2.22 (m, 3 H), 2.78 (t, J=6.5 Hz, 2 H), 3.73 (t, J=6.1 Hz, 2 H), 3.95-4.04 (m, 1 H), 5.22 (d, J=7.0 Hz, 1 H), 7.02-7.12 (m, 1 H), 7.15-7.24 (m, 2 H), 7.30-7.38 (m, 1 H).

EXAMPLE 9

Synthesis of methyl 4-[(3,4-dihydroquinolin-1(2H)-ylcarbonyl)amino]adamantane-1-carboxylate (Compound 9a), (Compound 9b)

To a solution of methyl 4-aminoadamantane-1-carboxylate obtained in Reference Example 11 (739 mg) in chloroform (10 ml), N,N'-carbonyldiimidazole (629 mg) was added and stirred at room temperature for 1 hour. To the reaction mixture, triethylamine (0.59 ml) and 1,2,3,4-tetrahydroquinoline (0.53 ml) were then added and heated under reflux for 3 hours. After stirring at room temperature for 16 hours, the reaction mixture was heated under reflux for an additional 3 hours. After cooling at room temperature, the reaction mixture was poured into 1M aqueous hydrochloric acid and extracted with ethyl acetate. The extracted organic layer was washed sequentially with 1M aqueous hydrochloric acid, saturated aqueous sodium bicarbonate and brine. After drying over anhydrous magnesium sulfate, the desiccant was filtered off and the solvent was distilled off under reduced pressure. The resulting residue was purified three times by silica gel column chromatography (eluting solvent: chloroform alone→chloroform:ethyl acetate=9:1) to give the titled compound of high polarity (Compound 9b, 554 mg) as a colorless powder. Moreover, an isomer mixture of the titled compounds (a mixture of Compounds 9a and 9b, 439 mg) was obtained as a colorless powder.

Compound 9b

1H NMR (300 MHz, CHLOROFORM-D) δ 1.51-1.65 (m, 4 H), 1.86-2.09 (m, 11 H), 2.76 (t, J=6.7 Hz, 2 H), 3.66 (s, 3 H), 3.76 (t, J=6.2 Hz, 2 H), 3.95-4.00 (m, 1 H), 5.48 (d, J=7.3 Hz, 1 H), 7.02-7.09 (m, 1 H), 7.16-7.23 (m, 2 H), 7.32-7.36 (m, 1 H).

Mixture of Compounds 9a and 9b

1H NMR (300 MHz, CHLOROFORM-D) δ 1.50-1.65 (m, 2 H), 1.70-2.12 (m, 13 H), 2.72-2.80 (m, 2 H), 3.66 (s, 3 H), 3.71-3.80 (m, 2 H), 3.89-4.02 (m, 1 H), 5.38-5.54 (m, 1 H), 7.01-7.11 (m, 1 H), 7.15-7.24 (m, 2 H), 7.31-7.38 (m, 1 H).

EXAMPLE 10

Synthesis of Z-4-[(3,4-dihydroquinolin-1(2H)-ylcarbonyl)amino]adamantane-1-carboxylic acid (Compound 10a) and E-4-[(3,4-dihydroquinolin-1(2H)-ylcarbonyl)amino]adamantane-1-carboxylic acid (Compound 10b)

To a solution of methyl 4-[(3,4-dihydroquinolin-1(2H)-ylcarbonyl)amino]adamantane-1-carboxylate obtained in Example 9 (a mixture of Compounds 9a and 9b, 439 mg) in tetrahydrofuran (5 ml), 1M aqueous sodium hydroxide (5 ml) was added and stirred at room temperature for 16 hours and then heated under reflux for 3 hours. After cooling at room temperature, the reaction mixture was adjusted to pH 2 by dropwise addition of 1M aqueous hydrochloric acid under ice cooling, and then extracted with chloroform. The organic layer was washed with brine, dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=9:1 to 1:1→ethyl acetate alone) and preparative TLC (developing solvent: n-hexane:ethyl acetate=1:2) to give the titled compound of low polarity (Compound 10a, 91 mg) as a colorless powder and the other titled compound of high polarity (Compound 10b, 172 mg) as a colorless powder. Compound 10b was confirmed to be E-form by X-ray crystal structure analysis on the crystal obtained separately by recrystallization from acetone.

Compound 10a

1H NMR (300 MHz, CHLOROFORM-D) δ 1.72-2.05 (m, 14 H), 2.07-2.15 (m, 2 H), 2.76 (t, J=6.7 Hz, 2 H), 3.76 (t, J=6.2 Hz, 2 H), 3.91-3.98 (m, 1 H), 5.44 (d, J=6.7 Hz, 1 H), 7.02-7.09 (m, 1 H), 7.15-7.23 (m, 2 H), 7.32-7.37 (m, 1 H).

Compound 10b

1H NMR (300 MHz, CHLOROFORM-D) δ 1.50-1.69 (m, 4 H), 1.87-2.12 (m, 12 H), 2.76 (t, J=6.8 Hz, 2 H), 3.76 (t, J=6.2 Hz, 2 H), 3.96-4.01 (m, 1 H), 5.49 (d, J=7.0 Hz, 1 H), 7.02-7.11 (m, 1 H), 7.15-7.24 (m, 2 H), 7.30-7.38 (m, 1 H).

EXAMPLE 11a

Synthesis of N-(Z-5-carbamoyladamantan-2-yl)-3,4-dihydroquinoline-1(2H)-carboxamide (Compound 11a)

To a solution of Z-4-[(3,4-dihydroquinolin-1(2H)-ylcarbonyl)amino]adamantane-1-carboxylic acid obtained in Example 10 (Compound 10a, 55 mg) in chloroform (3 ml), N,N-diisopropylethylamine (81 μl), 1-hydroxybenzotriazole monohydrate (36 mg) and 1-ethyl-3-(3-dimethylaminopropyl)carbodiimide hydrochloride (45 mg) were added and stirred at room temperature for 1 hour. To the reaction mixture, ammonia (8M in methanol, 58 μl) was added and stirred at room temperature for 20 hours. The reaction mixture was diluted with water and extracted with ethyl acetate. The extracted organic layer was washed sequentially with saturated aqueous sodium bicarbonate and brine. After drying over anhydrous magnesium sulfate, the desiccant was filtered off and the solvent was distilled off under reduced pressure. The precipitated solid was washed with diethyl ether to give the titled compound (Compound 11a, 40 mg) as a colorless powder.

1H NMR (300 MHz, CHLOROFORM-D) δ 1.53-2.07 (m, 13 H), 2.08-2.18 (m, 2 H), 2.76 (t, J=6.8 Hz, 2 H), 3.75 (t, J=6.2 Hz, 2 H), 3.91-3.98 (m, 1 H), 5.22 (brs, 1 H), 5.43 (d, J=6.4 Hz, 1 H), 5.52 (brs, 1 H), 7.00-7.09 (m, 1 H), 7.14-7.23 (m, 2 H), 7.29-7.39 (m, 1 H).

EXAMPLE 11b

Synthesis of N-(E-5-carbamoyladamantan-2-yl)-3,4-dihydroquinoline-1(2H)-carboxamide (Compound 11B)

Starting with E-4-[(3,4-dihydroquinolin-1(2H)-ylcarbonyl)amino]adamantane-1-carboxylic acid obtained in Example 10 (Compound 10b, 177 mg), the same procedure as shown in Example 11a was repeated for reaction and purification to give the titled compound (Compound 11b, 162 mg) as a colorless powder.

1H NMR (300 MHz, CHLOROFORM-D) δ 1.51-1.69 (m, 5 H), 1.85-2.06 (m, 8 H), 2.07-2.14 (m, 2 H), 2.77 (t, J=6.7 Hz, 2 H), 3.76 (t, J=6.2 Hz, 2 H), 3.95-4.02 (m, 1 H), 5.29 (brs, 1 H), 5.48 (d, J=7.0 Hz, 1 H), 5.59 (brs, 1 H), 7.03-7.10 (m, 1 H), 7.16-7.24 (m, 2 H), 7.30-7.38 (m, 1 H).

EXAMPLE 12

Synthesis of N-(E-1-fluoroadamantan-4-yl)-3,4-dihydroquinoline-1(2H)-carboxamide (Compound 12)

To a solution of N-(E-1-hydroxyadamantan-4-yl)-3,4-dihydroquinoline-1(2H)-carboxamide obtained in Example A-1 (100 mg) in chloroform (2 ml), a solution of diethylaminosulfur trifluoride (54 mg) in chloroform (1 ml) was added dropwise while cooling at −60° C. and stirred overnight at room temperature. Under ice cooling, the reaction mixture was diluted with ethyl acetate and washed sequentially with saturated aqueous sodium bicarbonate and brine. The organic layer was dried over anhydrous magnesium sulfate and then filtered to remove the desiccant, followed by distilling off the solvent under reduced pressure. The resulting residue was purified by preparative TLC (developing solvent: n-hexane:ethyl acetate=1:1) to give the titled compound (Compound 12, 60 mg) as a colorless powder.

1H NMR (300 MHz, CHLOROFORM-D) δ 1.41-1.64 (m, 4 H), 1.82-2.01 (m, 6 H), 2.01-2.14 (m, 2 H), 2.14-2.30 (m, 3 H), 2.76 (t, J=6.7 Hz, 2 H), 3.78 (t, J=6.2 Hz, 2 H), 3.91-4.06 (m, 1 H), 5.37 (d, J=6.1 Hz, 1 H), 7.01-7.12 (m, 1 H), 7.14-7.25 (m, 2 H), 7.28-7.36 (m, 1 H).

EXAMPLE 13

Synthesis of N-(E-1-hydroxyadamantan-4-yl)-2,3,4,5-tetrahydro-1H-1-benzoazepine-1-carboxamide (Compound 13)

To a solution of N,N'-carbonyldiimidazole (219 mg) and triethylamine (188 μl) in chloroform (5 ml), E-4-aminoadamantan-1-ol obtained in Reference Example 2 (150 mg) and N,N-dimethylformamide (2 ml) were added and stirred at room temperature for 1 hour. To the reaction mixture, 2,3,4,5-tetrahydro-1H-1-benzoazepine obtained in Reference Example 12 (199 mg) was added and heated under reflux for 6 hours, followed by stirring overnight at room temperature. The reaction mixture was then heated under reflux for an additional 7 hours. After cooling at room temperature, the reaction mixture was diluted with chloroform and washed with 1M aqueous hydrochloric acid. The organic layer was concentrated under reduced pressure, and the residue was diluted with ethyl acetate and washed sequentially with 1M aqueous hydrochloric acid, water and brine. The organic layer was dried over anhydrous sodium sulfate and then filtered to remove the desiccant, followed by distilling off the solvent under reduced pressure. The resulting residue was converted into a powder form by addition of diethyl ether and n-hexane, and the resulting crystal was collected by filtration to give the titled compound (Compound 13, 153 mg) as a colorless powder.

1H NMR (499 MHz, CHLOROFORM-D, measured at 55° C.) δ 1.01-2.14 (m, 19 H), 2.69-2.78 (m, 2 H), 3.86-3.91 (m, 1 H), 4.46 (d, J=8.0 Hz, 1 H), 7.20-7.30 (m, 4 H).

EXAMPLE 14

Synthesis of N-(E-1-hydroxyadamantan-4-yl)-4,4-dimethyl-3,4-dihydroquinoline-1(2H)-carboxamide (Compound 14)

To a solution of triphosgene (133 mg) in chloroform (5 ml), a solution of triethylamine (0.19 ml) and 4,4-dimethyl-1,2,3,4-tetrahydroquinoline obtained in Reference Example 13 (145 mg) in chloroform (2 ml) was added under ice cooling and stirred for 10 minutes under ice cooling. To the reaction mixture, E-4-aminoadamantan-1-ol obtained in Reference Example 2 (140 mg) and triethylamine (0.19 ml) were then added and stirred at room temperature for 1 hour. Subsequently, N,N-dimethylformamide (5 ml) was added to the reaction mixture, followed by stirring at room temperature for 20 hours. The reaction mixture was poured into 1M aqueous hydrochloric acid and extracted with ethyl acetate. The extracted organic layer was washed sequentially with 1M aqueous hydrochloric acid, water, saturated aqueous sodium bicarbonate and brine. After drying over anhydrous magnesium sulfate, the desiccant was filtered off and the solvent was distilled off under reduced pressure. The resulting residue was purified by silica gel column chromatography (eluting solvent: chloroform alone→chloroform:methanol=9:1). The residue was converted into a powder form by addition of a mixed solvent of diethyl ether and n-hexane, and then collected by filtration to give the titled compound (Compound 14, 212 mg) as a light-yellow powder.

1H NMR (300 MHz, CHLOROFORM-D) δ 1.29 (s, 6 H), 1.38-1.56 (m, 5 H), 1.69-1.79 (m, 6 H), 1.84-1.94 (m, 2 H), 2.04-2.18 (m, 3 H), 3.78 (t, J=6.2 Hz, 2 H), 3.93-3.99 (m, 1 H), 5.36-5.45 (m, 1 H), 7.06-7.14 (m, 1 H), 7.15-7.23 (m, 1 H), 7.27-7.33 (m, 1 H), 7.35-7.43 (m, 1 H).

EXAMPLE 15

Synthesis of N-(E-1-hydroxyadamantan-4-yl)-2-methyl-3,4-dihydroquinoline-1(2H)-carboxamide (Compound 15)

To a solution of E-4-aminoadamantan-1-ol obtained in Reference Example 2 (100 mg) in a mixture of chloroform (3 ml) and N,N-dimethylformamide (2 ml), N,N'-carbonyldiimidazole (107 mg) was added and stirred at room temperature for 1 hour. To the reaction mixture, triethylamine (0.10 ml) and 1,2,3,4-tetrahydroquinaldine (95 μl) were then added and heated under reflux for 9 hours. After cooling at room temperature, the reaction mixture was poured into 1M aqueous hydrochloric acid and extracted with ethyl acetate. The extracted organic layer was washed sequentially with water, saturated aqueous sodium bicarbonate and brine. After drying over anhydrous magnesium sulfate, the desiccant was filtered off and the solvent was distilled off under reduced pressure. The resulting residue was purified by silica gel column chromatography (eluting solvent: chloroform alone→chloroform:methanol=97:3 to 47:3). The residue was converted into a powder form by addition of a mixed solvent of diethyl ether and n-hexane, and then collected by filtration to give the titled compound (Compound 15, 76 mg) as a light-yellow powder.

1H NMR (300 MHz, CHLOROFORM-D) δ 1.14 (d, J=6.7 Hz, 3 H), 1.32-1.79 (m, 10 H), 1.81-1.99 (m, 3 H), 2.02-2.12 (m, 1 H), 2.17-2.33 (m, 2 H), 2.51-2.76 (m, 2 H), 3.88-4.04 (m, 1 H), 4.61-4.86 (m, 1 H), 5.27 (d, J=7.2 Hz, 1 H), 7.05-7.13 (m, 1 H), 7.17-7.31 (m, 3 H).

EXAMPLE 16

Synthesis of N-(E-1-hydroxyadamantan-4-yl)-2,3-dihydro-4H-1,4-benzoxazine 4-carboxamide (Compound 16)

To a solution of N,N'-carbonyldiimidazole (292 mg) and triethylamine (251 μl) in chloroform (7 ml), E-4-aminoadamantan-1-ol obtained in Reference Example 2 (200 mg) and N,N-dimethylformamide (3 ml) were added and stirred at room temperature for 1 hour. To the reaction mixture, 3,4-dihydro-2H-1,4-benzoxazine obtained in Reference Example 14 (243 mg) was added and heated under reflux for 6 hours, followed by stirring overnight at room temperature. The reaction mixture was then heated under reflux for an additional 2 hours. After cooling at room temperature, the reaction mixture was diluted with chloroform and washed with 1M aqueous hydrochloric acid. The organic layer was concentrated under reduced pressure, and the residue was diluted with ethyl acetate and washed sequentially with 1M aqueous hydrochloric acid, water and brine. The organic layer was dried over anhydrous sodium sulfate and then filtered to remove the desiccant, followed by distilling off the solvent under reduced pressure. The resulting residue was dissolved in chloroform and converted into a powder form by addition of diethyl ether and n-hexane, and the resulting crystal was collected by filtration and washed with n-hexane to give the titled compound (Compound 16, 296 mg) as a colorless powder.

1H NMR (300 MHz, CHLOROFORM-D) δ 1.35-1.62 (m, 5 H) 1.71-1.81 (m, 4 H) 1.85-1.94 (m, 2 H) 2.08-2.20 (m, 3 H), 3.88 (t, J=4.8 Hz, 2 H), 3.93-4.00 (m, 1 H), 4.25 (t, J=4.8 Hz, 2 H), 5.65 (d, J=7.0 Hz, 1 H), 6.90-6.99 (m, 2 H), 7.03-7.12 (m, 1 H), 7.30 (dd, J=7.9, 1.5 Hz, 1 H).

EXAMPLE 17

Synthesis of N-(E-1-hydroxyadamantan-4-yl)-6-methyl-2,3-dihydro-4H-1,4-benzoxazine 4-carboxamide (Compound 17)

To a solution of triphosgene (162 mg) in chloroform (5 ml), triethylamine (0.46 ml) and 6-methyl-3,4-dihydro-2H-1,4-benzoxazine hydrochloride obtained in Reference Example 15 (202 mg) were added under ice cooling and stirred at the same temperature for 15 minutes. Next, E-4-aminoadamantan-1-ol obtained in Reference Example 2 (200 mg) was added and stirred for 30 minutes under ice cooling and then at room temperature for 30 minutes. Then, N,N-dimethylformamide (5 ml) was added and stirred overnight at room temperature. The reaction mixture was diluted with ethyl acetate and washed sequentially with 1.2M aqueous hydrochloric acid and brine. The organic layer was dried over anhydrous magnesium sulfate and then filtered to remove the desiccant, followed by distilling off the solvent under reduced pressure. The resulting residue was purified by silica gel column chromatography (eluting solvent: chloroform:methanol=19:1) and recrystallized from a mixture of chloroform and diethyl ether to give the titled compound (Compound 17, 120 mg) as a colorless powder.

1H NMR (300 MHz, CHLOROFORM-D) δ 1.38 (s, 1 H), 1.44-1.62 (m, 4 H), 1.64-1.81 (m, 4 H), 1.82-1.96 (m, 2 H), 2.08-2.22 (m, 3 H), 2.29 (s, 3 H), 3.86 (t, J=4.6 Hz, 2 H), 3.90-4.00 (m, 1 H), 4.22 (t, J=4.6 Hz, 2 H), 5.68 (d, J=6.5 Hz, 1 H), 6.78-6.91 (m, 2 H), 7.14 (s, 1 H).

EXAMPLE 18

Synthesis of Z-5-hydroxyadamantan-2-yl 3,4-dihydroquinoline-1(2H)-carboxylate (Compound 18a) and E-5-hydroxyadamantan-2-yl 3,4-dihydroquinoline-1(2H)-carboxylate (Compound 18b)

To a solution of triphosgene (570 mg) in chloroform (20 ml), triethylamine (1.34 ml) and 4-hydroxyadamantane-1-acetate obtained in Reference Example 16 (1.0 g) were added under ice cooling and stirred at the same temperature for 1 hour. Next, a solution of 1,2,3,4-tetrahydroquinoline (700 mg) in chloroform (5 ml) was added and stirred at room temperature for 3 hours. The reaction mixture was heated under reflux for 2 hours, stirred overnight at room temperature and then heated under reflux for an additional 8 hours. After cooling at room temperature, the reaction mixture was washed sequentially with water, 1.2M aqueous hydrochloric acid and brine. The organic layer was dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=19:1) to give 5-acetoxyadamantan-2-yl 3,4-dihydroquinoline-1(2H)-carboxylate (a mixture of E- and Z-forms, 530 mg) as a colorless oil. To a solution of 5-acetoxyadamantan-2-yl 3,4-dihydroquinoline-1(2H)-carboxylate thus obtained (a mixture of E- and Z-forms, 530 mg) in a mixture of methanol (5 ml) and water (3 ml), potassium carbonate (300 mg) was added and stirred at 70° C. for 3 hours, followed by stirring overnight at room temperature and then at 70° C. for 1.5 hours. After distilling off the solvent under reduced pressure, the residue was diluted with ethyl acetate and washed sequentially with water and brine. The organic layer was dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=9:1 to 4:1 to 1:1) to give the titled compound of low polarity (Compound 18a, 170 mg) as a colorless powder. Compound 18a was confirmed to be Z-form by X-ray crystal structure analysis on the crystal obtained separately by recrystallization from acetone. On the other hand, a colorless powder obtained as a compound of high polarity was washed with a mixture of n-hexane and diethyl ether to give the other titled compound (Compound 18b, 200 mg) as a colorless powder.

Compound 18a

1H NMR (200 MHz, CHLOROFORM-D) δ 1.36 (brs, 1 H), 1.47-1.63 (m, 2 H), 1.66-1.78 (m, 6 H), 1.84-2.05 (m, 4 H), 2.05-2.19 (m, 1 H), 2.30-2.44 (m, 2 H), 2.78 (t, J=6.6 Hz, 2 H), 3.78 (t like, J=6.2 Hz, 2 H), 4.84 (t, J=3.3 Hz, 1 H), 6.91-7.23 (m, 3 H), 7.74 (d, J=8.4 Hz, 1 H).

Compound 18b

1H NMR (200 MHz, CHLOROFORM-D) δ 1.37 (s, 1 H), 1.40-1.62 (m, 2 H), 1.66-2.06 (m, 10 H), 2.07-2.20 (m, 1 H), 2.20-2.34 (m, 2 H), 2.78 (t, J=6.4 Hz, 2 H), 3.80 (t like, J=6.2 Hz, 2 H), 4.95 (t, J=3.3 Hz, 1 H), 6.89-7.25 (m, 3 H), 7.73 (d, J=8.4 Hz, 1 H).

EXAMPLE 19

Synthesis of 6-fluoro-N-(E-1-hydroxyadamantan-4-yl)-2,3-dihydro-4H-1,4-benzoxazine 4-carboxamide (Compound 19)

To a solution of N,N'-carbonyldiimidazole (219 mg) and triethylamine (188 μl) in chloroform (5 ml), E-4-aminoadamantan-1-ol obtained in Reference Example 2 (150 mg) and N,N-dimethylformamide (2 ml) were added and stirred at room temperature for 1 hour. To the reaction mixture, 6-fluoro-3,4-dihydro-2H-1,4-benzoxazine obtained in Reference Example 18 (207 mg) was added and heated under reflux for 8 hours, followed by stirring overnight at room temperature. The reaction mixture was then heated under reflux for an additional 6 hours. After cooling at room temperature, the reaction mixture was diluted with chloroform and washed with 1M aqueous hydrochloric acid. The organic layer was concentrated under reduced pressure, and the residue was diluted with ethyl acetate and washed sequentially with 1M aqueous hydrochloric acid, water and brine. The organic layer was dried over anhydrous sodium sulfate and then filtered to remove the desiccant, followed by distilling off the solvent under reduced pressure. The resulting residue was dissolved in chloroform and converted into a powder form by addition of diethyl ether and n-hexane, and the resulting crystal was collected by filtration to give the titled compound (Compound 19, 169 mg) as a light-pink powder.

1H NMR (300 MHz, CHLOROFORM-D) 1.34-1.65 (m, 5 H), 1.73-1.81 (m, 4 H), 1.86-1.94 (m, 2 H), 2.12-2.21 (m, 3 H), 3.83-3.88 (m, 2 H), 3.94-4.01 (m, 1 H), 4.20-4.25 (m, 2 H), 5.54 (d, J=6.5 Hz, 1 H), 6.76 (dd, J=7.6, 3.0 Hz, 1 H), 6.87-6.93 (m, 1 H), 7.10 (dd, J=9.8, 3.0 Hz, 1 H).

EXAMPLE 20

Synthesis of methyl 4-[(E-5-hydroxyadamantan-2-yl)carbamoyl]-3,4-dihydro-2H-1,4-benzoxazine-6-carboxylate (Compound 20)

To a solution of N,N'-carbonyldiimidazole (728 mg) and triethylamine (0.63 ml) in chloroform (20 ml), E-4-aminoadamantan-1-ol obtained in Reference Example 2 (500 mg) and N,N-dimethylformamide (8 ml) were added and stirred at room temperature for 1 hour. To the reaction mixture, methyl 3,4-dihydro-2H-1,4-benzoxazine-6-carboxylate obtained in Reference Example 22 (867 mg) was added and heated under reflux for 1.5 hours, followed by stirring overnight at room temperature. The reaction mixture was then heated under reflux for an additional 8 hours. After cooling at room temperature, the reaction mixture was diluted with chloroform and washed with water. The organic layer was concentrated under reduced pressure, and the residue was diluted with ethyl acetate and washed sequentially with water, 1M aqueous hydrochloric acid, saturated aqueous sodium bicarbonate and brine. The organic layer was dried over anhydrous sodium sulfate and then filtered to remove the desiccant, followed by distilling off the solvent under reduced pressure. The resulting residue was dissolved in chloroform and converted into a powder form by addition of diethyl ether and n-hexane, and the resulting crystal was collected by filtration to give the titled compound (Compound 20, 972 mg) as a light-brown powder.

1H NMR (300 MHz, CHLOROFORM-D) δ 1.47-1.83 (m, 9 H), 1.85-1.96 (m, 2 H), 2.10-2.23 (m, 3 H), 3.85-3.94 (m, 5 H), 3.95-4.03 (m, 1 H), 4.27-4.34 (m, 2 H), 5.61 (d, J=6.8 Hz, 1 H), 6.99 (d, J=8.7 Hz, 1 H), 7.75 (dd, J=8.70, 2.0 Hz, 1 H), 8.11 (d, J=2.0 Hz, 1 H).

EXAMPLE 21

Synthesis of 4-[(E-5-hydroxyadamantan-2-yl)carbamoyl]-3,4-dihydro-2H-1,4-benzoxazine-6-carboxylic acid (Compound 21)

To a solution of methyl 4-[(E-5-hydroxyadamantan-2-yl) carbamoyl]-3,4-dihydro-2H-1,4-benzoxazine-6-carboxylate obtained in Example 20 (700 mg) in tetrahydrofuran:methanol=1:1 (20 ml), 8M aqueous sodium hydroxide (10 ml) was added and stirred overnight at room temperature. The reaction mixture was diluted with 6M aqueous hydrochloric acid and extracted with ethyl acetate. During the extraction, a crystal precipitated from the aqueous layer was collected by filtration. The organic layer was washed with brine and then dried over anhydrous sodium sulfate. After the desiccant was filtered off, the solvent was distilled off under reduced pressure. The resulting residue was dissolved in methanol and converted into a powder form by addition of diethyl ether, and the resulting crystal was collected by filtration. This crystal and the crystal collected from the aqueous layer were combined and dissolved in methanol, and then converted into a powder form by addition of diethyl ether. The resulting crystal was collected by filtration to give the titled compound (Compound 21, 600 mg) as a colorless powder.

1H NMR (300 MHz, DMSO-D6) δ 1.27-1.39 (m, 2 H), 1.56-1.74 (m, 6 H), 1.82-1.93 (m, 2 H), 1.95-2.11 (m, 3 H), 3.65-3.72 (m, 1 H), 3.73-3.79 (m, 2 H), 4.20-4.27 (m, 2 H), 4.41 (s, 1 H), 6.55 (d, J=5.1 Hz, 1 H), 6.92 (d, J=8.5 Hz, 1 H), 7.49 (dd, J=8.5, 2.1 Hz, 1 H), 8.22 (d, J=2.1 Hz, 1 H), 12.52 (brs, 1H).

EXAMPLE 22

Synthesis of N-(E-5-hydroxyadamantan-2-yl)-2,3-dihydro-4H-1,4-benzoxazine-4,6-dicarboxamide (Compound 22)

To a solution of 4-[(E-5-hydroxyadamantan-2-yl)carbamoyl]-3,4-dihydro-2H-1,4-benzoxazine-6-carboxylic acid obtained in Example 21 (300 mg) in chloroform (20 ml), N,N-diisopropylethylamine (0.42 ml), 1-hydroxybenzotriazole monohydrate (187 mg) and 1-ethyl-3-(3-dimethylaminopropyl)carbodiimide hydrochloride (234 mg) were added and stirred at room temperature for 1 hour. To the reaction mixture, ammonia (8M in methanol, 0.30 ml) was added and stirred at room temperature for 2 days. The precipitated crystal was collected by filtration and washed with chloroform. The resulting crystal was dissolved in chloroform/methanol and converted into a powder form by addition of dichloroether to give a colorless powder (268 mg). The resulting powder (20 mg) was washed with water to give the titled compound (Compound 22, 10 mg) as a colorless powder.

1H NMR (300 MHz, DMSO-D6) δ1.27-1.39 (m, 2 H), 1.56-1.73 (m, 6 H), 1.79-1.91 (m, 2 H), 1.94-2.11 (m, 3 H), 3.64-3.81 (m, 3 H), 4.17-4.24 (m, 2 H), 4.41 (s, 1 H), 6.46 (d, J=5.3 Hz, 1 H), 6.88 (d, J=8.5 Hz, 1 H), 7.13 (brs, 1 H), 7.45 (dd, J=8.5, 2.1 Hz, 1 H), 7.76 (brs, 1 H), 8.09 (d, J=2.1 Hz, 1 H).

EXAMPLE 23

Synthesis of N-(E-5-hydroxyadamantan-2-yl)-7-methyl-2,3-dihydro-4H-1,4-benzoxazine-4-carboxamide (Compound 23)

To a solution of N,N'-carbonyldiimidazole (219 mg) and triethylamine (188 µl) in chloroform (5 ml), E-4-aminoadamantan-1-ol obtained in Reference Example 2 (150 mg) and N,N-dimethylformamide (2 ml) were added and stirred at room temperature for 1 hour. To the reaction mixture, 7-methyl-3,4-dihydro-2H-1,4-benzoxazine obtained in Reference Example 20 (201 mg) was added and heated under reflux for 7.5 hours, followed by stirring overnight at room temperature. The reaction mixture was then heated under reflux for an additional 1.5 hours. After cooling at room temperature, the reaction mixture was diluted with chloroform and washed with water. The organic layer was concentrated under reduced pressure, and the residue was diluted with ethyl acetate and washed sequentially with water, 1M aqueous hydrochloric acid, saturated aqueous sodium bicarbonate and brine. The organic layer was dried over anhydrous sodium sulfate and then filtered to remove the desiccant, followed by distilling off the solvent under reduced pressure. The resulting residue was dissolved in chloroform and converted into a powder form by addition of diethyl ether and n-hexane. Since impurities were contained, the resulting crystal was dissolved again in chloroform and then converted into a powder form by addition of diethyl ether and n-hexane, and the crystal was collected by filtration to give the titled compound (Compound 23, 148 mg) as a light-pink powder.

1H NMR (300 MHz, CHLOROFORM-D) δ 1.31-1.63 (m, 5 H), 1.70-1.80 (m, 4 H), 1.84-1.94 (m, 2 H), 2.08-2.18 (m, 3 H), 2.30 (s, 3 H), 3.81-3.90 (m, 2 H), 3.91-4.01 (m, 1 H), 4.18-4.26 (m, 2 H), 5.64 (d, J=7.3 Hz, 1 H), 6.71-6.80 (m, 2 H), 7.17 (d, J=8.1 Hz, 1 H).

EXAMPLE 24

Synthesis of 7-fluoro-N-(E-5-hydroxyadamantan-2-yl)-2,3-dihydro-4H-1,4-benzoxazine-4-carboxamide (Compound 24)

To a solution of triphosgene (138 mg) in chloroform (3 ml), a solution of triethylamine (0.19 ml) and 7-fluoro-3,4-dihydro-2H-1,4-benzoxazine obtained in Reference Example 19 (142 mg) in chloroform (1 ml) was added under ice cooling and stirred at the same temperature for 10 minutes. To the reaction mixture, E-4-aminoadamantan-1-ol obtained in Reference Example 2 (153 mg), triethylamine (0.19 ml) and N,N-dimethylformamide (3 ml) were then added and stirred at room temperature for 20 hours. The reaction mixture was poured into water and extracted with ethyl acetate. The organic layer was washed sequentially with 1M aqueous hydrochloric acid, saturated aqueous sodium bicarbonate, water and brine. After drying over anhydrous magnesium sulfate, the desiccant was filtered off and the solvent was distilled off under reduced pressure. The resulting residue was purified by silica gel column chromatography (eluting solvent: chloroform alone→chloroform:methanol=47:3). The residue was converted into a powder form by addition of a mixed solvent of diethyl ether and n-hexane, and then collected by filtration to give the titled compound (Compound 24, 190 mg) as a colorless powder.

1H NMR (300 MHz, CHLOROFORM-D) δ 1.38 (s, 1 H), 1.46-1.60 (m, 4 H), 1.71-1.81 (m, 4 H), 1.85-1.94 (m, 2 H), 2.09-2.18 (m, 3 H), 3.86 (dd, J=5.2, 4.2 Hz, 2 H), 3.92-3.99 (m, 1 H), 4.24 (dd, J=5.2, 4.2 Hz, 2 H), 5.46-5.53 (m, 1 H), 6.64-6.73 (m, 2 H), 7.20-7.25 (m, 1 H).

EXAMPLE 25

Synthesis of N-(E-5-hydroxyadamantan-2-yl)-5-methyl-2,3-dihydro-4H-1,4-benzoxazine-4-carboxamide (Compound 25)

To a solution of triphosgene (356 mg) in chloroform (5 ml), a solution of triethylamine (0.50 ml) and 5-methyl-3,4-dihydro-2H-1,4-benzoxazine obtained in Reference Example 21 (358 mg) in chloroform (3 ml) was added under ice cooling and stirred at the same temperature for 30 minutes. To the reaction mixture, E-4-aminoadamantan-1-ol obtained in Reference Example 2 (200 mg), triethylamine (251 μl) and N,N-dimethylformamide (5 ml) were then added and stirred at room temperature for 2 days. The reaction mixture was diluted with chloroform and washed with water. The organic layer was concentrated under reduced pressure, and the residue was diluted with ethyl acetate and washed sequentially with 1M aqueous hydrochloric acid, saturated aqueous sodium bicarbonate and brine. The organic layer was dried over anhydrous sodium sulfate and then filtered to remove the desiccant, followed by distilling off the solvent under reduced pressure. The resulting residue was purified by silica gel column chromatography (eluting solvent: n-hexane:ethyl acetate=1:1→chloroform:methanol=9:1). The residue was dissolved in chloroform and then converted into a powder form by addition of diethyl ether and n-hexane, and the crystal was collected by filtration to give the titled compound (Compound 25, 168 mg) as a light-brown powder.

1H NMR (300 MHz, DMSO-D6) δ 1.25-1.38 (m, 2 H), 1.54-1.73 (m, 8 H), 1.90-2.03 (m, 3 H), 2.10 (s, 3 H), 3.62-3.76 (m, 3 H), 4.08-4.16 (m, 2 H), 4.40 (s, 1 H), 6.31 (d, J=7.0 Hz, 1 H), 6.65-6.78 (m, 2 H), 6.92-7.00 (m, 1 H).

EXAMPLE 26

Synthesis of N-(E-5-hydroxyadamantan-2-yl)-6-(trifluoromethyl)-2,3-dihydro-4H-1,4-benzoxazine-4-carboxamide (Compound 26)

To a solution of triphosgene (356 mg) in chloroform (5 ml), a solution of triethylamine (0.50 ml) and 6-(trifluoromethyl)-3,4-dihydro-2H-1,4-benzoxazine obtained in Reference Example 24 (488 mg) in chloroform (3 ml) was added under ice cooling and stirred at the same temperature for 30 minutes. To the reaction mixture, E-4-aminoadamantan-1-ol obtained in Reference Example 2 (200 mg), triethylamine (251 μl) and N,N-dimethylformamide (5 ml) were then added and stirred overnight at room temperature. The reaction mixture was diluted with chloroform and washed with water. The organic layer was concentrated under reduced pressure, and the residue was diluted with ethyl acetate and washed sequentially with 1M aqueous hydrochloric acid, saturated aqueous sodium bicarbonate and brine. The organic layer was dried over anhydrous sodium sulfate and then filtered to remove the desiccant, followed by distilling off the solvent under reduced pressure. The resulting residue was purified by silica gel column chromatography (eluting solvent: n-hexane:ethyl acetate=1:1→chloroform:methanol=10:1 to 9:1). The residue was dissolved in chloroform and then converted into a powder form by addition of diethyl ether, and the crystal was collected by filtration to give the titled compound (Compound 26, 324 mg) as a colorless powder.

1H NMR (300 MHz, CHLOROFORM-D) δ 1.36 (s, 1 H), 1.46-1.65 (m, 4 H), 1.71-1.82 (m, 4 H), 1.85-1.96 (m, 2 H), 2.09-2.21 (m, 3 H), 3.86-3.94 (m, 2 H), 3.94-4.04 (m, 1 H), 4.26-4.34 (m, 2 H), 5.47 (d, J=7.6 Hz, 1 H), 7.04 (d, J=8.3 Hz, 1 H), 7.31 (dd, J=8.3, 2.2 Hz, 1 H), 7.66 (d, J=2.2 Hz, 1 H).

EXAMPLE 27

Synthesis of N-(E-5-hydroxyadamantan-2-yl)-2,3-dihydro-4H-1,4-benzothiazine-4-carboxamide (Compound 27)

To a solution of triphosgene (445 mg) in chloroform (10 ml), a solution of triethylamine (0.62 ml) and 3,4-dihydro-2H-1,4-benzothiazine obtained in Reference Example 25 (452 mg) in chloroform (2 ml) was added under ice cooling and stirred at the same temperature for 10 minutes. To the reaction mixture, E-4-aminoadamantan-1-ol obtained in Reference Example 2 (500 mg), triethylamine (0.62 ml) and N,N-dimethylformamide (8 ml) were then added and stirred at room temperature for 17 hours. The reaction mixture was poured into 1M aqueous hydrochloric acid and extracted with ethyl acetate. The organic layer was washed sequentially with 1M aqueous hydrochloric acid, saturated aqueous sodium bicarbonate, water and brine. After drying over anhydrous magnesium sulfate, the desiccant was filtered off and the solvent was distilled off under reduced pressure. The resulting residue was converted into a powder form by addition of diethyl ether, and then collected by filtration to give a crude product of the titled compound (788 mg) as a light-pink powder. The resulting crude product (150 mg) was converted into a powder form by addition of chloroform and diethyl ether, and then collected by filtration to give the titled compound (Compound 27, 111 mg) as a light-pink powder.

1H NMR (300 MHz, CHLOROFORM-D) δ 1.34 (s, 1 H), 1.43-1.48 (m, 4 H), 1.69-1.77 (m, 4 H), 1.83-1.91 (m, 2 H), 2.04-2.15 (m, 3 H), 3.16-3.21 (m, 2 H), 3.88-3.98 (m, 3 H), 5.26-5.33 (m, 1 H), 7.06-7.15 (m, 2 H), 7.22-7.30 (m, 2 H).

EXAMPLE 28

Synthesis of N-(E-5-hydroxyadamantan-2-yl)-2,3-dihydro-4H-1,4-benzothiazine-4-carboxamide 1-oxide (Compound 28)

To a solution of N-(E-5-hydroxyadamantan-2-yl)-2,3-dihydro-4H-1,4-benzothiazine-4-carboxamide obtained in Example 27 (150 mg) in methanol (6 ml), 3-chloroperbenzoic acid (83 mg) was added under ice cooling and stirred for 30 minutes under ice cooling. The reaction mixture was diluted with water and extracted with ethyl acetate. The organic layer was washed sequentially with 5% aqueous sodium thiosulfate and brine. The aqueous layer was extracted again with chloroform, combined with the organic layer obtained earlier, dried over anhydrous magnesium sulfate and then filtered to remove the desiccant, followed by distilling off the solvent under reduced pressure. The resulting residue was purified by silica gel column chromatography (eluting solvent: chloroform alone→chloroform:methanol=47:3). The resulting residue was dissolved by heating in a small volume of chloroform and converted into a powder form by addition of diethyl ether, and then collected by filtration to give the titled compound (Compound 28, 130 mg) as a colorless powder.

1H NMR (300 MHz, CHLOROFORM-D) δ 1.36-1.63 (m, 5 H), 1.69-1.80 (m, 4 H), 1.81-1.95 (m, 2 H), 2.01-2.15 (m, 2 H), 2.20-2.30 (m, 1 H), 3.07-3.17 (m, 1 H), 3.26-3.36 (m, 1 H), 3.71-3.82 (m, 1 H), 3.94-4.00 (m, 1 H), 4.47-4.59 (m, 1 H), 5.32-5.37 (m, 1 H), 7.32-7.38 (m, 1 H), 7.48-7.57 (m, 2 H), 7.83-7.87 (m, 1 H).

EXAMPLE 29

Synthesis of N-(E-5-hydroxyadamantan-2-yl)-2,3-dihydro-4H-1,4-benzothiazine-4-carboxamide 1,1-dioxide (Compound 29)

To a solution of N-(E-5-hydroxyadamantan-2-yl)-2,3-dihydro-4H-1,4-benzothiazine-4-carboxamide obtained in Example 27 (200 mg) in acetic acid (8 ml), 30% aqueous hydrogen peroxide (175 µl) was added and stirred at 85° C. for 3 hours. After cooling at room temperature, the reaction mixture was poured into 0.5M aqueous sodium hydroxide and extracted twice with chloroform. The combined organic layers were washed with brine and dried over anhydrous magnesium sulfate. The desiccant was filtered off and the solvent was distilled off under reduced pressure. The resulting residue was dissolved by heating in a small volume of chloroform and converted into a powder form by addition of diethyl ether, and then collected by filtration to give the titled compound (Compound 29, 126 mg) as a light-yellow powder.

1H NMR (300 MHz, CHLOROFORM-D) δ 1.35-1.68 (m, 5 H), 1.73-1.81 (m, 4 H), 1.85-1.93 (m, 2 H), 2.09-2.21 (m, 3 H), 3.52-3.58 (m, 2 H), 3.94-3.99 (m, 1 H), 4.42-4.47 (m, 2 H), 5.32-5.38 (m, 1 H), 7.36-7.46 (m, 2 H), 7.55-7.61 (m, 1 H), 7.97-8.01 (m, 1 H).

EXAMPLE 30

Synthesis of 4-acetyl-N-(E-5-hydroxyadamantan-2-yl)-3,4-dihydroquinoxaline-1(2H)-carboxamide (Compound 30)

To a solution of N,N'-carbonyldiimidazole (219 mg) and triethylamine (188 µl) in chloroform (5 ml), E-4-aminoadamantan-1-ol obtained in Reference Example 2 (150 mg) and N,N-dimethylformamide (2 ml) were added and stirred at room temperature for 1 hour. To the reaction mixture, 1-acetyl-1,2,3,4-tetrahydroquinoxaline obtained in Reference Example 27 (238 mg) was added and heated under reflux for 7 hours, followed by stirring overnight at room temperature. The reaction mixture was then heated under reflux for an additional 7 hours. After cooling at room temperature, the reaction mixture was diluted with chloroform and washed with 1M aqueous hydrochloric acid. The organic layer was concentrated under reduced pressure, and the residue was diluted with ethyl acetate and washed sequentially with 1M aqueous hydrochloric acid, saturated aqueous sodium bicarbonate and brine. The organic layer was dried over anhydrous sodium sulfate and then filtered to remove the desiccant, followed by distilling off the solvent under reduced pressure. The resulting residue was converted into a powder form by addition of diethyl ether and n-hexane, and the crystal was collected by filtration to give the titled compound (Compound 30, 30 mg) as a yellow powder.

1H NMR (300 MHz, CHLOROFORM-D) δ 1.36 (s, 1 H), 1.45-1.63 (m, 4 H), 1.71-1.81 (m, 4 H), 1.85-1.95 (m, 2 H), 2.07-2.21 (m, 3 H), 2.28 (s, 3 H), 3.84-4.02 (m, 5 H), 5.24-5.35 (m, 1 H), 7.11-7.29 (m, 3 H), 7.45-7.54 (m, 1 H).

EXAMPLE 31

Synthesis of tert-butyl 4-[(E-5-hydroxyadamantan-2-yl)carbamoyl]-3,4-dihydroquinoxaline-1(2H)-carboxylate (Compound 31)

To a solution of N,N'-carbonyldiimidazole (363 mg) and triethylamine (312 µl) in chloroform (10 ml), E-4-aminoadamantan-1-ol obtained in Reference Example 2 (250 mg) and N,N-dimethylformamide (4 ml) were added and stirred at room temperature for 1 hour. To the reaction mixture, tert-butyl 3,4-dihydroquinoxaline-1(2H)-carboxylate obtained in Reference Example 28 (698 mg) was added and heated under reflux for 6 hours, followed by stirring overnight at room temperature. The reaction mixture was then heated under reflux for an additional 8 hours. After cooling at room temperature, the reaction mixture was diluted with water and extracted with chloroform. The organic layer was concentrated under reduced pressure, and the residue was diluted with ethyl acetate and washed sequentially with 0.1M aqueous hydrochloric acid, saturated aqueous sodium bicarbonate and brine. The organic layer was dried over anhydrous sodium sulfate and then filtered to remove the desiccant, followed by distilling off the solvent under reduced pressure. The resulting residue was purified by silica gel column chromatography (eluting solvent: n-hexane:ethyl acetate=5:1 to 1:1→chloroform:methanol=9:1) to give the titled compound (Compound 31, 290 mg) as a colorless amorphous substance.

1H NMR (300 MHz, CHLOROFORM-D) δ 1.35 (s, 1 H), 1.43-1.61 (m, 13 H), 1.70-1.79 (m, 4 H), 1.84-1.93 (m, 2 H), 2.06-2.19 (m, 3 H), 3.80-3.86 (m, 4 H), 3.89-3.97 (m, 1 H), 5.38 (d, J=6.5 Hz, 1 H), 7.04-7.20 (m, 2 H), 7.28-7.33 (m, 1 H), 8.00-8.05 (m, 1 H).

EXAMPLE 32

Synthesis of N-(E-5-hydroxyadamantan-2-yl)-3,4-dihydroquinoxaline-1(2H)-carboxamide hydrochloride (Compound 32)

To a solution of tert-butyl 4-[(E-5-hydroxyadamantan-2-yl)carbamoyl]-3,4-dihydroquinoxaline-1(2H)-carboxylate obtained in Example 31 (190 mg) in ethyl acetate (5 ml), 4N hydrochloric acid (in ethyl acetate, 1 ml) was added and stirred overnight at room temperature. After the reaction mixture was concentrated, ethyl acetate and isopropyl ether were added to the resulting residue, and the precipitated crystal was collected by filtration to give the titled compound (Compound 32, 71 mg) as a light-pink powder.

1H NMR (300 MHz, DMSO-D6) δ 1.29-1.42 (m, 2 H), 1.50-1.72 (m, 8 H), 1.93-2.02 (m, 3 H), 3.17-3.26 (m, 2 H), 3.54-3.61 (m, 2 H), 3.63-3.70 (m, 1 H), 5.88 (d, J=6.7 Hz, 1 H), 6.55-6.64 (m, 1 H), 6.68 (dd, J=8.1, 1.2 Hz, 1 H), 6.84-6.92 (m, 1 H), 7.19 (dd, J=8.1, 1.2 Hz, 1 H).

EXAMPLE 33

Synthesis of N-(E-5-hydroxyadamantan-2-yl)-4-methyl-3,4-dihydroquinoxaline-1(2H)-carboxamide hydrochloride (Compound 33)

To a solution of N,N'-carbonyldiimidazole (195 mg) and triethylamine (167 µl ) in chloroform (5 ml), E-4-aminoadamantan-1-ol obtained in Reference Example 2 (170 mg) and N,N-dimethylformamide (2 ml) were added and stirred at room temperature for 1 hour. To the reaction mixture, 1-methyl-1,2,3,4-tetrahydroquinoxaline obtained in Reference Example 29 (178 mg) was added and heated under reflux for 6 hours, followed by stirring overnight at room temperature. The reaction mixture was then heated under reflux for an additional 5 hours. After cooling at room temperature, the reaction mixture was diluted with chloroform and washed with water. The organic layer was concentrated under reduced pressure, and the residue was diluted with ethyl acetate and washed sequentially with water and brine. The organic layer was dried over anhydrous sodium sulfate and then filtered to remove the desiccant, followed by distilling off the solvent under reduced pressure. The resulting residue was purified by silica gel column chromatography (eluting solvent: n-hexane:ethyl acetate=1:1→chloroform:methanol=10:1). The resulting residue was converted into a powder form by addition of diethyl ether and n-hexane, and the crystal was collected by filtration to give N-(E-5-hydroxyadamantan-2-yl)-4-methyl-3,4-dihydroquinoxaline-1(2H)-carboxamide (134 mg) as a brown powder. To a solution of N-(E-5-hydroxyadamantan-2-yl)-4-methyl-3,4-dihydroquinoxaline-1(2H)-carboxamide thus obtained (80 mg) in ethanol (2 ml), 4N hydrochloric acid (in ethyl acetate, 1 ml) was added under ice cooling and stirred at the same temperature for 2 hours. The reaction mixture was concentrated, and the resulting residue was dissolved in methanol and then converted into a powder form by addition of diethyl ether. The crystal was collected by filtration to give the titled compound (Compound 33, 61 mg) as a purple powder.

1H NMR (300 MHz, DMSO-D6) δ 1.28-1.40 (m, 2 H), 1.50-1.71 (m, 8 H), 1.92-2.01 (m, 3 H), 2.89 (s, 3 H), 3.20-3.27 (m, 2 H), 3.62-3.70 (m, 3 H), 5.83 (d, J=6.4 Hz, 1 H), 6.60-6.67 (m, 1 H), 6.73-6.78 (m, 1 H), 6.94-7.01 (m, 1 H), 7.17-7.21 (m, 1 H).

EXAMPLE 34

Synthesis of N-adamantan-2-yl-2,3-dihydro-4H-1,4-benzoxazine-4-carboxamide (Compound 34)

To a solution of triphosgene (119 mg) in chloroform (3 ml), a solution of triethylamine (332 μl) and 3,4-dihydro-2H-1,4-benzoxazine obtained in Reference Example 14 (108 mg) in chloroform (2 ml) was added under ice cooling and stirred at the same temperature for 10 minutes. To the reaction mixture, 2-adamantaneamine hydrochloride (150 mg) and triethylamine (166 μl) were then added and stirred at room temperature for 16 hours. The reaction mixture was poured into water and extracted with ethyl acetate. The organic layer was washed sequentially with 1M aqueous hydrochloric acid, saturated aqueous sodium bicarbonate and brine. After drying over anhydrous magnesium sulfate, the desiccant was filtered off and the solvent was distilled off under reduced pressure. The resulting residue was purified by silica gel column chromatography (eluting solvent: n-hexane:ethyl acetate=4:1). The resulting residue was dissolved in a small volume of chloroform and converted into a powder form by addition of diethyl ether, and then collected by filtration to give the titled compound (Compound 34, 96 mg) as a colorless powder.

1H NMR (300 MHz, CHLOROFORM-D) δ 1.61-1.66 (m, 4 H), 1.71-1.76 (m, 2 H), 1.79-1.89 (m, 6 H), 1.92-1.99 (m, 2 H), 3.89 (dd, J=5.1, 4.0 Hz, 2 H), 3.96-4.02 (m, 1 H), 4.25 (dd, J=5.1, 4.0 Hz, 2 H), 5.72-5.81 (m, 1 H), 6.90-6.97 (m, 2 H), 7.03-7.09 (m, 1 H), 7.31-7.35 (m, 1 H).

EXAMPLE 35

Synthesis of methyl 4-[(2,3-dihydro-4H-1,4-benzoxazin-4-ylcarbonyl)amino]adamantane-1-carboxylate (Compound 35a), (Compound 35b)

To a solution of triphosgene (223 mg) in chloroform (5 ml), a solution of triethylamine (0.31 ml) and 3,4-dihydro-2H-1,4-benzoxazine obtained in Reference Example 14 (203 mg) in chloroform (2 ml) was added under ice cooling and stirred at the same temperature for 10 minutes. To the reaction mixture, methyl 4-aminoadamantane-1-carboxylate obtained in Reference Example 11 (314 mg) and triethylamine (0.31 ml) were then added and stirred under ice cooling for 3 hours. The reaction mixture was warmed to room temperature and further stirred for 16 hours. The reaction mixture was diluted with ethyl acetate, and the organic layer was washed sequentially with water, 1M aqueous hydrochloric acid, saturated aqueous sodium bicarbonate and brine. After drying over anhydrous magnesium sulfate, the desiccant was filtered off and the solvent was distilled off under reduced pressure. The resulting residue was purified by silica gel column chromatography (eluting solvent: n-hexane:ethyl acetate=4:1 to 1:1) to give an isomer mixture of the titled compounds (a mixture of Compounds 35a and 35b, 474 mg) as a light-yellow amorphous substance.

1H NMR (300 MHz, CHLOROFORM-D) δ 1.53-1.69 (m, 4 H), 1.78-2.12 (m, 9 H), 3.66 (s, 3 H), 3.86-3.91 (m, 2 H), 3.95-4.01 (m, 1 H), 4.22-4.28 (m, 2 H), 5.69-5.75 (m, 1 H), 6.90-6.99 (m, 2 H), 7.03-7.11 (m, 1 H), 7.29-7.34 (m, 1 H).

EXAMPLE 36

Synthesis of 4-[(2,3-dihydro-4H-1,4-benzoxazin-4-ylcarbonyl)amino]adamantane-1-carboxylic acid (Compound 36a), (Compound 36b)

To a solution of methyl 4-[(2,3-dihydro-4H-1,4-benzoxazin-4-ylcarbonyl)amino]adamantane-1-carboxylate obtained in Example 35 (a mixture of Compounds 35a and 35b, 474 mg) in tetrahydrofuran (6 ml), 1M aqueous sodium hydroxide (6 ml) was added and heated under reflux for 3 hours. After cooling at room temperature, the reaction mixture was adjusted to pH 1 to 2 by dropwise addition of 1M aqueous hydrochloric acid under ice cooling, and then extracted with ethyl acetate. The organic layer was washed with brine and dried over anhydrous magnesium sulfate. The desiccant was filtered off and the solvent was distilled off under reduced pressure to give an isomer mixture of the titled compounds (a mixture of Compounds 36a and 36b, 469 mg) as a light-pink powder.

1H NMR (300 MHz, CHLOROFORM-D) δ 1.54-1.69 (m, 3 H), 1.76-2.14 (m, 10 H), 3.86-3.92 (m, 2 H), 3.95-4.02 (m, 1 H), 4.22-4.28 (m, 2 H), 5.66-5.76 (m, 1 H), 6.91-6.99 (m, 2 H), 7.04-7.11 (m, 1 H), 7.29-7.34 (m, 1 H).

EXAMPLE 37

Synthesis of N-[Z-5-carbamoyladamantan-2-yl]-2,3-dihydro-4H-1,4-benzoxazine-4-carboxamide (Compound 37a) and N-[E-5-carbamoyladamantan-2-yl]-2,3-dihydro-4H-1,4-benzoxazine-4-carboxamide (Compound 37b)

To a solution of 4-[(2,3-dihydro-4H-1,4-benzoxazin-4-ylcarbonyl)amino]adamantane-1-carboxylic acid obtained in Example 36 (a mixture of Compounds 36a and 36b, 469 mg) in chloroform (10 ml), N,N-diisopropylethylamine (0.67 ml), 1-hydroxybenzotriazole monohydrate (294 mg) and 1-ethyl-3-(3-dimethylaminopropyl)carbodiimide hydrochloride (368 mg) were added and stirred at room temperature for 1 hour. To the reaction mixture, ammonia (8M in methanol, 0.48 ml) was added and stirred at room temperature for 20 hours. The reaction mixture was poured into saturated aqueous sodium bicarbonate and extracted with chloroform. The organic layer was washed with brine and dried over anhydrous magnesium sulfate. The desiccant was filtered off and the solvent was distilled off under reduced pressure. The resulting residue was purified by silica gel column chromatography (eluting solvent: ethyl acetate alone→chloroform:methanol=9:1) and preparative TLC (developing solvent: ethyl acetate alone). A powder generated upon addition of chloroform and diethyl ether was collected by filtration to give the titled compound of low polarity (Compound 37a, 41 mg) as a colorless powder and the other titled compound of high polarity (Compound 37b, 294 mg) as a colorless powder.

Compound 37a

1H NMR (300 MHz, CHLOROFORM-D) δ 1.60-1.90 (m, 10 H), 2.02-2.08 (m, 1 H), 2.10-2.18 (m, 2 H), 3.85-3.91 (m, 2 H), 3.92-3.99 (m, 1 H), 4.21-4.29 (m, 2 H), 5.31 (brs, 1 H), 5.54 (brs, 1 H), 5.64-5.70 (m, 1 H), 6.90-6.97 (m, 2 H), 7.03-7.09 (m, 1 H), 7.29-7.34 (m, 1 H).

Compound 37b

1H NMR (300 MHz, CHLOROFORM-D) δ 1.55-1.71 (m, 4 H), 1.87-2.15 (m, 9 H), 3.89 (dd, J=5.2, 4.1 Hz, 2 H), 3.95-4.02 (m, 1 H), 4.25 (dd, J=5.2, 4.1 Hz, 2 H), 5.33 (brs, 1 H), 5.58 (brs, 1 H), 5.68-5.76 (m, 1 H), 6.91-6.98 (m, 2 H), 7.04-7.11 (m, 1 H), 7.29-7.33 (m, 1 H).

EXAMPLE 38

Synthesis of N-(E-5-carbamoyladamantan-2-yl)-6-fluoro-2,3-dihydro-4H-1,4-benzoxazine-4-carboxamide (Compound 38)

To a solution of triphosgene (119 mg) in chloroform (5 ml), a solution of triethylamine (169 μl) and 6-fluoro-3,4-dihydro-2H-1,4-benzoxazine obtained in Reference Example 18 (123 mg) in chloroform (3 ml) was added under ice cooling and stirred at the same temperature for 1 hour. To the reaction mixture, E-4-aminoadamantane-1-carboxamide obtained in Reference Example 30 (130 mg), triethylamine (141 μl) and N,N-dimethylformamide (5 ml) were then added and stirred overnight at room temperature. The reaction mixture was diluted with chloroform and washed with water. The organic layer was concentrated under reduced pressure, and the residue was diluted with ethyl acetate and washed sequentially with 1M aqueous hydrochloric acid, saturated aqueous sodium bicarbonate and brine. The organic layer was dried over anhydrous sodium sulfate and then filtered to remove the desiccant, followed by distilling off the solvent under reduced pressure. The resulting residue was dissolved in chloroform and then converted into a powder form by addition of diethyl ether, and the crystal was collected by filtration to give the titled compound (Compound 38, 101 mg) as an orange-colored powder.

1H NMR (300 MHz, CHLOROFORM-D) δ 1.53-1.75 (m, 4 H), 1.88-1.93 (m, 2 H), 1.94-2.09 (m, 5 H), 2.10-2.18 (m, 2 H), 3.81-3.90 (m, 2 H), 3.96-4.04 (m, 1 H), 4.19-4.27 (m, 2 H), 5.24 (brs, 1 H), 5.51-5.65 (m, 2 H), 6.73-6.83 (m, 1 H), 6.87-6.95 (m, 1 H), 7.11 (dd, J=9.8, 3.0 Hz, 1 H).

EXAMPLE 39

Synthesis of N-(E-5-carbamoyladamantan-2-yl)-6-methyl-2,3-dihydro-4H-1,4-benzoxazine-4-carboxamide (Compound 39)

To a solution of triphosgene (119 mg) in chloroform (5 ml), triethylamine (301 μl) and 6-methyl-3,4-dihydro-2H-1,4-benzoxazine hydrochloride obtained in Reference Example 15 (149 mg) were added under ice cooling and stirred at the same temperature for 30 minutes. To the reaction mixture, E-4-aminoadamantane-1-carboxamide obtained in Reference Example 30 (130 mg), triethylamine (141 μl) and N,N-dimethylformamide (5 ml) were then added and stirred overnight at room temperature. The reaction mixture was diluted with chloroform and washed with water. The organic layer was concentrated under reduced pressure, and the residue was diluted with ethyl acetate and washed sequentially with 1M aqueous hydrochloric acid, saturated aqueous sodium bicarbonate and brine. The organic layer was dried over anhydrous sodium sulfate and then filtered to remove the desiccant, followed by distilling off the solvent under reduced pressure. The resulting residue was purified by silica gel column chromatography (eluting solvent: n-hexane:ethyl acetate=1:1 to 1:2→chloroform:methanol=1:1). The resulting residue was dissolved in chloroform and then converted into a powder form by addition of diethyl ether, and the crystal was collected by filtration to give the titled compound (Compound 39, 66 mg) as a light-brown powder.

1H NMR (300 MHz, CHLOROFORM-D) δ 1.53-1.74 (m, 4 H), 1.87-1.93 (m, 2 H), 1.94-2.07 (m, 5 H), 2.08-2.16 (m, 2 H), 2.29 (s, 3 H), 3.82-3.90 (m, 2 H), 3.95-4.03 (m, 1 H), 4.18-4.26 (m, 2 H), 5.21 (brs, 1 H), 5.57 (brs, 1 H), 5.77 (d, J=7.9 Hz, 1 H), 6.81-6.92 (m, 2 H), 7.14 (s, 1 H).

EXAMPLE 40

Synthesis of N-(E-1-methoxyadamantan-4-yl)-2,3-dihydro-4H-1,4-benzoxazine-4-carboxamide (Compound 40)

To a solution of N-(E-1-hydroxyadamantan-4-yl)-2,3-dihydro-4H-1,4-benzoxazine 4-carboxamide obtained in Example 16 (100 mg) in acetonitrile (5 ml), methyl iodide (0.19 ml) and silver(I) oxide (348 mg) were added and stirred at room temperature for 3 days. The reaction mixture was then heated under reflux for 10 hours. After cooling at room temperature, the reaction mixture was filtered through celite, and the solvent was distilled off under reduced pressure. The resulting residue was purified by preparative TLC (developing solvent: n-hexane:ethyl acetate=1:1) and recrystallized from chloroform-diethyl ether to give the titled compound (Compound 40, 40 mg) as a light-brown powder.

1H NMR (300 MHz, CHLOROFORM-D) δ 1.43-1.67 (m, 4 H), 1.72-1.85 (m, 4 H), 1.86-1.99 (m, 3 H), 2.04-2.30 (m, 3 H), 3.23 (s, 3 H), 3.84-3.91 (m, 2 H), 3.91-4.06 (m, 1 H), 4.20-4.30 (m, 2 H), 5.57-5.74 (m, 1 H), 6.86-7.03 (m, 2 H), 7.02-7.14 (m, 1 H), 7.24-7.38 (m, 1 H).

EXAMPLE 41

Synthesis of N-(E-1-methylsulfonyladamantan-4-yl)-2,3-dihydro-4H-1,4-benzoxazine-4-carboxamide (Compound 41)

To a solution of 3,4-dihydro-2H-1,4-benzoxazine obtained in Reference Example 14 (27 mg) in chloroform (1 ml), triethylamine (0.08 ml) and triphosgene (29 mg) were added under ice cooling and stirred at the same temperature for 1 hour. Next, a solution of E-5-methylsulfonyladamantane-2-amine obtained in Reference Example 32 (42 mg) in chloroform (2 ml) was added at room temperature and stirred for 24 hours. The reaction mixture was diluted with ethyl acetate, washed sequentially with 1.2M aqueous hydrochloric acid and brine, dried over anhydrous magnesium sulfate and then filtered to remove the desiccant, followed by distilling off the solvent under reduced pressure. The resulting residue was purified by preparative TLC (developing solvent: n-hexane: ethyl acetate=1:1) and recrystallized from chloroform-diethyl ether to give the titled compound (Compound 41, 35 mg) as a colorless powder.

1H NMR (300 MHz, CHLOROFORM-D) δ 1.54-1.84 (m, 4 H), 1.91-2.39 (m, 9 H), 2.76 (s, 3 H), 3.89 (dd, J=5.2, 4.2 Hz, 2 H), 3.95-4.07 (m, 1 H) 4.26 (dd, J=5.2, 4.2 Hz, 2 H), 5.68 (d, J=6.4 Hz, 1 H), 6.87-7.02 (m, 2 H), 7.03-7.15 (m, 1 H), 7.22-7.36 (m, 1 H).

EXAMPLE 42

Synthesis of Z-5-hydroxyadamantan-2-yl 2,3-dihydro-4H-1,4-benzoxazine-4-carboxylate (Compound 42a) and E-5-hydroxyadamantan-2-yl 2,3-dihydro-4H-1,4-benzoxazine-4-carboxylate (Compound 42b)

To a solution of triphosgene (230 mg) in chloroform (5 ml), a solution of 5-benzyloxyadamantan-2-ol obtained in Reference Example 34 (500 mg) and triethylamine (0.41 ml) in chloroform (5 ml) was added under ice cooling and stirred at the same temperature for 1 hour. The reaction mixture was diluted with diethyl ether, washed sequentially with 1.2M aqueous hydrochloric acid and brine, dried over anhydrous magnesium sulfate and then filtered to remove the desiccant, followed by distilling off the solvent under reduced pressure. A solution of the resulting residue in diethyl ether (5 ml) was added dropwise to a solution of 3,4-dihydro-2H-1,4-benzoxazine obtained in Reference Example 14 (288 mg) in a mixture of diethyl ether (5 ml) and 8M aqueous sodium hydroxide (2 ml) under ice cooling. After the dropwise addition, the reaction mixture was warmed to room temperature and stirred for 24 hours. The reaction mixture was diluted with water and extracted with diethyl ether. The extracted organic layer was washed sequentially with 6M aqueous hydrochloric acid and brine, dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=9:1) to give 5-benzyloxyadamantan-2-yl 2,3-dihydro-4H-1,4-benzoxazine-4-carboxylate (a mixture of E- and Z-forms, 460 mg) as a colorless oil.

To a solution of the colorless oil thus obtained (460 mg) in ethanol (10 ml), palladium on activated carbon (50 mg) was added and stirred for 24 hours while purging with hydrogen. The reaction mixture was filtered through celite and the solvent was distilled off under reduced pressure. The resulting residue was purified by silica gel column chromatography (eluting solvent: chloroform alone) and recrystallized from n-hexane-diethyl ether to give the titled compound of low polarity (Compound 42a, 85 mg) as a colorless powder and the other titled compound of high polarity (Compound 42b, 102 mg) as a colorless powder.

Compound 42a

1H NMR (300 MHz, CHLOROFORM-D) δ 1.30-1.62 (m, 3 H), 1.62-1.82 (m, 6 H), 1.88-2.04 (m, 2 H), 2.10-2.19 (m, 1 H), 2.36-2.41 (m, 2 H), 3.86-3.99 (m, 2 H), 4.23-4.31 (m, 2 H), 4.87 (t, J=3.2 Hz, 1 H), 6.84-6.95 (m, 2 H), 6.96-7.05 (m, 1 H), 7.76-7.98 (m, 1 H).

Compound 42b

1H NMR (300 MHz, CHLOROFORM-D) δ 1.34-1.59 (m, 3 H), 1.62-1.99 (m, 8 H), 2.10-2.21 (m, 1 H), 2.22-2.34 (m, 2 H), 3.90-3.99 (m, 2 H), 4.23-4.31 (m, 2 H), 4.98 (t, J=3.6 Hz, 1 H), 6.84-6.95 (m, 2 H), 6.96-7.06 (m, 1 H), 7.75-7.96 (m, 1 H).

EXAMPLE 43

Synthesis of Z-5-hydroxyadamantan-2-yl 6-methyl-2,3-dihydro-4H-1,4-benzoxazine-4-carboxylate (Compound 43a) and E-5-hydroxyadamantan-2-yl 6-methyl-2,3-dihydro-4H-1,4-benzoxazine-4-carboxylate (Compound 43b)

To a solution of triphosgene (128 mg) in chloroform (5 ml), a solution of 6-methyl-3,4-dihydro-2H-1,4-benzoxazine hydrochloride obtained in Reference Example 15 (200 mg) and triethylamine (0.45 ml) in chloroform (5 ml) was added dropwise under ice cooling and stirred at the same temperature for 2 hours. The reaction mixture was diluted with 1.2M aqueous hydrochloric acid under ice cooling and extracted with chloroform. The extracted organic layer was washed with brine, dried over anhydrous magnesium sulfate and then filtered to remove the desiccant, followed by distilling off the solvent under reduced pressure to give a brown oil. Next, to a solution of 4-hydroxyadamantane-1-benzoate obtained in Reference Example 17 (324 mg) in N,N-dimethylformamide (5 ml), sodium hydride (60%, 73 mg) was added under ice cooling and stirred for 30 minutes. To this mixture, a solution of the brown oil obtained earlier in N,N-dimethylformamide (5 ml) was added dropwise. After completion of the dropwise addition, the reaction mixture was warmed to room temperature and stirred for 24 hours. The reaction mixture was diluted with ethyl acetate, washed sequentially with 1.2M aqueous hydrochloric acid and brine, dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=9:1) to give 4-{[(6-methyl-2,3-dihydro-4H-1,4-benzoxazin-4-yl)carbonyl]amino}adamantan-1-yl-benzoate (a mixture of E- and Z-forms, 135 mg) as a colorless oil.

To a solution of the colorless oil thus obtained (135 mg) in methanol (2 ml), 8M aqueous sodium hydroxide (1 ml) was added and stirred at room temperature for 4 days. After distilling off the solvent under reduced pressure, the residue was diluted with water and extracted with ethyl acetate. The extracted organic layer was washed sequentially with water and brine, dried over anhydrous magnesium sulfate and then filtered to remove the desiccant, followed by distilling off the solvent under reduced pressure. The resulting residue was purified by preparative TLC (developing solvent: n-hexane: ethyl acetate=1:1) to give the titled compound of low polarity (Compound 43a, 19 mg) as a light-brown powder and the other titled compound of high polarity (Compound 43b, 15 mg) as a brown powder.

Compound 43a

1H NMR (300 MHz, CHLOROFORM-D) δ 1.29-1.65 (m, 3 H), 1.68-1.77 (m, 6 H), 1.90-2.04 (m, 2 H), 2.08-2.20 (m, 1 H), 2.29 (s, 3 H), 2.33-2.43 (m, 2 H), 3.82-3.98 (m, 2 H), 4.20-4.28 (m, 2 H), 4.86 (t, J=3.3 Hz, 1 H), 6.74-6.85 (m, 2 H), 7.66-7.82 (m, 1 H).

Compound 43b

1H NMR (300 MHz, CHLOROFORM-D) δ 1.32-1.58 (m, 3 H), 1.65-2.03 (m, 8 H), 2.12-2.23 (m, 1 H), 2.24-2.37 (m, 5 H), 3.83-3.99 (m, 2 H), 4.17-4.31 (m, 2 H), 4.97 (t, J=3.6 Hz, 1 H), 6.67-6.91 (m, 2 H), 7.62-7.78 (m, 1 H).

EXAMPLE 44

Synthesis of Z-5-hydroxyadamantan-2-yl 6-fluoro-2,3-dihydro-4H-1,4-benzoxazine-4-carboxylate (Compound 44a) and E-5-hydroxyadamantan-2-yl 6-fluoro-2,3-dihydro-4H-1,4-benzoxazine-4-carboxylate (Compound 44b)

To a solution of triphosgene (230 mg) in chloroform (5 ml), a solution of 5-benzyloxyadamantan-2-ol obtained in Reference Example 34 (500 mg) and triethylamine (0.41 ml) in chloroform (5 ml) was added dropwise under ice cooling and stirred at the same temperature for 30 minutes. The reaction mixture was diluted with diethyl ether, washed sequentially with 1.2M aqueous hydrochloric acid and brine, dried over anhydrous magnesium sulfate and then filtered to remove the desiccant, followed by distilling off the solvent under reduced pressure. A solution of the resulting residue in diethyl ether (5 ml) was added dropwise to a solution of 6-fluoro-3,4-dihydro-2H-1,4-benzoxazine obtained in Reference Example 18 (327 mg) in a mixture of diethyl ether (5 ml) and 2M aqueous sodium hydroxide (3 ml) under ice cooling. After the dropwise addition, the reaction mixture was warmed to room temperature and stirred for 3 hours. The reaction mixture was diluted with water and extracted with diethyl ether. The extracted organic layer was washed sequentially with 1.2M aqueous hydrochloric acid and brine, dried over anhydrous magnesium sulfate and then filtered to remove the desiccant, followed by distilling off the solvent under reduced pressure. The resulting residue was purified by silica gel column chromatography (eluting solvent: n-hexane:ethyl acetate=19:1 to 9:1) to give 5-benzyloxyadamantan-2-yl 6-fluoro-2,3-dihydro-4H-1,4-benzoxazine-4-carboxylate (a mixture of E- and Z-forms, 530 mg) as a colorless oil.

To a solution of the colorless oil thus obtained (530 mg) in ethanol (10 ml), palladium on carbon (60 mg) was added and stirred for 24 hours while purging with hydrogen. The reaction mixture was filtered through celite and the solvent was distilled off under reduced pressure. The resulting residue was purified by silica gel column chromatography (eluting solvent: chloroform alone) and recrystallized from n-hexane-diethyl ether to give the titled compound of low polarity (Compound 44a, 35 mg) as a colorless powder and the other titled compound of high polarity (Compound 44b, 60 mg) as a colorless powder.

Compound 44a

1H NMR (300 MHz, CHLOROFORM-D) δ 1.32-1.64 (m, 4 H), 1.65-1.82 (m, 5 H), 1.88-2.02 (m, 2 H), 2.08-2.20 (m, 1 H), 2.36-2.40 (m, 2 H), 3.90-3.99 (m, 2 H), 4.18-4.24 (m, 2 H), 4.84 (t, J=3.0 Hz, 1 H), 6.66-6.75 (m, 1 H), 6.78-6.86 (m, 1 H), 7.74-7.92 (m, 1 H).

Compound 44b

1H NMR (300 MHz, CHLOROFORM-D) δ 1.34-1.64 (m, 3 H), 1.68-1.98 (m, 8 H), 2.15-2.22 (m, 1 H), 2.23-2.36 (m, 2 H), 3.89-3.98 (m, 2 H), 4.20-4.29 (m, 2 H), 4.99 (t, J=3.5 Hz, 1 H), 6.64-6.76 (m, 1 H), 6.78-6.88 (m, 1 H), 7.66-7.88 (m, 1 H).

EXAMPLE 45

Synthesis of 6-amino-N-(E-1-hydroxyadamantan-4-yl)-2,3-dihydro-4H-1,4-benzoxazine 4-carboxamide (Compound 45)

To a solution of E-4-aminoadamantan-1-ol obtained in Reference Example 2 (124 mg) in a mixture of chloroform (2 ml) and N,N-dimethylformamide (2 ml), N,N'-carbonyldiimidazole (132 mg) was added and stirred at room temperature for 30 minutes. To the reaction mixture, a solution of triethylamine (0.36 ml) and 6-nitro-3,4-dihydro-2H-1,4-benzoxazine hydrochloride obtained in Reference Example 23 (240 mg) in chloroform (5 ml) was then added and stirred at room temperature for 1 hour and then the resulting mixture was heated to reflux and stirred for 4 hours. After cooling at room temperature, the reaction mixture was diluted with ethyl acetate and washed sequentially with 1.2M aqueous hydrochloric acid and brine. The organic layer was dried over anhydrous magnesium sulfate and then filtered to remove the desiccant, followed by distilling off the solvent under reduced pressure. The resulting residue was purified by silica gel column chromatography (eluting solvent: chloroform:methanol=49:1) to give N-(E-1-hydroxyadamantan-4-yl)-6-nitro-2,3-dihydro-4H-1,4-benzoxazine 4-carboxamide (90 mg) as a light-yellow powder.

To a solution of the light-yellow powder thus obtained (90 mg) in ethanol (15 ml), palladium on carbon (10 mg) was added and stirred at room temperature for 24 hours while purging with hydrogen. The reaction mixture was filtered through celite and the solvent was distilled off under reduced pressure. The resulting residue was purified by silica gel column chromatography (eluting solvent: chloroform:methanol=9:1) to give the titled compound (Compound 45, 33 mg) as a light-brown amorphous substance.

1H NMR (300 MHz, CHLOROFORM-D) δ 1.28-1.68 (m, 5 H), 1.70-1.82 (m, 4 H), 1.83-1.98 (m, 2 H), 2.08-2.22 (m, 3 H), 3.78-3.88 (m, 2 H), 3.90-4.04 (m, 1 H), 4.12-4.25 (m, 2 H), 5.72 (d, J=5.8 Hz, 1 H), 6.45 (dd, J=8.7, 2.8 Hz, 1 H), 6.68 (d, J=2.8 Hz, 1 H), 6.77 (d, J=8.7 Hz, 1 H).

EXAMPLE 46

Synthesis of N-{E-5-[2-(methylsulfonyl)ethoxy]adamantan-2-yl}-2,3-dihydro-4H-1,4-benzoxazine-4-carboxamide (Compound 46)

To a solution of triphosgene (79 mg) in chloroform (2 ml), triethylamine (111 μl) and 3,4-dihydro-2H-1,4-benzoxazine obtained in Reference Example 14 (72 mg) were added under ice cooling and stirred at the same temperature for 10 minutes. To the reaction mixture, a solution of E-5-[2-(methylsulfonyl)ethoxy]adamantane-2-amine hydrochloride obtained in Reference Example 33 (150 mg) and triethylamine (101 μl) in chloroform (3 ml) was then added and stirred overnight at room temperature. The reaction mixture was diluted with water and extracted with ethyl acetate. The organic layer was washed sequentially with 0.5M aqueous hydrochloric acid, saturated aqueous sodium bicarbonate and brine. After drying over anhydrous magnesium sulfate, the desiccant was filtered off and the solvent was distilled off under reduced pressure. The resulting residue was purified by silica gel column chromatography (eluting solvent: chloroform alone→chloroform:methanol=47:3). The resulting residue was converted into a powder form by addition of a mixed solvent of diethyl ether and n-hexane, and then collected by filtration to give the titled compound (Compound 46, 166 mg) as a colorless powder.

1H NMR (300 MHz, CHLOROFORM-D) δ 1.45-1.64 (m, 4 H), 1.76-1.84 (m, 4 H), 1.86-1.95 (m, 2 H), 2.11-2.22 (m, 3 H), 3.01 (s, 3 H), 3.14-3.21 (m, 2 H), 3.83-3.91 (m, 4 H), 3.92-3.99 (m, 1 H), 4.25 (dd, J=4.9, 4.4 Hz, 2 H), 5.61-5.68 (m, 1 H), 6.90-6.99 (m, 2 H), 7.04-7.11 (m, 1 H), 7.27-7.31 (m, 1 H).

The compounds of the present invention obtained in the above examples are shown in Table 1.

TABLE 1

| Compound No. | Structural formula |
|---|---|
| A-1 | (3,4-dihydroquinolin-1(2H)-yl)-N-(3-hydroxyadamantan-1-yl)carboxamide |
| A-2 | 6-Cl-3,4-dihydroquinoline-1(2H)-carboxamide with 3-hydroxyadamantyl |
| A-3 | 6-Me-3,4-dihydroquinoline-1(2H)-carboxamide with 3-hydroxyadamantyl |
| A-4 | 6-MeO-3,4-dihydroquinoline-1(2H)-carboxamide with 3-hydroxyadamantyl |
| A-5 | 3,4-dihydroquinoline-1(2H)-carboxamide with adamantyl |
| A-6 | indoline-1-carboxamide with 3-hydroxyadamantyl |
| A-7 | N-Me-3,4-dihydroquinoline-1(2H)-carboxamide with 3-hydroxyadamantyl |

TABLE 1-continued

| Compound No. | Structural formula |
|---|---|
| 1 | 5-F-3,4-dihydroquinoline-1(2H)-carboxamide with 3-hydroxyadamantyl |
| 2 | 6-F-3,4-dihydroquinoline-1(2H)-carboxamide with 3-hydroxyadamantyl |
| 3 | 7-F-3,4-dihydroquinoline-1(2H)-carboxamide with 3-hydroxyadamantyl |
| 4 | 8-F-3,4-dihydroquinoline-1(2H)-carboxamide with 3-hydroxyadamantyl |
| 5 | 8-OMe-3,4-dihydroquinoline-1(2H)-carboxamide with 3-hydroxyadamantyl |
| 6 | 8-Me-3,4-dihydroquinoline-1(2H)-carboxamide with 3-hydroxyadamantyl |
| 7 | 6-CN-3,4-dihydroquinoline-1(2H)-carboxamide with 3-hydroxyadamantyl |

TABLE 1-continued

| Compound No. | Structural formula |
|---|---|
| 8 | |
| 9a, 9b | |
| 10a, 10b | |
| 11a, 11b | |
| 12 | |
| 13 | |
| 14 | |
| 15 | |
| 16 | |
| 17 | |
| 18a, 18b | |
| 19 | |
| 20 | |
| 21 | |
| 22 | |

TABLE 1-continued

| Compound No. | Structural formula |
|---|---|
| 23 | 7-methyl-benzoxazine adamantanol urea |
| 24 | 7-fluoro-benzoxazine adamantanol urea |
| 25 | 8-methyl-benzoxazine adamantanol urea |
| 26 | 6-trifluoromethyl-benzoxazine adamantanol urea |
| 27 | benzothiazine adamantanol urea |
| 28 | benzothiazine S-oxide adamantanol urea |
| 29 | benzothiazine S,S-dioxide adamantanol urea |
| 30 | 1-acetyl-tetrahydroquinoxaline adamantanol urea |
| 31 | 1-tert-butoxycarbonyl-tetrahydroquinoxaline adamantanol urea |
| 32 | tetrahydroquinoxaline adamantanol urea HCl |
| 33 | 1-methyl-tetrahydroquinoxaline adamantanol urea HCl |
| 34 | benzoxazine adamantyl urea |
| 35a, 35b | benzoxazine adamantyl-CO$_2$Me urea |
| 36a, 36b | benzoxazine adamantyl-COOH urea |

TABLE 1-continued

| Compound No. | Structural formula |
|---|---|
| 37a, 37b | (benzoxazine-N-C(=O)-NH-adamantyl-CONH2) |
| 38 | (6-F-benzoxazine-N-C(=O)-NH-adamantyl-CONH2) |
| 39 | (6-Me-benzoxazine-N-C(=O)-NH-adamantyl-CONH2) |
| 40 | (benzoxazine-N-C(=O)-NH-adamantyl-OMe) |
| 41 | (benzoxazine-N-C(=O)-NH-adamantyl-SO2Me) |
| 42a, 42b | (benzoxazine-N-C(=O)-O-adamantyl-OH) |
| 43a, 43b | (6-Me-benzoxazine-N-C(=O)-O-adamantyl-OH) |
| 44a, 44b | (6-F-benzoxazine-N-C(=O)-O-adamantyl-OH) |
| 45 | (6-NH2-benzoxazine-N-C(=O)-NH-adamantyl-OH) |
| 46 | (benzoxazine-N-C(=O)-NH-adamantyl-O-CH2CH2-SO2Me) |

Test Example [11β-HSD1 Inhibition Test]

Test Compounds were Evaluated as Follows.

11β-HSD1 enzyme reaction was performed in a reaction solution of 100 µl total volume using 96-well polypropylene microplates. The reaction solution was prepared in 30 mM Tris-HCl (pH 7.4)/1 mM EDTA buffer to contain NADPH at a final concentration of 100 µM, G6P at a final concentration of 1 mM, human liver microsome (enzyme source, Tissue Transformation Technologies) at a final concentration of 0.8 µg/ml and 10 µl of a test compound dissolved in DMSO. The enzyme reaction was initiated by addition of cortisone at a final concentration of 100 nM. After incubation at 20° C. for 80 minutes, 10 µl of 1 mM 18β glycyrrhetinic acid, which is a non-specific inhibitor, was added to stop the reaction. Next, the amount of generated cortisol was quantified with a detection kit (Sceti Medical Labo K.K., Japan) according to the HTRF (Homogeneous Time-Resolved Fluorescence) method. This system detects fluorescence resonance energy transfer between europium-labeled anti-cortisol antibody and XL665-labeled cortisol. Upon addition of unlabeled cortisol, binding signals will be attenuated due to competitive reaction. Based on this principle, the amount of cortisol generated by the enzyme reaction was evaluated using a standard curve obtained from samples with known concentrations of cortisol included in the kit. The HTRF reaction was performed in 96-well half area microplates as follows: to 30 µl enzyme reaction solution, an anti-cortisol antibody solution (15 µl) and an XL665-labeled cortisol solution (15 µl) included in the kit were added, and the plates were vortexed at room temperature for 1 hour and further allowed to stand at 20° C. for 1 hour. 40 µl of this reaction solution was transferred to 384-well microplates and measured for its fluorescence. 18β Glycyrrhetinic acid was added to wells before initiation of the enzyme reaction and the amount of cortisol generated in these wells was used as a background level. Test compounds were evaluated using serial dilutions at a common ratio of 3 to calculate their IC50 values, assuming that the amount of cortisol generated in wells containing no test compound was set to 100% enzyme activity.

Table 2 shows the IC50 values for the compounds of the present invention.

TABLE 2

| Compound No. | IC50 value (nM) |
|---|---|
| A-1 | 0.7 |
| A-2 | 0.9 |
| A-5 | 1.5 |
| A-6 | 8.3 |
| A-7 | 9.6 |
| 1 | 1.0 |
| 2 | 0.9 |
| 3 | 1.0 |
| 4 | 1.1 |
| 5 | 1.2 |
| 6 | 0.6 |
| 7 | 2.8 |
| 8 | 0.9 |
| 10b | 17.5 |
| 11b | 0.8 |
| 12 | 1.0 |
| 13 | 1.2 |
| 14 | 2.0 |
| 16 | 1.5 |
| 17 | 0.8 |
| 18b | 0.9 |
| 19 | 3.5 |
| 20 | 6.7 |
| 23 | 1.1 |
| 24 | 1.1 |
| 25 | 1.1 |
| 26 | 3.4 |
| 27 | 0.7 |
| 32 | 1.4 |
| 33 | 1.4 |
| 34 | 1.1 |
| 37b | 0.6 |
| 38 | 0.6 |
| 39 | 0.6 |
| 40 | 1.1 |
| 41 | 34.7 |
| 42b | 4.6 |
| 43b | 3.2 |
| 44b | 9.5 |

Industrial Applicability

The present invention enables the provision of pharmaceutical preparations having an excellent inhibitory effect against 11β-HSD1 and being effective for prevention or treatment of diabetes or other diseases, which are expected to reduce burden on patients and contribute to the development of pharmaceutical industries.

The invention claimed is:

1. A compound represented by the following formula (I):

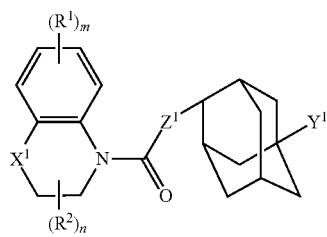

(I)

[wherein
X$^1$ represents an oxygen atom, or the formula —(CR$^{11}$R$^{12}$)$_p$— (wherein R$^{11}$ and R$^{12}$, which may be the same or different, each represent a hydrogen atom or a C$_{1-4}$ alkyl group, and p represents an integer of 0 to 2), a sulfur atom, the formula —S(O)—, the formula —S(O)$_2$—, or the formula —N(R$^{13}$)— (wherein R$^{13}$ represents a hydrogen atom, a C$_{1-4}$ alkyl group, a C$_{1-4}$ alkylcarbonyl group or a C$_{1-4}$ alkoxycarbonyl group), Y$^1$ represents a hydrogen atom, a hydroxyl group, a halogen atom, a C$_{1-4}$ alkoxy group, a C$_{1-4}$ alkoxycarbonyl group, a carboxyl group, a carbamoyl group, a C$_{1-4}$ alkylsulfonyl group, a C$_{1-4}$ alkylsulfonyl-C$_{1-4}$ alkoxy group, or a carbamoylmethoxy group, Z$^1$ represents an oxygen atom or the formula —(NR$^{14}$)— (wherein R$^{14}$ represents a hydrogen atom or a C$_{1-4}$ alkyl group), R$^1$ represents a hydrogen atom, a halogen atom, a cyano group, a C$_{1-4}$ alkyl group, a C$_{1-4}$ alkyl group substituted with 1 to 3 halogen atoms, a C$_{1-4}$ alkoxy group, a C$_{1-4}$ alkoxycarbonyl group, a carboxyl group, a carbamoyl group, or an amino group, and m represents an integer of 1 or 2, and R$^2$ represents a hydrogen atom or a C$_{1-4}$ alkyl group, and n represents an integer of 1 or 2].

2. A compound represented by the following formula (II):

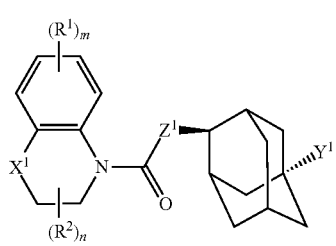

(II)

[wherein
X$^1$ represents an oxygen atom, or the formula —(CR$^{11}$R$^{12}$)$_p$— (wherein R$^{11}$ and R$^{12}$, which may be the same or different, each represent a hydrogen atom or a C$_{1-4}$ alkyl group, and p represents an integer of 0 to 2), a sulfur atom, the formula —S(O)—, the formula —S(O)$_2$—, or the formula —N(R$^{13}$)— (wherein R$^{13}$ represents a hydrogen atom, a C$_{1-4}$ alkyl group, a C$_{1-4}$ alkylcarbonyl group or a C$_{1-4}$ alkoxycarbonyl group), Y$^1$ represents a hydroxyl group, a halogen atom, a C$_{1-4}$ alkoxy group, a C$_{1-4}$ alkoxycarbonyl group, a carboxyl group, a carbamoyl group, a C$_{1-4}$ alkylsulfonyl group, a C$_{1-4}$ alkylsulfonyl-C$_{1-4}$ alkoxy group, or a carbamoylmethoxy group, Z$^1$ represents an oxygen atom or the formula —(NR$^{14}$)— (wherein R$^{14}$ represents a hydrogen atom or a C$_{1-4}$ alkyl group), R$^1$ represents a hydrogen atom, a halogen atom, a cyano group, a C$_{1-4}$ alkyl group, a C$_{1-4}$ alkyl group substituted with 1 to 3 halogen atoms, a C$_{1-4}$ alkoxy group, a C$_{1-4}$ alkoxycarbonyl group, a carboxyl group, a carbamoyl group, or an amino group, and m represents an integer of 1 or 2, and R$^2$ represents a hydrogen atom or a C$_{1-4}$ alkyl group, and n represents an integer of 1 or 2].

3. A compound represented by the following formula (III):

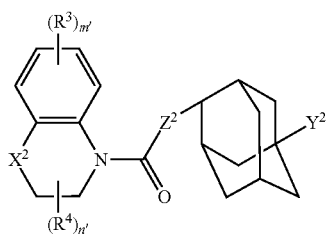

(III)

[wherein
- $X^2$ represents an oxygen atom or the formula —$(CR^{21}R^{22})_r$— (wherein $R^{21}$ and $R^{22}$, which may be the same or different, each represent a hydrogen atom or a $C_{1-4}$ alkyl group, and r represents an integer of 0 to 2),
- $Y^2$ represents a hydrogen atom, a hydroxyl group, a halogen atom, a $C_{1-4}$ alkoxy group, a $C_{1-4}$ alkoxycarbonyl group, a carboxyl group, or a carbamoyl group,
- $Z^2$ represents an oxygen atom or the formula —$(NR^{23})$— (wherein $R^{23}$ represents a hydrogen atom or a $C_{1-4}$ alkyl group),
- $R^3$ represents a hydrogen atom, a halogen atom, a cyano group, a $C_{1-4}$ alkyl group, or a $C_{1-4}$ alkoxy group, and m' represents an integer of 1 or 2, and
- $R^4$ represents a hydrogen atom or a $C_{1-4}$ alkyl group, and n' represents an integer of 1 or 2].

4. A compound represented by the following formula (IV):

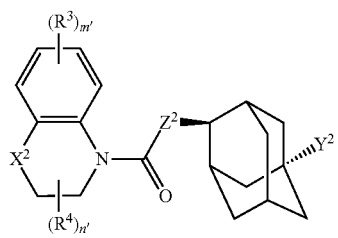

(IV)

[wherein
- $X^2$ represents an oxygen atom or the formula —$(CR^{21}R^{22})_r$— (wherein $R^{21}$ and $R^{22}$, which may be the same or different, each represent a hydrogen atom or a $C_{1-4}$ alkyl group, and r represents an integer of 0 to 2),
- $Y^2$ represents a hydroxyl group, a halogen atom, a $C_{1-4}$ alkoxy group, a $C_{1-4}$ alkoxycarbonyl group, a carboxyl group, or a carbamoyl group,
- $Z^2$ represents an oxygen atom or the formula —$(NR^{23})$— (wherein $R^{23}$ represents a hydrogen atom or a $C_{1-4}$ alkyl group),
- $R^3$ represents a hydrogen atom, a halogen atom, a cyano group, a $C_{1-4}$ alkyl group, or a $C_{1-4}$ alkoxy group, and m' represents an integer of 1 or 2, and
- $R^4$ represents a hydrogen atom or a $C_{1-4}$ alkyl group, and n' represents an integer of 1 or 2].

5. A compound represented by the following formula (V):

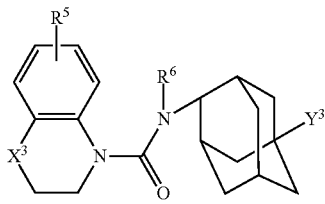

(V)

[wherein
- $X^3$ represents —$(CH_2)_s$— (wherein s represents an integer of 0 or 1),
- $Y^3$ represents a hydrogen atom or a hydroxyl group,
- $R^5$ represents a hydrogen atom, a halogen atom, a $C_{1-4}$ alkyl group or a $C_{1-4}$ alkoxy group, and
- $R^6$ represents a hydrogen atom or a $C_{1-4}$ alkyl group].

6. The compound of formula (V) according to claim 5, wherein $Y^3$ is a hydroxyl group.

7. A compound represented by the following formula (VI):

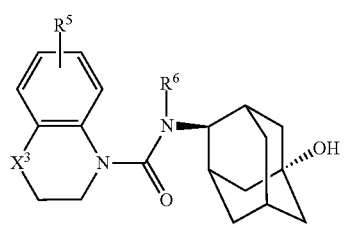

(VI)

[wherein
- $X^3$ represents —$(CH_2)_s$— (wherein s represents an integer of 0 or 1),
- $R^5$ represents a hydrogen atom, a halogen atom, a $C_{1-4}$ alkyl group or a $C_{1-4}$ alkoxy group, and
- $R^6$ represents a hydrogen atom or a $C_{1-4}$ alkyl group].

8. A pharmaceutical composition which comprises the compound according to claim 1 and a pharmaceutical acceptable carrier.

9. A method for treating type II diabetes, which comprises administering to a subject in need thereof an effective amount of the compound according to claim 1.

* * * * *